(12) United States Patent
Acker et al.

(10) Patent No.: US 10,543,325 B2
(45) Date of Patent: Jan. 28, 2020

(54) ENHANCED PERFORMANCE VERIFICATION PORT FOR THERAPEUTIC GAS DELIVERY

(71) Applicant: Mallinckrodt Hospital Products IP Limited, Dublin (IE)

(72) Inventors: Jaron M. Acker, Madison, WI (US); John C. Falligant, Edgerton, WI (US); Jeff Milsap, Cambridge, WI (US); Robin Roehl, Janesville, WI (US); Jeffrey Schmidt, Fitchburg, WI (US); Craig R. Tolmie, Stoughton, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 1056 days.

(21) Appl. No.: 14/709,308

(22) Filed: May 11, 2015

(65) Prior Publication Data

US 2015/0320952 A1 Nov. 12, 2015

Related U.S. Application Data

(60) Provisional application No. 61/991,083, filed on May 9, 2014, provisional application No. 61/991,028, filed
(Continued)

(51) Int. Cl.
*A61M 16/00* (2006.01)
*B63C 11/02* (2006.01)
(Continued)

(52) U.S. Cl.
CPC ...... *A61M 16/0051* (2013.01); *A61M 16/024* (2017.08); *A61M 16/1005* (2014.02);
(Continued)

(58) Field of Classification Search
CPC .............. A61M 16/0051; A61M 16/12; A61M 16/204; A61M 16/202; A61M 16/125;
(Continued)

(56) References Cited

U.S. PATENT DOCUMENTS 5,558,083 A 9/1996 Bathe et al.
5,732,693 A 3/1998 Bathe et al.
(Continued)

FOREIGN PATENT DOCUMENTS

WO 0195972 A2 12/2001
WO WO-01/95972 12/2001

OTHER PUBLICATIONS

PCT International Search Report and Written Opinion in PCT/US2015/030217, dated Oct. 19, 2015, 24 pages.
(Continued)

*Primary Examiner* — Steven O Douglas

(57) ABSTRACT

Therapy gas delivery systems that provide run-time-to-empty information to a user of the system and methods for administering therapeutic gas to a patient. The therapeutic gas delivery system may include a gas pressure sensor attachable to a therapeutic gas source that communicates therapeutic gas pressure data to a therapeutic gas delivery system controller, a gas temperature sensor positioned to measure gas temperature in the therapeutic gas source that communicates therapeutic gas temperature data to the therapeutic gas delivery system controller, at least one flow controller that communicates therapeutic gas flow rate data to the therapeutic gas delivery system controller, at least one flow sensor that communicates flow rate data to the therapeutic gas delivery system controller, and at least one display that communicates run-time-to-empty to a user of the therapeutic gas delivery system. The therapeutic gas delivery system controller of the system includes a processor that executes an algorithm to calculate the run-time-to-empty from the data received from the gas pressure sensor, temperature sensor, flow controller and flow sensor, and directs the result to the display.

9 Claims, 8 Drawing Sheets

Related U.S. Application Data on May 9, 2014, provisional application No. 61/991,032, filed on May 9, 2014.

(51) Int. Cl.

| | | |
|---|---|---|
| *G01F 22/02* | (2006.01) | |
| *A61M 16/20* | (2006.01) | |
| *A61M 16/12* | (2006.01) | |
| *A61M 16/10* | (2006.01) | |
| *A61M 16/08* | (2006.01) | |

(52) U.S. Cl.
CPC .......... *A61M 16/12* (2013.01); *A61M 16/122* (2014.02); *A61M 16/125* (2014.02); *A61M 16/201* (2014.02); *A61M 16/202* (2014.02); *A61M 16/204* (2014.02); *B63C 11/02* (2013.01); *G01F 22/02* (2013.01); *A61M 16/085* (2014.02); *A61M 16/208* (2013.01); *A61M 2016/0027* (2013.01); *A61M 2016/0039* (2013.01); *A61M 2016/102* (2013.01); *A61M 2202/0275* (2013.01); *A61M 2205/14* (2013.01); *A61M 2205/16* (2013.01); *A61M 2205/17* (2013.01); *A61M 2205/3331* (2013.01); *A61M 2205/3334* (2013.01); *A61M 2205/3368* (2013.01); *A61M 2205/3379* (2013.01); *A61M 2205/50* (2013.01); *A61M 2205/502* (2013.01); *A61M 2205/60* (2013.01); *A61M 2205/6018* (2013.01); *A61M 2205/6072* (2013.01); *A61M 2205/8206* (2013.01); *F17C 2250/00* (2013.01)

(58) Field of Classification Search
CPC ............ A61M 16/1005; A61M 16/201; A61M 16/122; A61M 2205/6018; A61M 2205/50; A61M 2205/3368; A61M 2205/17

See application file for complete search history.

(56) References Cited

U.S. PATENT DOCUMENTS

| | | | |
|---|---|---|---|
| 5,752,504 A | | 5/1998 | Bathe |
| 5,827,950 A | * | 10/1998 | Woodbury .............. F23N 5/242 73/40.5 R |
| 6,089,229 A | | 7/2000 | Bathe et al. |
| 6,125,846 A | | 10/2000 | Bathe et al. |
| 7,159,608 B1 | | 1/2007 | Lucas, Jr. et al. |
| 7,523,752 B2 | | 4/2009 | Montgomery et al. |
| 8,282,966 B2 | | 10/2012 | Baldassarre et al. |
| 8,291,904 B2 | | 10/2012 | Bathe et al. |
| 8,293,284 B2 | | 10/2012 | Baldassarre et al. |
| 8,431,163 B2 | | 4/2013 | Baldassarre et al. |
| 8,573,209 B2 | | 11/2013 | Bathe et al. |
| 8,573,210 B2 | | 11/2013 | Bathe et al. |
| 8,757,148 B2 | | 6/2014 | Montgomery et al. |
| 8,776,794 B2 | | 7/2014 | Bathe et al. |
| 8,776,795 B2 | | 7/2014 | Bathe et al. |
| 8,795,741 B2 | | 8/2014 | Baldassarre |
| 8,846,112 B2 | | 9/2014 | Baldassarre |
| 2003/0189492 A1 | | 10/2003 | Harvie |
| 2008/0150739 A1 | * | 6/2008 | Gamard ................ F17C 13/003 340/626 |
| 2012/0080103 A1 | | 4/2012 | Levine et al. |
| 2014/0048063 A1 | | 2/2014 | Bathe et al. |

OTHER PUBLICATIONS

INOmax DS (Delivery System): Operation Manual (800 ppm INOMAX (nitric oxide) for Inhalation), *Ikaria, Inc.* 2010, 112 pages.
INOvent Delivery System: Operation and Maintenance Manual (CGA Variant), *Datex-Ohmeda, Inc.* 2000, 180 pages.
Using the INOpulse DS Subject Guide, *Ikaria, Inc.* 2012, 50 pages.
INOmax Label, Nitric Oxide Gas, *INO Therapeutics* 2013, 2 pages.
INOmax DSIR (Delivery System): Operation Manual (800 ppm INOMAX (nitric oxide) for Inhalation), Ikaria, Inc. 2012, 136 pages.
Annex to Form PCT/ISA/206 Communication Related to the Results of the Partial International Search in PCT/US2015/030217, dated Aug. 4, 2015, 7 pages.
INOmax $DS_{IR}$ INOblender—Pre-Use Checkout, *Ikaria, Inc.* 2014, 2 pages.
INOblender Operations Manual, *Ikaria, Inc.* 2010, 34 pages.
Office action regarding U.S. Appl. No. 14/709,316 dated Feb. 1, 2018, 10 pages.
Office action regarding U.S. Appl. No. 14/709,316 dated Sep. 5, 2018, 11 pages.
Office action regarding U.S. Appl. No. 14/709,316 dated Feb. 26, 2019, 11 pages.
Office Action regarding AU Application No. 2015255688 dated Jun. 7, 2019, 8 pages.
International Search Report and Written Opinion; PCT Application No. PCT/US2015/030217; dated Oct. 19, 2015, 23 pages.

* cited by examiner

ENHANCED PERFORMANCE VERIFICATION PORT FOR THERAPEUTIC GAS DELIVERY

CROSS-REFERENCE TO RELATED APPLICATIONS

This application claims the benefit under 35 U.S.C. § 119(e) to U.S. Provisional Application No. 61/991,028, filed May 9, 2014, U.S. Provisional Application No. 61/991,032, filed May 9, 2014, and U.S. Provisional Application No. 61/991,083, filed May 9, 2014, the entire contents of which are incorporated herein by reference in their entirety.

TECHNICAL FIELD

Systems and methods for managing delivery of a therapy gas from a gas source to a subject, and in particular to management of delivery of inhaled therapy gases, are described.

BACKGROUND

Certain medical treatments include the use of therapy gases that are inhaled by the patient. Gas delivery systems are often utilized by hospitals to control the rate of therapy gas delivery to the patient in need thereof, to verify the correct type of gas and the correct concentration are being used. Gas delivery systems may also verify dosage information, patient information and therapy gas administration.

Known therapy gas delivery systems may include a computerized system for tracking patient information, including information regarding the type of gas therapy, concentration of therapy gas to be administered and dosage information for a particular patient. While these computerized systems may communicate with other components of the therapy gas delivery system, such as the valve on the gas source that controls the flow of gas to the computerized system and/or the ventilator for administration to the patient, such communication has not included an ability to determine the amount of treatment time left before the therapy gas remaining in the gas source falls below a predetermined minimum or the gas source is empty.

There is a need for a therapy gas delivery system that addresses at least the above.

SUMMARY

Various embodiments are listed below. It will be understood that the embodiments listed below may be combined not only as listed, but in other suitable combinations in accordance with the spirit and scope of the invention.

A first embodiment relates to a therapeutic gas delivery system, comprising at least one gas supply subsystem comprising, a gas source coupling configured to receive a therapeutic gas source and form a fluid flow connection with the therapeutic gas source, a gas source valve adjacent to and in fluid communication with the gas source coupling, wherein the gas source valve is configured to have at least an open state and a closed state, a gas pressure sensor adjacent to and in fluid communication with the gas source valve, wherein the gas source valve provides a gas flow path from the gas source coupling to the gas pressure sensor, and the gas pressure sensor is configured to measure a gas pressure at the gas source coupling at least when the gas source valve is in an open state, to be in communication over a communication path with a therapeutic gas delivery system controller comprising a CPU, and to communicate a pressure value over the communication path to the therapeutic gas delivery system controller, and a therapeutic gas flow regulator down stream from the gas pressure sensor, gas source valve, and gas source coupling, and in fluid communication with the gas source coupling, gas source valve, and gas pressure sensor, one or more display(s) configured to be in communication over a communication path with the therapeutic gas delivery system controller, wherein the CPU of the therapeutic gas delivery system controller is configured to calculate a value for a run-time-to-empty from a volume value, a pressure value communicated from the gas pressure sensor, and an average therapeutic gas consumption rate calculated by the CPU from the gas flow rate value communicated from the therapeutic gas flow controller, and wherein the system display is configured to display the calculated run-time-to-empty value.

In a second embodiment, the therapeutic gas delivery system of the first embodiment may be modified to further comprise a therapeutic gas source having a volume and containing a therapeutic gas at an initial pressure within the volume, wherein the therapeutic gas source is configured to be operatively associated with the gas source coupling, and wherein the volume value of the therapeutic gas source is inputted to the therapeutic gas delivery system controller.

In a third embodiment, the therapeutic gas delivery system of the first and/or second embodiments may be modified to have the gas supply subsystem further comprise a therapeutic gas conduit having an interior volume that provides a gas flow path at least from the gas source coupling to the gas source valve, and a temperature sensor operatively associated with the therapeutic gas source or the therapeutic gas conduit, wherein the temperature sensor is configured to measure a temperature of the therapeutic gas source, the therapeutic gas conduit, or the therapeutic gas, to be in communication over a communication path with a therapeutic gas delivery system controller, and to communicate a temperature value over the communication path to the therapeutic gas delivery system controller.

In a fourth embodiment, the therapeutic gas delivery system of the first through third embodiments may be modified to have the gas supply subsystem further comprise a gas source identifier attached to the therapeutic gas source, wherein the gas source identifier contains information at least of the gas source volume and the identity of the therapeutic gas supplied by the therapeutic gas source, and a gas source identifier reader operatively associated with the therapeutic gas delivery system, and in communication over a communication path with the therapeutic gas delivery system controller, wherein the gas source identifier reader is configured to obtain identifying information from the gas source identifier when the therapeutic gas source is properly received by the gas source coupling, and communicate the identifying information to the therapeutic gas delivery system controller.

In a fifth embodiment, the therapeutic gas delivery system of the first through fourth embodiments may be modified in a manner wherein the therapeutic gas source is a compressed gas cylinder, and the gas source identifier is selected from the group consisting of RFID, a QR code, a bar code, or combinations thereof, which is affixed to an outer surface of the compressed gas cylinder.

In a sixth embodiment, the therapeutic gas delivery system of the first through fifth embodiments may be modified in a manner wherein the gas supply subsystem further comprises a therapeutic gas source detector operatively associated with the gas source coupling, wherein the therapeutic gas source detector is configured to detect when the therapeutic gas source is properly received by the gas source coupling, and communicate a signal of the presence of the therapeutic gas source to the therapeutic gas delivery system controller.

In a seventh embodiment, the therapeutic gas delivery system of the first through sixth embodiments may be modified in a manner wherein the therapeutic gas delivery system controller is configured to obtain identifying information from the gas source identifier when the therapeutic gas source detector detects the therapeutic gas source is properly received by the gas source coupling, and communicate a signal to the gas source valve adjacent to the gas source coupling to transition to an open state, and wherein the therapeutic gas flow regulator is configured to be in communication over a communication path with the therapeutic gas delivery system controller.

In an eighth embodiment, the therapeutic gas delivery system of the first through seventh embodiments, may be modified in a manner wherein the therapeutic gas delivery system controller is configured to obtain a gas pressure value communicated from the gas pressure sensor, and a gas flow rate value from a flow controller, and calculate a run-time-to-empty value for the therapeutic gas source.

In a ninth embodiment, the therapeutic gas delivery system of the first through eighth embodiments, may be modified in a manner wherein the therapeutic gas delivery system controller is configured to calculate the run-time-to-empty value for the therapeutic gas source from at least the gas pressure value, the temperature of the therapeutic gas source, the gas source volume, and an average therapeutic gas consumption rate.

In a tenth embodiment, the therapeutic gas delivery system of the first through ninth embodiments, may be modified in a manner wherein the therapeutic gas delivery system controller comprises hardware, software, firmware, or a combination thereof configured to perform a run-time-to-empty calculation.

In an eleventh embodiment, the therapeutic gas delivery system of the first through tenth embodiments, may be modified in a manner wherein at least one of the one or more display(s) is a status display that is configured to present at least the run-time-to-empty value.

In a twelfth embodiment, the therapeutic gas delivery system of the first through eleventh embodiments, may be modified in a manner wherein at least one of the one or more display(s) is a status display operatively associated with at least one gas supply subsystem that is configured to present a bar graph, a chart, a numerical display of a value, a visual alarm, identifying information from the gas source identifier, or a combination thereof.

In a thirteenth embodiment, the therapeutic gas delivery system of the first through twelfth embodiments, may be modified in a manner wherein at least one status display operatively associated with at least one gas supply subsystem is configured to provide a user interface that is configured to provide control of the therapeutic gas delivery system.

In a fourteenth embodiment, the therapeutic gas delivery system of the first through thirteenth embodiments, may be modified in a manner wherein the therapeutic gas delivery system controller is configured to include a residual gas pressure value in the calculation of the run-time-to-empty value for the therapeutic gas source.

In a fifteenth embodiment, the therapeutic gas delivery system of the first through fourteenth embodiments, may be modified in a manner wherein the gas supply subsystem further comprises a gas supply subsystem valve in between and in fluid communication with the gas source valve and the therapeutic gas flow regulator, wherein the gas supply subsystem valve is configured to maintain the therapeutic gas under pressure between the gas supply subsystem valve and the therapeutic gas flow regulator.

In a sixteenth embodiment, the therapeutic gas delivery system of the first through fifteenth embodiments, may be modified in a manner wherein the gas supply subsystem valve is a mechanically activated check valve configured to be opened by a cylinder being received, wherein the gas supply subsystem valve avoids sudden release of pressure and prevents air/O2 from entering between the gas supply subsystem valve and the therapeutic gas flow regulator.

In a seventeenth embodiment, the therapeutic gas delivery system of the first through sixteenth embodiments, may be modified in a manner wherein the therapeutic gas delivery system comprises two or more gas supply subsystems, wherein the therapeutic gas delivery system controller is configured to calculate the run-time-to-empty value for each therapeutic gas source in each of the two or more gas supply subsystems, and wherein the therapeutic gas delivery system controller communicates a signal to the gas supply subsystem valve for the therapeutic gas source calculated to have the shortest run-time-to-empty value to transition to an open state.

In an eighteenth embodiment, the therapeutic gas delivery system of the first through seventeenth embodiments, may be modified in a manner wherein the therapeutic gas delivery system controller further comprises two or more subsystem controllers, wherein each of the two or more gas supply subsystems comprises one subsystem controller, and wherein each of the two or more gas supply subsystems is configured to be controlled by the two or more subsystem controllers.

In an nineteenth embodiment, the therapeutic gas delivery system of the first through eighteenth embodiments, may be modified in a manner wherein each of the two or more subsystem controllers is configured to operate the two or more gas supply subsystems to continue delivering the therapeutic gas if another of the two or more subsystem controllers fails.

In a twentieth embodiment, the therapeutic gas delivery system of the first through nineteenth embodiments may be modified in a manner which further comprises a primary delivery system, further comprising a first primary shut off valve, wherein the first primary shut off valve is down stream from the two or more gas supply subsystems, and in fluid communication with the therapeutic gas flow regulators and gas pressure sensors of the two or more gas supply subsystems, a first primary high flow control valve, wherein the first primary high flow control valve is downstream from and in fluid communication with the first primary shut off valve, a first primary delivery flow sensor, wherein the first primary delivery flow sensor is downstream from and in fluid communication with the first primary high flow control valve, and a first primary confirmatory flow sensor, wherein the first primary confirmatory flow sensor is downstream from and in fluid communication with the first primary delivery flow sensor.

In a twenty-first embodiment, the therapeutic gas delivery system of the first through twentieth embodiments may be modified in a manner wherein the primary delivery system further comprises a second primary shut off valve, wherein the second primary shut off valve is down stream from the two or more gas supply subsystems, and in fluid communication with the therapeutic gas flow regulators and gas pressure sensors of the two or more gas supply subsystems, a second primary high flow control valve, wherein the second primary high flow control valve is downstream from and in fluid communication with the second primary shut off valve, a second primary delivery flow sensor, wherein the second primary delivery flow sensor is downstream from and in fluid communication with the second primary high flow control valve, and a second primary confirmatory flow sensor, wherein the second primary confirmatory flow sensor is downstream from and in fluid communication with the second primary delivery flow sensor.

In a twenty-second embodiment, the therapeutic gas delivery system of the first through twenty-first embodiments may be modified in a manner wherein the first primary delivery flow sensor and the first primary confirmatory flow sensor are configured to measure a gas flow rate at least when the first primary shut off valve and first primary high flow control valve are in an open state, to be in communication over a communication path with a therapeutic gas delivery system controller, and to communicate a gas flow rate value over the communication path to the therapeutic gas delivery system controller, and wherein the therapeutic gas delivery system controller is configured to compare the gas flow rate value from the first primary delivery flow sensor to the gas flow rate value from the first primary confirmatory flow sensor, and determine the difference between the two gas flow rate values.

In a twenty-third embodiment, the therapeutic gas delivery system of the first through twenty-second embodiments may be modified in a manner wherein the primary delivery system is configured to provide therapeutic gas at a controlled flow rate to an injector module for wild stream blending with an air/$O_2$ flow stream from a respirator.

In a twenty-fourth embodiment, the therapeutic gas delivery system of the first through twenty-third embodiments may be modified in a manner wherein the first primary high flow control valve, first primary delivery flow sensor, and the first primary confirmatory flow sensor are configured to provide a feedback control loop to adjust the flow rate of therapeutic gas to the injector module.

In a twenty-fifth embodiment, the therapeutic gas delivery system of the first through twenty-fourth embodiments may be modified in a manner wherein the therapeutic gas delivery system controller is configured to adjust the first primary high flow control valve in response to a value received from the first primary delivery flow sensor to adjust the flow rate of a therapeutic gas to an intended value.

Another aspect of the present invention relates to an electronically controlled gas blending device.

A first embodiment of the electronically controlled gas blending device comprises a flow control channel in fluid communication with a therapeutic gas supply, wherein the flow control channel comprises at least one secondary subsystem flow control valve, wherein the at least one secondary subsystem flow control valve is configured to be in communication over a communication path with a therapeutic gas delivery system controller, and at least one secondary subsystem flow sensor, wherein the at least one secondary subsystem flow sensor is in fluid communication with the at least one secondary subsystem flow control valve, and the at least one secondary subsystem flow sensor is configured to be in communication over a communication path with a therapeutic gas delivery system controller, one or more inlets configured to connect to a gas supply, one or more inlet flow sensors in fluid communication with at least one of the one or more inlets, a blending junction in fluid communication with the one or more inlet flow sensors, and the blending junction is connected to and in fluid communication with the flow control channel, and a therapeutic gas delivery system controller configured to be in electrical communication with at least the secondary subsystem flow control valve and the at least one secondary subsystem flow sensor to form a feedback loop, and configured to receive a flow value from the at least one inlet flow sensors and calculate a flow rate of therapeutic gas through the at least one secondary subsystem flow sensor to provide an intended dose of therapeutic gas exiting the blending junction.

In a second embodiment, the electronically controlled gas blending device of the first embodiment may be modified in a manner wherein the at least one secondary subsystem flow control valve and the at least one secondary subsystem flow sensor are arranged in series along the flow control channel.

In a third embodiment, the electronically controlled gas blending device of the first and/or second embodiments may be modified in a manner which further comprises a secondary subsystem shut-off valve in fluid communication with the flow control channel, and wherein the secondary subsystem shut-off valve is configured to have at least an open state and a closed state, and to be in communication over a communication path with a therapeutic gas delivery system controller.

In a fourth embodiment, the electronically controlled gas blending device of the first through third embodiments may be modified in a manner wherein there are two or more inlet flow sensors in fluid communication with at least one of the one or more inlets, and the therapeutic gas delivery system controller is configured to receive a flow value from at least two of the two or more inlet flow sensors, and compare the two values to determine if the two or more inlet flow sensors are providing the same flow value.

In a fifth embodiment, the electronically controlled gas blending device of the first through fourth embodiments may be modified in a manner wherein there are two or more secondary subsystem flow sensors in fluid communication with the at least one secondary subsystem flow control valve, and the therapeutic gas delivery system controller is configured to receive a flow value from at least two of the two or more secondary subsystem flow sensors, and compare the two values to determine if the two or more secondary subsystem flow sensors are providing about the same flow value.

In a sixth embodiment, the electronically controlled gas blending device of the first through fifth embodiments may be modified in a manner wherein the therapeutic gas delivery system controller is configured to generate an alarm signal if the flow values from the two of the two or more secondary subsystem flow sensors are not about the same.

In a seventh embodiment, the electronically controlled gas blending device of the first through sixth embodiments may be modified in a manner wherein the two or more inlet flow sensors are arranged in series with each other.

In an eighth embodiment, the electronically controlled gas blending device of the first through seventh embodiments may be modified in a manner which further comprises an outlet pressure sensor in fluid communication with the blending junction, and configured to be in communication over a communication path with the therapeutic gas delivery system controller, and the outlet pressure sensor communicates pressure values to the therapeutic gas delivery system controller, and the therapeutic gas delivery system controller is configured to detect pressure fluctuations in the outlet pressure sensor.

In a ninth embodiment, the electronically controlled gas blending device of the first through eighth embodiments may be modified in a manner which further comprises a flow regulating valve between and in fluid communication with the flow control channel and the blending junction, wherein the flow regulating valve is configured to direct a flow of therapeutic gas to either the blending junction or to an outlet.

In a tenth embodiment, the electronically controlled gas blending device of the first through ninth embodiments may be modified in a manner which further comprises an overpressure valve in fluid communication with the one or more inlet flow sensors and an external vent, wherein the overpressure valve is configured to open at a predetermined pressure to avoid pressure surges from the one or more inlets to the one or more inlet flow sensors.

In an eleventh embodiment, the electronically controlled gas blending device of the first through tenth embodiments may be modified in a manner wherein the therapeutic gas delivery system controller is configured to receive a signal indicating a failure of another flow control channel and communicate a signal to the secondary subsystem shut-off valve to transition from a closed state to an open state.

Another aspect of the present invention relates to a first embodiment of a therapeutic gas delivery system, comprising at least one gas supply subsystem, at least one primary gas delivery subsystem comprising at least one primary flow control channel, at least one secondary gas delivery subsystem comprising at least one secondary flow control channel comprising a secondary subsystem flow sensor, wherein the secondary subsystem flow sensor is in fluid communication with the secondary subsystem flow control valve, and where the secondary subsystem flow sensor is configured to be in communication over a communication path with a therapeutic gas delivery system controller, and a secondary subsystem flow control valve, wherein the secondary subsystem flow control valve is in fluid communication with the secondary subsystem shut-off valve, and the secondary subsystem shut-off valve and secondary subsystem flow control valve are arranged in series, and a therapeutic gas delivery system controller is configured to be in electrical communication with at least the secondary subsystem flow control valve and the secondary subsystem flow sensor to form a feedback loop.

In a second embodiment, the therapeutic gas delivery system of the first embodiment may be modified in a manner wherein the at least one primary gas delivery subsystem is controlled by a primary gas delivery subsystem controller, and the at least one secondary gas delivery subsystem is controlled separately by a secondary gas delivery subsystem controller.

In a third embodiment, the therapeutic gas delivery system of the first and/or second embodiments may be modified in a manner wherein the secondary gas delivery subsystem comprises a secondary subsystem shut-off valve, wherein the secondary subsystem shut-off valve is in fluid communication with the therapeutic gas supply and the secondary subsystem flow control valve, and is configured to have at least an open state and a closed state; and the therapeutic gas delivery system controller is configured to receive a failure signal from the at least one primary gas delivery subsystem, and communicate a signal to the secondary subsystem shut-off valve to transition from a closed state to an open state if a failure signal is received.

In a fourth embodiment, the therapeutic gas delivery system of the first through third embodiments may be modified in a manner wherein the therapeutic gas delivery system controller comprises a primary gas delivery system controller and a secondary gas delivery system controller, and the secondary gas delivery system controller is configured to communicate a signal to the secondary subsystem shut-off valve to transition from a closed state to an open state to avoid interruption of therapeutic gas flow from the therapeutic gas supply to a patient without input from a user if a failure of the primary gas delivery system controller is detected.

In a fifth embodiment, the therapeutic gas delivery system of the first through fourth embodiments may be modified in a manner which further comprises an outlet in fluid communication with the at least one primary gas delivery subsystem and the at least one secondary gas delivery subsystem, wherein the at least one secondary gas delivery subsystem is configured to deliver a therapeutic gas to the outlet in the event of a failure of the at least one primary gas delivery subsystem.

In a sixth embodiment, the therapeutic gas delivery system of the first through fifth embodiments may be modified in a manner which further comprises a breathing circuit comprising an injector module, wherein the injector module is configured to be in fluid communication with a respirator and the outlet, and secondary gas delivery subsystem is configured to deliver a therapeutic gas to the injector module at the dose of the primary gas delivery subsystem to avoid sudden changes in the dose of therapeutic gas.

In a seventh embodiment, the therapeutic gas delivery system of the first through sixth embodiments may be modified in a manner wherein the at least one primary gas delivery subsystem and the at least one secondary gas delivery subsystem are configured to provide a flow of therapeutic gas in parallel.

In an eighth embodiment, the therapeutic gas delivery system of the first through seventh embodiments may be modified in a manner wherein the at least one secondary gas delivery subsystem further comprises a flow regulating valve between and in fluid communication with the secondary flow control channel and a blending junction, wherein the flow regulating valve is configured to direct a flow of therapeutic gas to a low pressure outlet concurrently with flow of the therapeutic gas to the outlet from the primary gas delivery subsystem.

In a ninth embodiment, the therapeutic gas delivery system of the first through eighth embodiments may be modified in a manner wherein the flow regulating valve is configured to automatically direct a flow of therapeutic gas to the outlet of the primary gas delivery system in the event the primary gas delivery system fails.

In a tenth embodiment, the therapeutic gas delivery system of the first through ninth embodiments may be modified in a manner which further comprises at least one display, wherein the therapeutic gas delivery system controller is configured to provide an alarm on the at least one display to alert a user to the failure.

In an eleventh embodiment, the therapeutic gas delivery system of the first through tenth embodiments may be modified in a manner wherein the therapeutic gas delivery system is configured to provide a regulated dose of therapeutic gas to the outlet utilizing only one functioning gas supply subsystem and only one functioning flow control channel.

Another aspect of the present invention relates to another embodiment of an electronically controlled gas blending device, comprising a flow control channel in fluid communication with a therapeutic gas supply, wherein the flow control channel comprises at least one secondary subsystem flow control valve, wherein the at least one flow control valve is configured to be in communication over a communication path with a therapeutic gas delivery system controller, and at least two secondary subsystem flow sensors, wherein the at least two secondary subsystem flow sensors are in fluid communication with the at least one secondary subsystem flow control valve, and the at least two secondary subsystem flow sensors are configured to be in communication over a communication path with a therapeutic gas delivery system controller, wherein the at least one secondary subsystem flow control valve and the at least two secondary subsystem flow sensors are arranged in series along the flow control channel, one or more low pressure inlets configured to connect to a gas supply, comprising $O_2$ and/or air from a wall source and/or pressurized cylinder, two or more inlet flow sensors in fluid communication with at least one of the one or more low pressure inlets, wherein the two or more inlet flow sensors are arranged in series with each other, a blending junction in fluid communication with the two or more inlet flow sensors, and the blending junction is connected to and in fluid communication with the flow control channel, and a therapeutic gas delivery system controller comprising hardware, software, firmware, or a combination thereof, configured to be in electrical communication with at least the secondary subsystem flow control valve and the at least one of the two or more secondary subsystem flow sensors to form a feedback loop, and configured to receive a flow value from at least one of the two or more inlet flow sensors and calculate a flow rate of therapeutic gas through the two or more secondary subsystem flow sensors to provide an intended dose of therapeutic gas exiting a third leg of the blending junction.

In a second embodiment, the electronically controlled gas blending device may be modified in a manner wherein an external gas supply is in fluid communication with one of the one or more inlets and provides a flow of air and/or oxygen ($O_2$) to the two or more flow sensors in fluid communication with the one or more inlets.

Another aspect of the present invention relates to a method of confirming the proper functioning of a therapeutic gas delivery system.

A first embodiment relates to a method of confirming the proper functioning of a therapeutic gas delivery system, comprising pressurizing a gas supply subsystem at least between a gas source connection valve and a closed shut off to a pressure above atmospheric pressure, monitoring the pressure between the gas source connection valve and the closed shut off valve with a gas pressure sensor, and presenting an alarm if the pressure between the gas source connection valve and the closed shut off valve decreases over the predetermined time period.

In a second embodiment, the method of confirming the proper functioning of a therapeutic gas delivery system of the first embodiment may be modified in a manner which further comprises which further comprises mating a therapeutic gas source to a gas source coupling, and opening a purge valve in fluid communication with the gas source connection valve, and between the closed shut off and the gas source connection valve to flush gas within the gas supply subsystem with gas from the mated therapeutic gas source.

In a third embodiment, the method of confirming the proper functioning of a therapeutic gas delivery system of the first and/or second embodiments may be modified in a manner which further comprises mating a therapeutic gas source to a gas source coupling, and opening the shut off to deliver a flow of therapeutic gas from the gas supply subsystem to at least one of the one or more flow control channels comprising at least one shut off valve, at least one delivery flow sensor, and at least one confirmatory flow sensor to purge the gas supply subsystem and the at least one of the one or more flow control channels.

In a fourth embodiment, the method of the first through third embodiments may be modified in a manner which further comprises reading a gas source identifier attached to the therapeutic gas source with a gas source identifier reader, wherein the gas source identifier contains information at least of the identity, expiration date, and the concentration of the therapeutic gas supplied by the therapeutic gas source.

In a fifth embodiment, the method of the first through fourth embodiments may be modified in a manner which further comprises selectively opening the shut off valve for one of the one or more flow control channels, while the shut off valve for each of any other of the one or more flow control channels is closed; and measuring the gas flow rate through the at least one delivery flow sensor, and the at least one confirmatory flow sensor of the one flow control channel.

In a sixth embodiment, the method of the first through fifth embodiments may be modified in a manner which further comprises sequentially opening the shut off valve for each of the other of the one or more flow control channels by selectively opening the shut off valve for the next flow control channel, and closing the shut off valve of the previous flow control channel.

In a seventh embodiment, the method of the first through sixth embodiments may be modified in a manner which further comprises comparing the gas flow rate through the at least one delivery flow sensor with the gas flow rate through the at least one confirmatory flow sensor of the one flow control channel; and presenting an alarm if there is a discrepancy between the gas flow rate through the at least one delivery flow sensor and the gas flow rate through the at least one confirmatory flow sensor.

Another aspect of the invention relates to a method of confirming the proper functioning of gas delivery subsystem and injection module operation.

A first embodiment relates to a method of confirming the proper functioning of gas delivery and injection module operation, comprising receiving an injection module at an outlet port, providing a flow of breathing gas at an inlet port at a breathing gas flow rate, wherein the inlet port is in fluid communication with the outlet port, measuring the breathing gas flow rate from the gas supply at a delivery flow sensor and at a confirmatory flow sensor, wherein the delivery flow sensor and the confirmatory flow sensor are in fluid communication with the inlet port and the outlet port, measuring the breathing gas flow rate from the gas supply at an injection module delivery flow sensor and an injection module confirmatory flow sensor, wherein the injection module delivery flow sensor and the injection module confirmatory flow sensor are in fluid communication with the outlet port, and determining if one of the breathing gas flow rates measured at the confirmatory flow sensor, the delivery flow sensor, the injection module confirmatory flow sensor, or the injection module delivery flow sensor differs from the other measured breathing gas flow rates by greater than a threshold amount.

In a second embodiment, the method of confirming the proper functioning of gas delivery and injection module operation of the first embodiment may be modified in a manner which further comprises providing an alarm if the breathing gas flow rates measured at the low pressure confirmatory flow sensor, the low pressure delivery flow sensor, the injection module confirmatory flow sensor, or the injection module delivery flow sensor differs from the other measured breathing gas flow rates by greater than a threshold amount.

In a third embodiment, the method of confirming the proper functioning of gas delivery and injection module operation of the first and/or second embodiments may be modified in a manner wherein the threshold amount is about 10%.

In a fourth embodiment, the method of confirming the proper functioning of gas delivery and injection module operation of the first through third embodiments may be modified in a manner wherein the low pressure delivery flow sensor and the low pressure confirmatory flow sensor are arranged in series, and wherein the injection module delivery flow sensor and the injection module confirmatory flow sensor are arranged in series.

In a fifth embodiment, the method of confirming the proper functioning of gas delivery and injection module operation of the first through fourth embodiments may be modified in a manner wherein the injection module delivery flow sensor and the injection module confirmatory flow sensor are bi-directional flow sensors that are configured to determine the direction of gas flow through the injection module.

In a sixth embodiment, the method of confirming the proper functioning of gas delivery and injection module operation of the first through fifth embodiments may be modified in a manner wherein the low pressure gas supply comprises a wall supply and/or a pressurized cylinder configured to provide air, oxygen, or a combination thereof.

In a seventh embodiment, the method of confirming the proper functioning of gas delivery and injection module operation of the first through sixth embodiments may be modified in a manner which further comprises providing a stream of therapeutic gas to the flow of breathing gas upstream from an output of the injection module, wherein the stream of therapeutic gas and breathing gas combine to provide an intended concentration of therapeutic gas.

In an eighth embodiment, the method of confirming the proper functioning of gas delivery and injection module operation of the first through seventh embodiments may be modified in a manner which further comprises connecting a sampling line down stream from the output of the injection module to sample at least a portion of the flow of gas exiting the injection module to a gas analyzer for measurement of at least the concentration of therapeutic gas, determining the concentration of therapeutic gas exiting the injection module, and comparing the measured concentration of therapeutic gas with the intended concentration of therapeutic gas.

In a ninth embodiment, the method of confirming the proper functioning of gas delivery and injection module operation of the first through eighth embodiments may be modified in a manner which further comprises adjusting a subsystem flow control valve to provide a stream of therapeutic gas at an intended therapeutic gas flow rate; and determining if the subsystem flow control valve is properly functioning, wherein the subsystem flow control valve is in fluid communication with the low pressure outlet port.

In a tenth embodiment, the method of confirming the proper functioning of gas delivery and injection module operation of the first through ninth embodiments may be modified in a manner which further comprises measuring the combined therapeutic gas flow rate and breathing gas flow rate at the injection module delivery flow sensor and the injection module confirmatory flow sensor, switching a flow regulating valve to divert the stream of therapeutic gas to an alternative flow path, wherein the flow regulating valve is up stream from and in fluid communication with the low pressure outlet port, and the subsystem flow control valve is upstream from and in fluid communication with the flow regulating valve, measuring the breathing gas flow rate at the injection module delivery flow sensor and the injection module confirmatory flow sensor, and determining if the flow regulating valve functioned properly by determining if the combined therapeutic gas flow rate and breathing gas flow rate decreased by the therapeutic gas flow rate when the flow regulating valve was switched to the alternative flow path.

In an eleventh embodiment, the method of confirming the proper functioning of gas delivery and injection module operation of the first through tenth embodiments may be modified in a manner which further comprises measuring a flow rate at two or more subsystem flow sensors, wherein the two or more subsystem flow sensors are upstream from and in fluid communication with the three-way valve; and comparing the flow rates measured at each of the two or more subsystem flow sensors to determine if the two or more subsystem flow sensors are in agreement.

In a twelfth embodiment, the method of confirming the proper functioning of gas delivery and injection module operation of the first through eleventh embodiments may be modified in a manner which further comprises calculating therapeutic gas blending ratio from the measured flow rate measured by at least one of the two or more subsystem flow sensors and from the breathing gas flow rate measured by the low pressure delivery flow sensor; and comparing the calculated therapeutic gas blending ratio to the measured concentration of therapeutic gas exiting the injection module.

In a thirteenth embodiment, the method of confirming the proper functioning of gas delivery and injection module operation of the first through twelfth embodiments may be modified in a manner which further comprises adjusting a subsystem flow control valve to be completely open to provide the stream of therapeutic gas at a maximum therapeutic gas flow rate.

Another aspect of the invention relates to a method to ensure the proper functioning of a therapeutic gas delivery system.

A first embodiment relates to a method to ensure the proper functioning of a therapeutic gas delivery system, comprising detecting a therapeutic gas source mated with a therapeutic gas supply subsystem, providing an initial purge of the therapeutic gas supply subsystem with gas from the therapeutic gas source, determining if the initial purge was successful, maintaining a shutoff valve down stream from the therapeutic gas source in a closed state, verifying that no flow is detected by one or more flow sensors down stream from the shutoff valve, and determining if flow is detected by one or more flow sensors down stream from the shutoff valve; and providing an alert if it is determined that the initial purge was not successful and/or if flow is detected by one or more flow sensors down stream from the shutoff valve.

In a second embodiment, the method to ensure the proper functioning of a therapeutic gas delivery system of the first embodiment may be modified in a manner which further comprises reading information associated with the therapeutic gas source to determine the identity, concentration, and/or expiration date of the therapeutic gas source, and verifying the therapeutic gas source mated with a therapeutic gas supply subsystem has the correct identity, concentration, and/or expiration date.

In a third embodiment, the method to ensure the proper functioning of a therapeutic gas delivery system of the first and/or second embodiments may be modified in a manner wherein the shutoff valve down stream from the therapeutic gas source in a closed state until the correct identity, concentration, and/or expiration date is verified.

The systems and methods may further comprise an alarm system to inform the user when a therapeutic gas source has reached a predetermined minimum run-time-to-empty. In various systems in which multiple therapy gas sources are engaged, the alarm system may also inform the user with a high-priority alarm when the total run-time-to-empty of the system has been reached.

BRIEF DESCRIPTION OF THE DRAWINGS

The features and advantages of the present invention will be more fully understood with reference to the following, detailed description when taken in conjunction with the accompanying figures, wherein.

DETAILED DESCRIPTION

Figure 1:
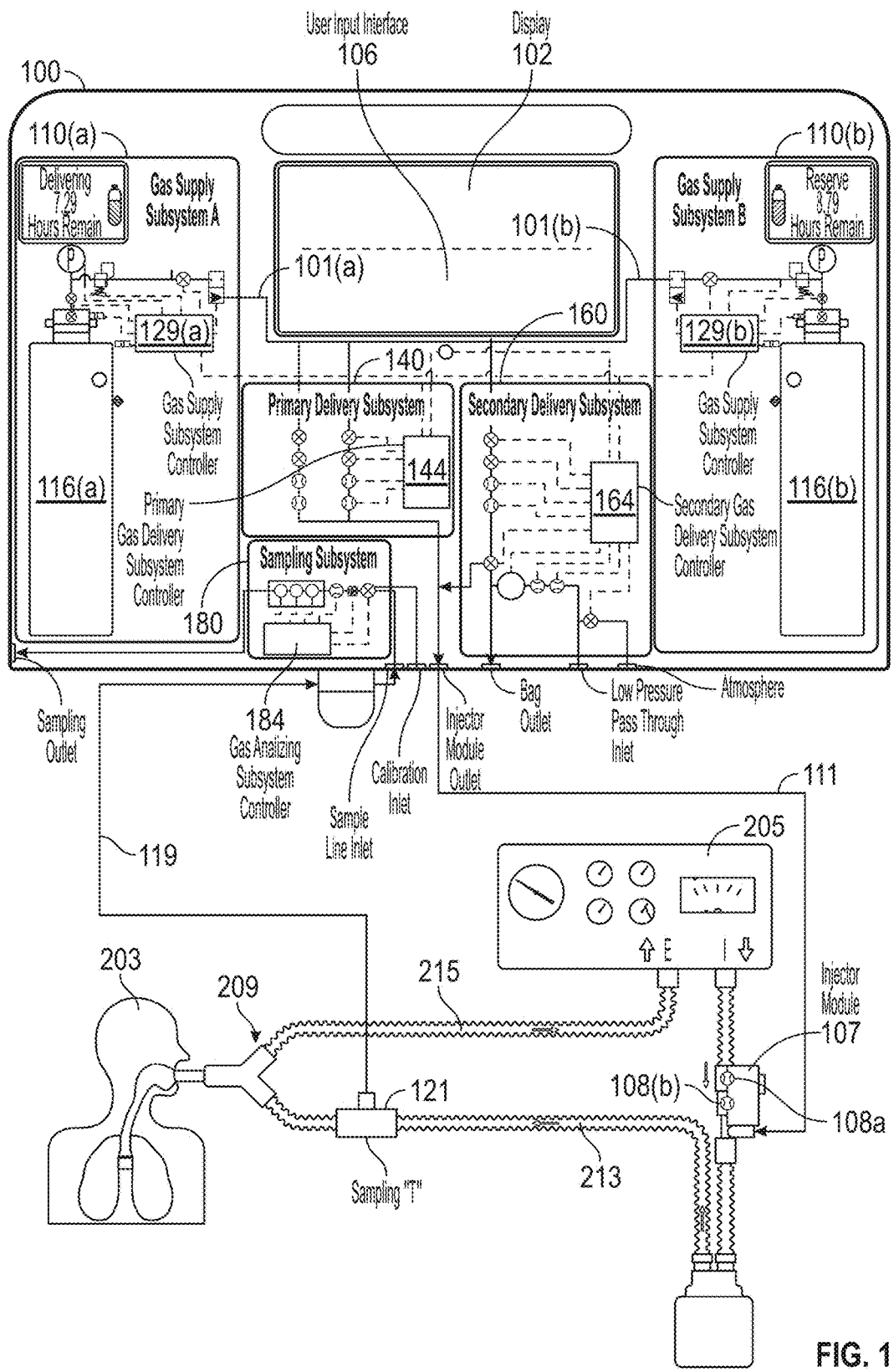
FIG. 1 is an overview diagram of an exemplary therapeutic gas delivery system and patient breathing apparatus, in accordance with exemplary embodiments of the present invention.

In exemplary embodiments, systems and methods of the present invention provide enhanced safety improvements over current therapeutic gas delivery systems by at least enabling accurate and/or precise determination and/or usage of information indicative of the run-time-to-empty for the therapeutic gas source. In exemplary embodiments, a plurality of therapeutic gas sources can be affiliated with a therapeutic gas delivery system. Further, in at least some instances, the present invention can determine and/or use information indicative of the run-time-to-empty for a plurality of therapeutic gas sources affiliated with a therapeutic gas delivery system.

In exemplary embodiments, therapeutic gas delivery systems of the present invention can comprise at least one gas supply subsystem, at least one primary delivery subsystem, and/or at least one secondary delivery subsystem, wherein redundant systems and/or components provide parallel or supplemental data enabling cross verification of component operation, fallback functionality, and/or fail-safe protection of the patient and the system. In at least some embodiments, the present invention can provide simplified therapeutic gas delivery systems and methods of fail-safe protection and redundancy that can allow seamless transition to backup systems automatically, for example, without the need of extensive training of a user. Further, in exemplary embodiments, the present invention can mitigate risks associated with sudden termination of inhaled therapeutic gas delivery and/or incorrect delivery of therapy.

In one or more embodiments, therapeutic gas delivery systems of the present invention can comprise, amongst other things, at least one gas supply subsystem as well as at least one least one gas delivery subsystem. For example, therapeutic gas delivery systems of the present invention can comprise at least one gas supply subsystem and at least one delivery subsystem comprising at least one flow control channel, wherein the gas supply subsystem provides a first therapeutic gas source having a volume and/or containing a therapeutic gas at an initial pressure for delivery to a patient. For another example, therapeutic gas delivery systems of the present invention can comprise two or more gas supply subsystems, a primary delivery subsystem having at least one flow control channel comprising a plurality of valves and a plurality of flow sensors, and a secondary delivery subsystem having at least one flow control channel comprising a plurality of valves and a plurality of flow sensors, wherein the two or more gas supply subsystems provide a first therapeutic gas source having a volume and/or containing a therapeutic gas at an initial pressure for initial delivery of therapeutic gas to a patient, and at least a second therapeutic gas source having a volume and/or containing a therapeutic gas at an initial pressure for subsequent delivery of therapeutic gas to a patient when the pressure within the first therapeutic gas source falls below a predetermined, threshold value.

In various embodiments, the primary delivery subsystem and/or the secondary delivery subsystem control the flow rate of therapeutic gas to achieve the set dose being delivered to a patient in need of the therapeutic gas, and, in at least some instances, the therapeutic gas may be blended with air and/or oxygen before being received by the patient.

In exemplary embodiments, systems and methods can determine the length of time that a therapeutic gas source can continue delivering the therapeutic gas before having insufficient pressure/gas volume, also referred to as "run-time-to-empty", for example, by calculating the volume and pressure of therapeutic gas available from the therapeutic gas source, for example by using the ideal gas law, and the rate at which the therapeutic gas is flowing from the therapeutic gas source. As used herein, "run-time-to-empty", "RTE", or the like means the estimated time a therapeutic gas source can continue to supply the therapeutic gas at a current flow rate until the pressure remaining in the therapeutic gas source reaches a threshold value at which the ability to control or maintain the flow rate may be affected.

In one or more embodiments, a therapeutic gas delivery system comprising two or more therapeutic gas sources may first supply therapeutic gas from the therapeutic gas source having the shorter run-time-to-empty value and/or minimum run-time pressure. In various embodiments, the therapeutic gas delivery system may seamlessly transition from a first therapeutic gas source to a second therapeutic gas source when the first therapeutic gas source has reached the intended run-time-to-empty value and/or minimum run-time pressure. For example, systems and methods can enable source gas cut-over (e.g., seamless transition) between at least two source gases (e.g., therapeutic gas being received for delivery from one gas source can be halted such that the therapeutic gas can be received for delivery from another gas source) when run-time-to-empty for a therapeutic gas source is below a minimum threshold and/or when desired. In one or more embodiments, cut-over may be accomplished without any interruption of therapeutic gas flow, where cut-over may involve controller actuated opening of a flow path to a subsequent therapeutic gas source before closing, immediately after closing, and/or in parallel with closing the flow path to the initial therapeutic gas source to avoid sudden interruption of gas inhalation therapy, which may also be referred to as "seamless transition." In at least some embodiments, usage of the therapeutic gas source may not be allowed if the source does not have a minimum run-time pressure (e.g., pressure below 300 psi, not enough pressure to perform purges, pressure low or waning indicative of leak, etc.).

In various embodiments, the therapeutic gas source having the shorter run-time-to-empty value is used first to provide sufficient time to replace the exhausted therapeutic gas source before the second therapeutic gas source may become exhausted. In various embodiments, a user may be alerted to the run-time-to-empty value, a need to switch over to another therapeutic gas source, and/or the need to replace an effectively empty therapeutic gas source, for example, after switch-over to a second therapeutic gas source provided as a backup to avoid sudden discontinuation of the therapeutic inhalation therapy. In embodiments wherein the therapeutic gas delivery system is configured to engage multiple therapeutic gas sources, the program or algorithm incorporates the number of therapeutic gas sources connected to the system into the run-time-to-empty calculation. For example, run-time-to empty is calculated in the manner described above for each connected therapeutic gas source and the program or algorithm uses this data to calculate a total run-time-to-empty for the therapeutic gas delivery system for use of each therapeutic gas source sequentially. Sequential use of multiple therapeutic gas sources connected to the therapeutic gas delivery system means that a first therapeutic gas source is in fluid communication with the therapeutic gas supply system and at least a second therapeutic gas source is connected to another therapeutic gas supply system, but is shut off from fluid communication to one or more therapeutic gas delivery system(s).

Principles and embodiments or the present invention also relate to algorithms to obtain values from sensor(s), valve(s), regulator(s), and/or detector(s), and perform the calculations of run-time-to-empty based on the obtained values. In various embodiments, values may be communicated from sensors, valves, regulators, and/or detectors, to the therapeutic gas delivery system controller, where the value may be communicated as an analog or digital signal over a communication path that may be wired or wireless. In various embodiments, a value may be electrically communicated as an analog current and/or voltage, or as a digital sequence that is representative of the value, where the therapeutic gas delivery system controller may be configured to receive, interpret, and/or store the value, for example with A-to-D converters, buffers, direct memory access (DMA), as well as other hardware, software, and/or firmware that is known in the art.

In exemplary embodiments, an algorithm can determine the run-time-to empty (RTE) using gas pressure information, therapeutic gas source volume information, temperature information, and equations. RTE can be calculated by a therapeutic gas delivery system controller with information generated from using (i) Delivery NO flow sensors, (ii) Redundant (monitoring) flow sensors, (iii) Commands/Settings to NO control valve, (iv) Set dose+Injector module (IM) flow sensor reading (delivery or redundant monitoring flow sensor); and/or (v) Gas source contents pressure sensing.

In exemplary embodiments, RTE can account for (i) Purging (current and future) using therapeutic gas; (ii) System level leaks determined by high pressure or lower (32) pressure decay test; (iii) Residual pressure intended to be left in gas source (gas source not emptied completely); (iv) Concurrent delivery—secondary and Primary running at same time; (v) temperature (e.g., temperature changes may result in changes in pressure, etc.); (vii) filtering (e.g., undesired oscillating values may be filtered, RTE displayed may filter out oscillations, (vi) RTE life extension can immediately update upon changes in set dose; and/or (vii) Improved RTE accuracy with ambient temperature correction.

In one or more embodiments, run-time-to empty information and/or alarms can be provided to users of the therapeutic gas delivery system for one or more of the therapeutic gas sources. In various embodiments, run-time-to empty information and/or alarms may be displayed on a display screen affiliated with one of the one or more gas supply subsystems. In various embodiments, a separate display screen may be affiliated with each of the two or more gas supply subsystems, where each of the displays may be configured to present run-time-to empty information and/or alarms to a user.

Principles and embodiments of the present invention also generally relate to a therapeutic gas delivery system comprising automatic back-up systems that provide simple and easy to use therapeutic gas delivery in the event of failure of a primary gas delivery system, where a back-up system for manual ventilation (e.g., bagging, external manual ventilation device, assisted breathing apparatus, etc.) is sufficiently automated and simple to be utilized by personnel that are otherwise untrained on therapeutic gas delivery systems. In one or more embodiments, a therapeutic gas blending system is configured to provide a controlled gas flow rate to an external manual ventilation device (e.g., bag valve mask) for providing the same set dose to allow a patient to remain ventilated without discontinuation of inhalation therapy.

Delivery and Sampling System Overview

Figure 2:
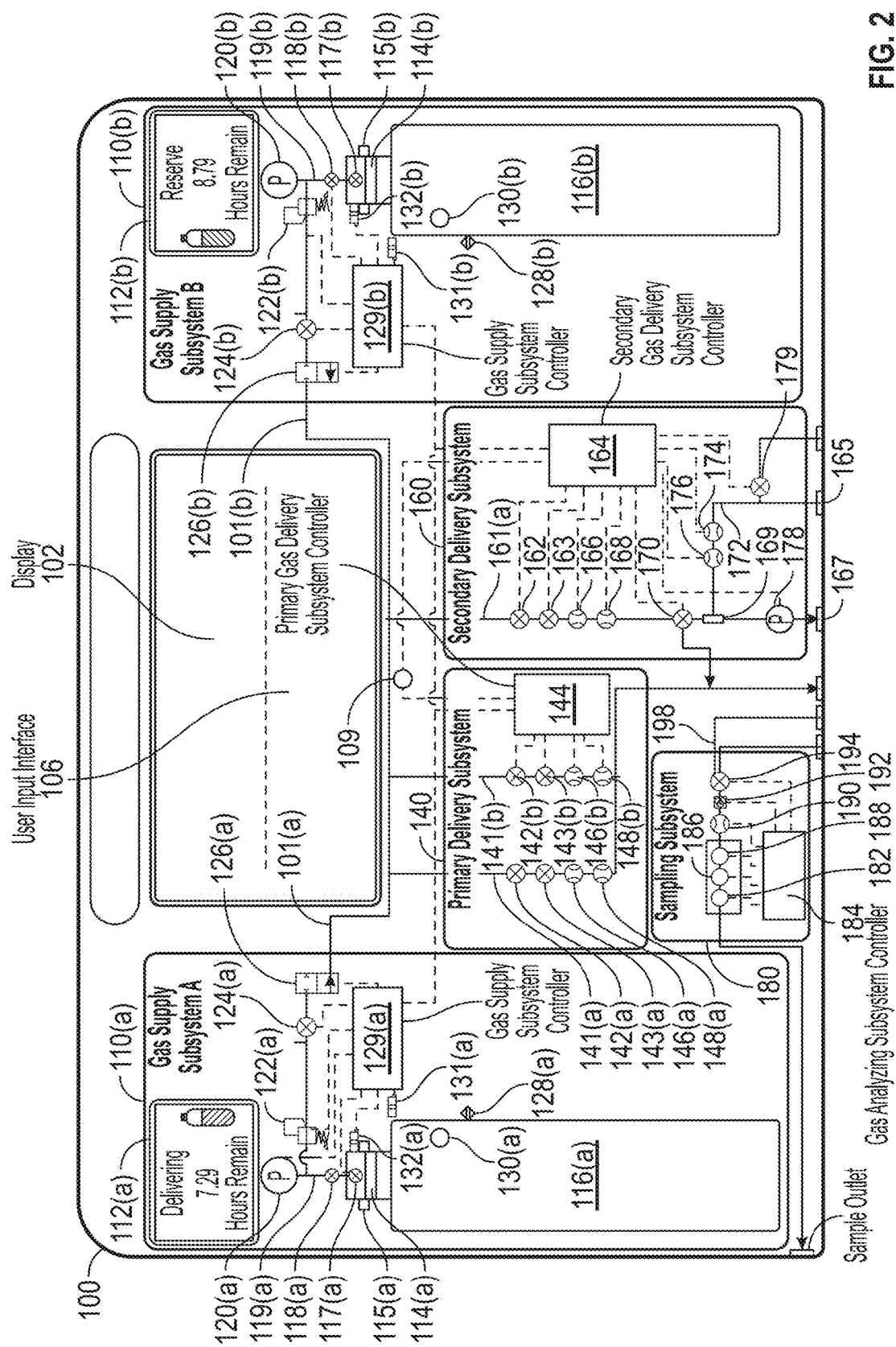
FIG. 2 is a diagram of the exemplary therapeutic gas delivery system, in accordance with exemplary embodiments of the present invention.
Figure 3:
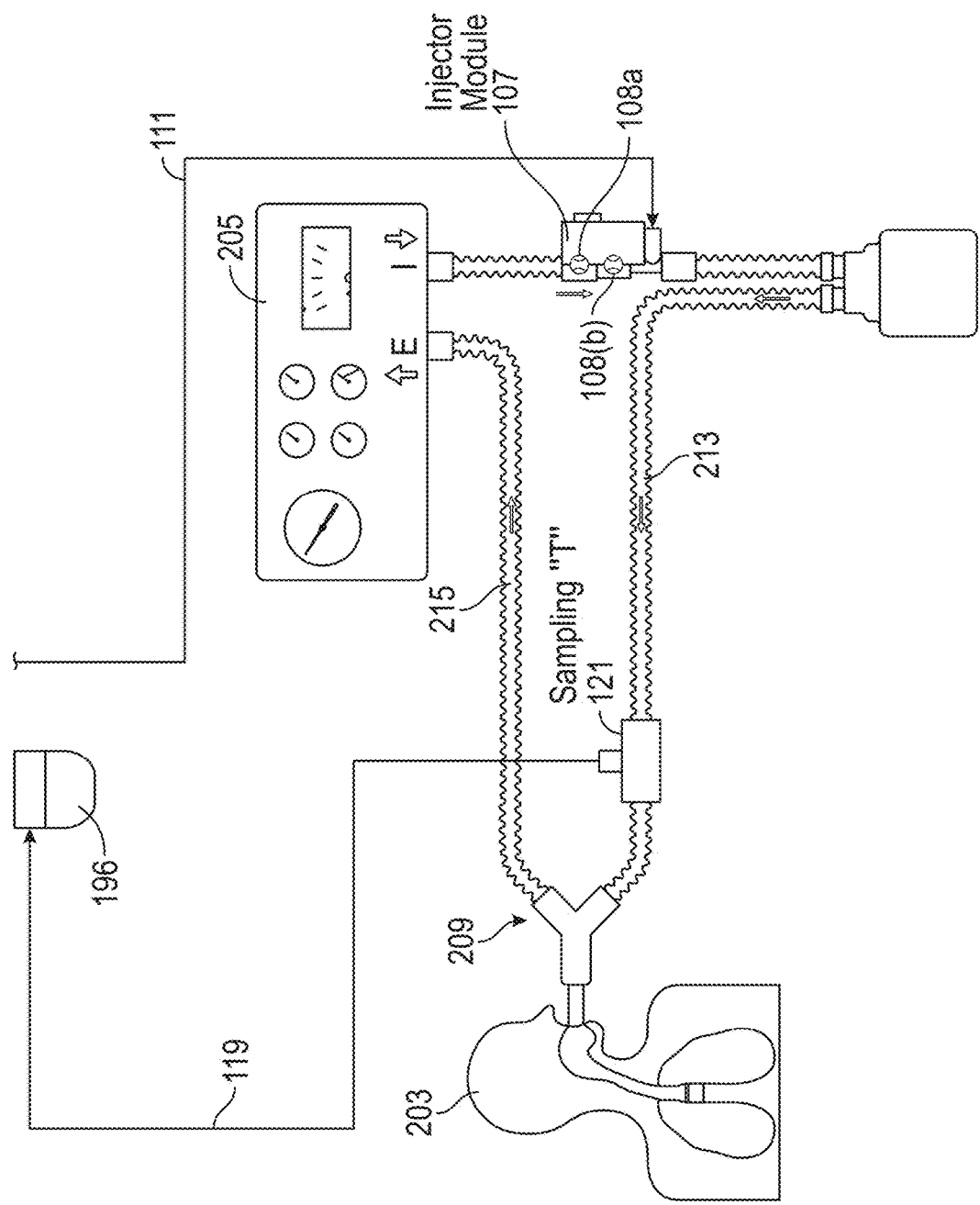
FIG. 3 is a diagram of the portion of the exemplary therapeutic gas delivery system downstream of FIG. 2 and/or which couples to the patient breathing apparatus, in accordance with exemplary embodiments of the present invention.

Referring to FIGS. 1-3, an exemplary system for delivering inhaled therapeutic nitric oxide gas (NO) to a patient is illustratively depicted. It will be understood that systems and methods of the present invention can use, modify, and/or be affiliated with any applicable system for delivering therapeutic gas to a patient. For example, systems and methods of the present invention can use, modify, and/or be affiliated with the delivery systems and/or other teachings of U.S. Pat. No. 5,558,083 entitled "NO Delivery System" and/or U.S. Pat. No. 5,752,504 entitled "System for Monitoring Therapy During Calibration", the contents of both of which are incorporated herein by reference in their entireties.

Systems and methods are, at times, described as being directed towards inhaled nitric oxide (NO). This is merely for ease and is in no way meant to be a limitation. Of course the teachings disclosed herein can, when appropriate, be used for other therapeutic gas, such as, but not limited to, carbon monoxide (CO), hydrogen sulfide ($H_2S$), etc. Further, therapeutic gas can be supplied from one or more therapeutic gas sources that can be any source of therapeutic gas such as a therapeutic gas contained in a cylinder (e.g., a cylinder containing NO, $H_2S$), NO gas generator, or the like. Of course other sources of therapeutic gas can be used. For ease, at times, the therapeutic gas source is described as a cylinder, NO cylinder, and the like. This is merely for ease and is in no way meant to be a limitation.

In exemplary embodiments, a therapeutic gas delivery system 100 can be used to deliver therapeutic gas, such as NO, to a patient 203 who may be using an assisted breathing apparatus such as a ventilator 205 or other device used to introduce therapeutic gas to the patient, for example, a nasal cannula, endotracheal tube, face mask, bag valve mask, or the like. For ease, systems and methods of the present invention are described, at times, as being for use with a ventilator. This is merely for ease and is in no way meant to be a limitation. For example, for at least a ventilated patient 203, ventilator 205 can deliver breathing gas to patient 203 via inspiratory limb 213 of patient breathing circuit 209, while patient expiration can flow via an expiratory limb 215 of patient breathing circuit 209, at times, to ventilator 205. Of course other ventilator types are envisioned. For example, a single limb ventilator type system is envisioned that may have a combined inspiratory and expiratory limb.

In exemplary embodiments, systems and methods of the present invention can be used to wild stream blend therapeutic gas with inspiratory flow (e.g., provided from a ventilator, provided from an air and/or oxygen source, etc.). By way of example, described below in more detail, wild stream blending can be accomplished with an injector module 107 coupled to inspiratory limb 213 of breathing circuit 209 enabling NO to be delivered from therapeutic gas delivery system 100 and/or any subsystem (e.g., primary gas delivery subsystem, secondary gas delivery system, etc.) to injector module 107, via delivery conduit 111. This NO can then be delivered, via injector module 107, into inspiratory limb 213 of patient breathing circuit 209 affiliated with ventilator 205 being used to deliver breathing gas to a patient 203. By way of another example, described below in more detail, wild stream blending can be accomplished by blending NO with air and/or oxygen provided from a wall outlet (e.g., high pressure air and/or oxygen that may be provided from a wall outlet in a hospital or cylinder supply, low pressure air and/or oxygen that may be provided from a regulator that may receive air and/or oxygen from a wall outlet in a hospital, gas compressor outlet, etc.). In at least some instances, wild stream blending (e.g., NO with air and/or oxygen provided from a wall outlet) can occur within system 100. In exemplary embodiments, wild stream blending can occur internally within system 100 and/or external of system 100, for example, at injector module 107.

As used herein, "wild stream blended proportional", "wild stream blending", "ratio metric blending", and the like, relates to stream blending, where the main flow stream is an uncontrolled (unregulated) stream that is referred to as the wild stream, and the component being introduced into the wild stream is controlled as a proportion of the main stream, which may typically be blended upstream (or alternatively downstream) of the main stream flowmeter. In various embodiments, the inspiratory flow may be the "wild stream" as the flow (e.g., from the ventilator) is not specifically regulated or controlled by the therapeutic gas delivery system, and the nitric oxide is the blend component, for example, that may be delivered as a proportion of the inspiratory flow through the delivery line and/or conduit 111.

In exemplary embodiments, to at least wild stream blend NO, injector module 107 can be affiliated with at least one flow sensor capable of measuring the mass and/or volume flow rate(s) of at least patient breathing gas in the inspiratory line of the patient breathing circuit. For example, injector module 107 can include one or more breathing circuit gas (BCG) flow sensors 108(a) and/or 108(b) that can measure and communicate to the NO delivery system and/or any subsystem (e.g. primary delivery subsystem, secondary delivery subsystem, etc.) the mass and/or volume flow rate(s) of at least patient breathing gas in the inspiratory line of the breathing circuit passing through injector module 107, and in turn to patient 203. BCG flow sensors may be bi-directional. BCG sensors may also operate via differential pressure measurements. Although shown as being at injector module 107, BCG flow sensors 108(a) and/or 108(b) can be placed elsewhere in the inspiratory limb 213, such as upstream of the injector module 107. Also, instead of receiving flow information from BCG flow sensors 108(a) and/or 108(b), the delivery system may receive flow information directly from the source of inspiratory flow (e.g., ventilator 205, high pressure air and/or oxygen that may be provided from a wall outlet in a hospital, low pressure air and/or oxygen that may be provided from a regulator that may receive air and/or oxygen from a wall outlet in a hospital, etc.) indicative of the flow of breathing gas from the source of inspiratory flow (e.g., ventilator 205, high pressure air and/or oxygen that may be provided from a wall outlet in a hospital, low pressure air and/or oxygen that may be provided from a regulator that may receive air and/or oxygen from a wall outlet in a hospital, etc.).

Therapeutic gas delivery system 100 can include, amongst other things, a first gas supply subsystem 110(a), a second gas supply subsystem 110(b), a primary gas delivery subsystem 140, a secondary gas delivery subsystem 160, and/or a gas analyzing subsystem 180. Therapeutic gas delivery system 100 can also include user interfaces such as display(s) 102 and/or user input interface(s) 106. Further, first gas supply subsystem 110(a) can have user interfaces such as display 112(a) and/or second gas supply subsystem 110(b) can have user interfaces such as display 112(b). Any of the user interfaces can include, but is not limited to buttons, keyboards, knobs, and/or touchscreens, to name a few and/or user input interfaces and/or displays can be combined such that information can be input by users and/or communicated to users. By way of example, user input interface 102, 106 and/or displays 112(a), 112(b) can receive and/or provide information indicative of desired settings from the user, such as, but not limited to, the patient's prescription (in mg/kg ideal body weight, mg/kg/hr, mg/kg/breath, mL/breath, gas source concentration, delivery concentration or set dose, duration, etc.), the patient's age, height, sex, weight, etc. User input interface 102, 106 and/or display 112(a), 112(b) may be configured in at least some instances be used to confirm the desired patient dosing (e.g., user input desired dose of NO PPM) using a gas sampling subsystem 180, as described in greater detail below. In various embodiments, the therapeutic gas delivery system 100 may be in communication with the medical facility's (e.g., hospital) patient information system, where the patient's information and/or prescription can be directly communicated from the patient information system to the therapeutic gas delivery system 100.

It will be understood that any of the elements of system 100 can be combined and/or further separated. For ease elements are, at times, described as being specific to subsystems. This is merely for ease and is in no way meant to be a limitation. Further, information communication paths are, at times, illustrated as dashed lines and/or fluid communication conduits are, at times, illustrated as solid lines. This is merely for ease and is in no way meant to be a limitation.

To at least deliver desired set doses of therapeutic gas to a patient, sample therapeutic gas being delivered to a patient, and/or perform other methods and operations, therapeutic gas delivery system 100 can include a system controller (not shown) and/or subsystems can include subsystem controllers such as, but not limited to, gas supply subsystem controller 129(a), gas supply subsystem controller 129(b), primary gas delivery subsystem controller 144, a secondary gas delivery subsystem controller 164, and/or a gas analyzing subsystem(s) controller 184. The system controller and/or any of the subsystem controllers may comprise one or more processors (e.g., CPUs) and memory, where the system controller and/or any of the subsystem controllers may comprise, for example, a computer system, a single board computer, one or more application-specific integrated circuits (ASICs), or a combination thereof. Processors can be coupled to memory and may be one or more of readily available memory such as random access memory (RAM), read only memory (ROM), flash memory, compact/optical disc storage, hard disk, or any other form of local or remote digital storage. Support circuits can be coupled to processors, to support processors, sensors, valves, analyzing systems, delivery systems, user inputs, displays, injector modules, breathing apparatus, etc. in a conventional manner. These circuits can include cache memory, power supplies, clock circuits, input/output circuitry, analog-to-digital and/or digital-to-analog convertors, subsystems, power controllers, signal conditioners, and the like. Processors and/or memory can be in communication with sensors, valves, analyzing systems, delivery systems, user inputs, displays, injector modules, breathing apparatuses, etc. Communication to and from the system controller may be over a communication path, where the communication path may be wired or wireless, and wherein suitable hardware, firmware, and/or software may be configured to interconnect components and/or provide electrical communications over the communication path(s).

In various embodiments, primary gas delivery subsystem controller 144 and secondary gas delivery subsystem controller 164 may be redundant controllers with duplicate hardware, software and/or firmware (e.g., architected to function with redundancies, etc.), where each subsystem controller can perform the operations of the other subsystem controller and take over in the event of a failure. In various embodiments, therapeutic gas delivery system controller comprises primary gas delivery subsystem controller 144 and secondary gas delivery subsystem controller 164, where primary gas delivery subsystem controller 144 and/or secondary gas delivery subsystem controller 164 may be master controllers and gas supply subsystem controller 129(a) and/or gas supply subsystem controller 129(b) may be slave controllers. In various embodiments, gas analyzer subsystem controller 184 may be a slave controller under primary gas delivery subsystem controller 144 and/or secondary gas delivery subsystem controller 164. Of course, other master slave configurations are and/or other controller configurations are envisioned.

In various embodiments, the therapeutic gas delivery system controller can comprise, but is not limited to, at least one of four subsystem controllers 144, 164, 129(a), and/or 129(b). In exemplary embodiments, each subsystem controller for each subsystem is in electrical communication with components of that subsystem, components of other subsystems and/or any other components affiliated with system 100.

For example, subsystem controller 129(a) can be in electrical communication with the components of a first gas supply subsystem 110(a) (e.g., received therapeutic gas source 116(a), therapeutic gas source valve 117(a), gas source connection valve 118(a), gas pressure sensor 120(a), pressure regulator 122(a), purge valve 124(a), shut off 126(a), gas source identifier 128(a), temperature sensor 130(a), gas source identifier reader 131(a), and/or gas source detector 132(a), etc.), and/or components of another subsystem such as second gas supply subsystem 110(b) (e.g., received therapeutic gas source 116(b), therapeutic gas source valve 117(b), gas source connection valve 118(b), gas pressure sensor 120(b), pressure regulator 122(b), purge valve 124(b), shut off 126(b), gas source identifier 128(b), temperature sensor 130(b), gas source identifier reader 131(b), and/or gas source detector 132(b), etc.), primary gas delivery subsystem 140 (e.g., first primary shut off valve 142(a), first primary high flow control valve 143(a), first primary delivery flow sensor 146(a), first primary confirmatory flow sensor 148(a), second primary shut off valve 142(b), second primary high flow control valve 143(b), second primary delivery flow sensor 146(b), and/or second primary confirmatory flow sensor 148(b), etc.), secondary gas delivery subsystem 160 (e.g., secondary shut off valve 162, secondary medium flow control valve 163, secondary delivery flow sensor 166, and/or a secondary confirmatory flow sensor 168, flow regulating valve 170, low pressure oxygen/air received flow sensor 174, low pressure oxygen/air received confirmatory flow sensor 176, low pressure oxygen/air received pressure sensor 178, and/or overpressure valve 179, etc.), gas analyzing subsystem(s) 180 (e.g., gas sensor 182, gas sensor 186, gas sensor 188, sample gas flow sensor 190; sample pump 192; and/or sample system valve(s) 194, etc.), and/or any other components affiliated with system 100 (e.g., injector module delivery flow sensor 108(a), injector module confirmatory flow sensor 108(b)).

For another example, subsystem controllers 129(b) is in electrical communication with the components of a second gas supply subsystem 110(b) (e.g., received therapeutic gas source 116(b), therapeutic gas source valve 117(b), gas source connection valve 118(b), gas pressure sensor 120(b), pressure regulator 122(b), purge valve 124(b), shut off 126(b), gas source identifier 128(b), temperature sensor 130(b), gas source identifier reader 131(b), and/or gas source detector 132(b), etc.), and/or components of another subsystem such as second gas supply subsystem 110(a) (e.g., received therapeutic gas source 116(a), therapeutic gas source valve 117(a), gas source connection valve 118(a), gas pressure sensor 120(a), pressure regulator 122(a), purge valve 124(a), shut off 126(a), gas source identifier 128(a), temperature sensor 130(a), gas source identifier reader 131(a), and/or gas source detector 132(a), etc.), primary gas delivery subsystem 140 (e.g., first primary shut off valve 142(a), first primary high flow control valve 143(a), first primary delivery flow sensor 146(a), first primary confirmatory flow sensor 148(a), second primary shut off valve 142(b), second primary high flow control valve 143(b), second primary delivery flow sensor 146(b), and/or second primary confirmatory flow sensor 148(b), etc.), secondary gas delivery subsystem 160 (e.g., secondary shut off valve 162, secondary medium flow control valve 163, secondary delivery flow sensor 166, and/or a secondary confirmatory flow sensor 168, flow regulating 3-way valve 170, low pressure oxygen/air received flow sensor 174, low pressure oxygen/air received confirmatory flow sensor 176, low pressure oxygen/air received pressure sensor 178, and/or overpressure valve 179, etc.), gas analyzing subsystem(s) 180 (e.g., gas sensor 182, gas sensor 186, gas sensor 188, sample gas flow sensor 190; sample pump 192; and/or sample system valve(s) 194, etc.), and/or any other components affiliated with system 100 (e.g., injector module delivery flow sensor 108(*a*), injector module confirmatory flow sensor 108(*b*)).

For another example, subsystem controllers 144 is in electrical communication with the components of primary gas delivery subsystem 140 (e.g., first primary shut off valve 142(*a*), first primary high flow control valve 143(*a*), first primary delivery flow sensor 146(*a*), first primary confirmatory flow sensor 148(*a*), second primary shut off valve 142(*b*), second primary high flow control valve 143(*b*), second primary delivery flow sensor 146(*b*), and/or second primary confirmatory flow sensor 148(*b*), etc.) and/or components of another subsystem such as first gas supply subsystem 110(*a*) (e.g., received therapeutic gas source 116(*a*), therapeutic gas source valve 117(*a*), gas source connection valve 118(*a*), gas pressure sensor 120(*a*), pressure regulator 122(*a*), purge valve 124(*a*), shut off 126(*a*), gas source identifier 128(*a*), temperature sensor 130(*a*), gas source identifier reader 131(*a*), and/or gas source detector 132(*a*), etc.), second gas supply subsystem 110(*b*) (e.g., received therapeutic gas source 116(*b*), therapeutic gas source valve 117(*b*), gas source connection valve 118(*b*), gas pressure sensor 120(*b*), pressure regulator 122(*b*), purge valve 124(*b*), shut off 126(*b*), gas source identifier 128(*b*), temperature sensor 130(*b*), gas source identifier reader 131 (*b*), and/or gas source detector 132(*b*), etc.), primary gas delivery subsystem 140 (e.g., first primary shut off valve 142(*a*), first primary high flow control valve 143(*a*), first primary delivery flow sensor 146(*a*), first primary confirmatory flow sensor 148(*a*), second primary shut off valve 142(*b*), second primary high flow control valve 143(*b*), second primary delivery flow sensor 146(*b*), and/or second primary confirmatory flow sensor 148(*b*), etc.), secondary gas delivery subsystem 160 (e.g., secondary shut off valve 162, secondary medium flow control valve 163, secondary delivery flow sensor 166, and/or a secondary confirmatory flow sensor 168, flow regulating valve 170, low pressure oxygen/air received flow sensor 174, low pressure oxygen/air outlet confirmatory flow sensor 176, low pressure oxygen/air received pressure sensor 178, and/or overpressure valve 179, etc.), gas analyzing subsystem(s) 180 (e.g., gas sensor 182, gas sensor 186, gas sensor 188, sample gas flow sensor 190; sample pump 192; and/or sample system valve(s) 194, etc.), and/or any other components affiliated with system 100 (e.g., delivery flow sensor 108(*a*), injector module confirmatory flow sensor 108(*b*)).

For another example, subsystem controller 164 is in electrical communication with the components of secondary gas delivery subsystem 160 (e.g., secondary shut off valve 162, secondary medium flow control valve 163, secondary delivery flow sensor 166, and/or a secondary confirmatory flow sensor 168, flow regulating valve 170, low pressure oxygen/air received flow sensor 174, low pressure oxygen/air received confirmatory flow sensor 176, low pressure oxygen/air received pressure sensor 178, and/or overpressure valve 179, etc.) and/or components of another subsystem such as first gas supply subsystem 110(*a*) (e.g., received therapeutic gas source 116(*a*), therapeutic gas source valve 117(*a*), gas source connection valve 118(*a*), gas pressure sensor 120(*a*), pressure regulator 122(*a*), purge valve 124 (*a*), shut off 126(*a*), gas source identifier 128(*a*), temperature sensor 130(*a*), gas source identifier reader 131(*a*), and/or gas source detector 132(*a*), etc.), second gas supply subsystem 110(*b*) (e.g., received therapeutic gas source 116(*b*), therapeutic gas source valve 117(*b*), gas source connection valve 118(*b*), gas pressure sensor 120(*b*), pressure regulator 122(*b*), purge valve 124(*b*), shut off 126(*b*), gas source identifier 128(*b*), temperature sensor 130(*b*), gas source identifier reader 131(*b*), and/or gas source detector 132(*b*), etc.), primary gas delivery subsystem 140 (e.g., first primary shut off valve 142(*a*), first primary high flow control valve 143(*a*), first primary delivery flow sensor 146(*a*), first primary confirmatory flow sensor 148(*a*), second primary shut off valve 142(*b*), second primary high flow control valve 143(*b*), second primary delivery flow sensor 146(*b*), and/or second primary confirmatory flow sensor 148(*b*), etc.), gas analyzing subsystem(s) 180 (e.g., gas sensor 182, gas sensor 186, gas sensor 188, sample gas flow sensor 190; sample pump 192; and/or sample system valve(s) 194, etc.), and/or any other components affiliated with system 100 (e.g., injector module delivery flow sensor 108(*a*), injector module confirmatory flow sensor 108(*b*)).

For another example, subsystem controller 184 is in electrical communication with the components of gas analyzing subsystem(s) 180 (e.g., gas sensor 182, gas sensor 186, gas sensor 188, sample gas flow sensor 190; sample pump 192; and/or sample system valve(s) 194, etc.), and/or any other components affiliated with system 100 (e.g., injector module delivery flow sensor 108(*a*), injector module confirmatory flow sensor 108(*b*)) and/or components of another subsystem such as first gas supply subsystem 110(*a*) (e.g., received therapeutic gas source 116(*a*), therapeutic gas source valve 117(*a*), gas source connection valve 118(*a*), gas pressure sensor 120(*a*), pressure regulator 122(*a*), purge valve 124(*a*), shut off 126(*a*), gas source identifier 128(*a*), temperature sensor 130(*a*), gas source identifier reader 131 (*a*), and/or gas source detector 132(*a*), etc.), second gas supply subsystem 110(*b*) (e.g., received therapeutic gas source 116(*b*), therapeutic gas source valve 117(*b*), gas source connection valve 118(*b*), gas pressure sensor 120(*b*), pressure regulator 122(*b*), purge valve 124(*b*), shut off 126(*b*), gas source identifier 128(*b*), temperature sensor 130(*b*), gas source identifier reader 131(*b*), and/or gas source detector 132(*b*), etc.), primary gas delivery subsystem 140 (e.g., first primary shut off valve 142(*a*), first primary high flow control valve 143(*a*), first primary delivery flow sensor 146(*a*), first primary confirmatory flow sensor 148(*a*), second primary shut off valve 142(*b*), second primary high flow control valve 143(*b*), second primary delivery flow sensor 146(*b*), and/or second primary confirmatory flow sensor 148(*b*), etc.), secondary gas delivery subsystem 160 (e.g., secondary shut off valve 162, secondary medium flow control valve 163, secondary delivery flow sensor 166, and/or a secondary confirmatory flow sensor 168, flow regulating valve 170, low pressure oxygen/air received flow sensor 174, low pressure oxygen/air received confirmatory flow sensor 176, low pressure oxygen/air received pressure sensor 178, and/or overpressure valve 179, etc.), and/or any other components affiliated with system 100 (e.g., injector module delivery flow sensor 108(*a*), injector module confirmatory flow sensor 108(*b*)).

In one or more embodiments, each subsystem controller 129(*a*), 129(*b*), 144, 164, 184 communicates with each of the other subsystem controllers 129(*a*), 129(*b*), 144, 164, 184 and at least therapeutic gas delivery system controllers 144, 164 are configured to detect faults, errors, and/or failures, including complete subsystem controller failure. In various embodiments, therapeutic gas delivery system controllers 144, 164 are configured to take over operation of another subsystem controller if and when a fault, error, and/or failure is detected.

The clock circuits may be internal to the system controller and/or provide a measure of time relative to an initial start, for example on boot-up. The system may comprise a real-time clock (RTC) that provides actual time, which may be synchronized with a time-keeping source, for example a network. The memory may be configured to receive and store values for calculations and/or comparison to other values, for example from sensor(s), pumps, valves, etc.

In exemplary embodiments, the memory may store a set of machine-executable instructions (or algorithms), when executed by processors, that can cause the therapeutic gas delivery system and/or any of the subsystems (e.g., functioning independently of one another, any of the subsystems functioning in concert, etc.) to perform various methods and operations.

For example, the delivery subsystems 140, 160 can perform methods to deliver a desired set dose of therapeutic gas (e.g., NO concentration, mg/kg/hr, NO PPM, etc.) to a patient in need thereof comprising: receiving and/or determining a desired set dose of therapeutic gas to be delivered to a patient that may be input by a user; measuring flow in the inspiratory limb of a patient breathing circuit; adjusting a flow control valve to change the amount of therapeutic gas flowing; delivering therapeutic gas containing NO to the patient during inspiratory flow; monitoring inspiratory flow or changes in the inspiratory flow; and/or varying the quantity (e.g. volume or mass) of therapeutic gas delivered in a subsequent inspiratory flow.

For another example, the gas analyzing subsystem 180 can perform methods to determine the concentration of target gas (e.g., NO, CO, etc.) being delivered to a patient comprising: actuating a sampling pump and/or opening a gas sampling valve (e.g., three way valve, etc.) to obtain a gas sample from the inspiratory limb of a patient breathing circuit, the gas sample being of blended air and therapeutic gas (e.g., NO) being delivered to a patient; exposing the gas sample to gas sensors (e.g., catalytic type electrochemical gas sensors); obtaining information from the sensor indicative of the concentration of target gas (e.g., NO, nitrogen dioxide, oxygen) being delivered to the patient; and/or communicating to the user the concentration of the target gas. s For yet another example, the gas analyzing subsystem 180 can perform method to perform calibrations (e.g., baseline calibrations) of the gas sensor (e.g., catalytic type sensor, electrochemical gas sensor, NO sensor, etc.) comprising: actuating a sampling pump and/or opening a gas sampling valve (e.g., three way valve, etc.) to obtain a gas sample of ambient air (e.g., conditioned room air); exposing the gas sample of ambient air to gas sensors (e.g., catalytic electrochemical NO gas sensors); obtaining information from the sensor indicative of concentration of target gas (e.g., NO) in the ambient air (e.g., 0 PPM NO); and/or generating a new calibration line and/or modifying an existing calibration line by, for example, replacing the initial and/or previous information indicative of zero concentration target gas (e.g., 0 PPM NO) with the obtained information indicative of zero PPM target gas and using the slope of the initial and/or previous calibration line (e.g., slope of initial and/or previous calibration line connecting the initial and/or previous zero and span calibration points). The machine-executable instructions may also comprise instructions for any of the other teachings described herein.

In exemplary embodiments, systems and methods of the present invention can include one or more gas supply subsystems (e.g., first gas supply subsystem 110(*a*), second gas supply subsystem 110(*b*), etc.) capable of receiving therapeutic gas (e.g., from a therapeutic gas source) and/or providing the therapeutic gas to a primary and/or secondary delivery subsystem.

First, second gas supply subsystem 110(*a*), 110(*b*) can include, but is not limited to, a receptacle (not shown) for receiving a therapeutic gas source 116(*a*), 116(*b*). When received, a therapeutic gas source valve 117(*a*), 117(*b*) of therapeutic gas source 116(*a*), 116(*b*) can be actuated enabling therapeutic gas to exit from therapeutic gas source 116(*a*), 116(*b*). In exemplary embodiments, first, second gas supply subsystem 110(*a*), 110(*b*) can include, but is not limited to, a gas source coupling 115(*a*), 115(*b*); a gas source connection valve 118(*a*), 118(*b*); a gas pressure sensor 120(*a*), 120(*b*); a pressure regulator 122(*a*), 122(*b*); a purge valve 124(*a*), 124(*b*); and/or a shut off 126(*a*), 126(*b*). In at least some instances, a gas source identifier 128(*a*), 128(*b*) and/or a temperature sensor 130(*a*), 130(*b*) can be affiliated with gas source 116(*a*), 116(*b*). Further, in at least some instance, a gas source identifier reader 131(*a*), 131(*b*); and/or a gas source detector 132(*a*), 132(*b*); can be used to determine whether or not a gas source has been received and/or loaded properly.

By way of example, gas source coupling 115(*a*), 115(*b*) can be configured to receive therapeutic gas source 116(*a*), 116(*b*), enabling a fluid flow connection with the therapeutic gas source, connection valve 118(*a*), 118(*b*) with system 100, wherein connection valve 118(*a*), 118(*b*) is configured to have at least an open state and a closed state. Further, gas pressure sensor 120(*a*), 120(*b*) can be adjacent to and in fluid communication with connection valve 118(*a*), 118(*b*), wherein connection valve 118(*a*), 118(*b*) provides a gas flow path 119(*a*), 119(*b*) from the connection valve 118(*a*), 118(*b*) to gas pressure regulator 122(*a*), 122(*b*). Following this configuration, the gas pressure sensor can be configured to measure a gas pressure at the gas source (e.g., between connection valve 118(*a*), 118(*b*) and therapeutic gas pressure regulator 122(*a*), 122(*b*), for example, at least when the connection valve 118(*a*), 118(*b*) and therapeutic gas source valve 117(*a*), 117(*b*) is in an open state, etc.). Further, the gas pressure sensor can be configured to measure gas pressure at therapeutic gas pressure regulator 122(*a*), 122(*b*) downstream from gas pressure sensor 120(*a*), 120(*b*), connection valve 118(*a*), 118(*b*). As used herein, "adjacent to" means abutting or adjoining a neighboring component, where an adjacent downstream component immediately follows the upstream component without other intervening components, and with minimal internal volume (e.g., dead space) between the upstream component and the downstream component. For example, a connection valve and/or gas pressure sensor may have short conduits leading to and from the actual mechanisms, so that even if an inlet of a gas pressure sensor were connected directly to an outlet of a the connection valve there may still be a length of fluid flow path between the connection valve mechanism and the gas pressure sensor mechanism. Similarly, the fluid flow path may comprise a short length of conduit 119(*a*), 119(*b*) (e.g., tubing, channels, etc.) to which the connection valve 118(*a*), 118(*b*) and the gas pressure sensor 120(*a*), 120(*b*) may be coupled due to the type of unions used on the gas source valve and the gas pressure sensor. Further, in exemplary embodiments, all conduits placing any and/or all components in fluid connection with therapeutic gas can be minimized and/or eliminated such that "dead ends" (e.g., dead space between the component and the conduit) can be minimized and/or eliminated, for example, as these "dead ends" can be substantially difficult to purge and/or can cause NO2 generation and/or NO2 can be substantially difficult to purge from "dead ends".

While the first gas supply subsystem 110(a) is depicted as being located on the left side of the drawing and the second gas supply subsystem 110(b) is depicted as being located on the right side of the drawing, this is for illustrative purposes of an exemplary embodiment, and should not be construed as a limitation, for which reference should be made to the claims. In addition, while the gas supply subsystems may be referred to as a first gas supply subsystem 110(a) and a second gas supply subsystem 110(b), this is not intended to connote sequence or preference, but is for ease of reference and should not be construed as a limitation, for which reference should be made to the claims. Further, while the gas supply subsystems may be referred to as a first and second gas supply subsystems, this should not be construed that there may only be two gas supply subsystems as additional gas supply subsystems are envisioned, rather it is for ease of reference and should not be construed as a limitation, for which reference should be made to the claims.

In various embodiments, the therapeutic gas source 116(a), 116(b) may be a compressed gas cylinder with an initial gas pressure of about 2000 psi to about 5000 psi having an NO concentration of about 2000 ppm to about 10000 ppm, an initial gas pressure of about 3000 psi having an NO concentration of about 4880 ppm, an initial gas pressure of about 2000 psi to about 5000 psi having an NO concentration of about 400 ppm to about 1600 ppm, and/or an initial gas pressure of about 1800 psi having an NO concentration of about 800 ppm. Of course other initial pressures and/or NO concentrations are envisioned. In one or more embodiments, therapeutic gas source 116(a), 116(b) may be a mini cylinder that can contain a pressurized therapeutic gas at a pressure in the range of about 2000 psi to about 300 psi, or at a pressure of about 3000 psi, where the mini cylinder weighs less than ⅓ the weight of a standard sized gas cylinder (e.g., about 30 lbs. to 50 lbs.) and/or the mini cylinder weights about 1.4 lbs. while providing the same or greater run-time-to-empty compared to previous cylinders (e.g., standard sized gas cylinders). In various embodiments, the lighter mini cylinder(s) enables easier manual cylinder distribution because it require less strength from a user to move and manipulate, and provides more efficient storage in a manner that takes up less physical space than larger standard cylinders. In various embodiments, the mini cylinder may contain a therapeutic gas having a concentration in the range of about 2000 ppm to about 10,000 ppm, or about 4000 ppm to about 10,000 ppm. In various embodiments, the therapeutic gas source is an NO mini cylinder having an NO concentration of about 2000 ppm to about 10000 ppm, and an initial gas pressure of about 3000 psi, or an NO concentration of about 4880 ppm and an initial gas pressure of about 3000 psi.

In exemplary embodiments, the gas supply system receptacle and therapeutic gas source can be configured such that only the desired therapeutic gas source 116(a), 116(b) can be coupled to the gas supply subsystem 110(a), 110(b). In at least some instances, to ensure that the desired gas source is being received, gas source coupling 115(a), 115(b) can be configured to mate with compatible coupling member 114(a), 114(b) of therapeutic gas source 116(a), 116(b). For example, systems and methods of the present invention can include and/or be modified such that they can work with any of the teaching in U.S. Pat. No. 8,757,148 entitled "Devices And Methods For Engaging Indexed Valve And Pressurized Canister Assembly With Collar And For Linear Actuation By Plunger Assembly Into Fluid Communication With Device For Regulating Drug Delivery", the contents of which is incorporated by reference herein in its entirety. In one or more embodiments, the gas source coupling 115(a), 115(b) and/or matching coupling member 114(a), 114(b) comprises an indexed drug delivery device as described in U.S. Pat. No. 8,757,148. Systems and methods of the present invention can include and/or be modified such that they can work with any of the teaching in U.S. Pat. No. 8,757,148. In various embodiments, the gas source coupling 115(a), 115(b) and matching coupling member 114(a), 114(b) are polarized so a therapeutic gas source 116(a), 116(b) may only be coupled with the gas source coupling with a predetermined orientation. In various embodiments, the therapeutic gas source may be aligned by the gas source coupling, so a gas source identifier 128(a), 128(b) attached to the therapeutic gas source faces in a particular direction. In at least some instances, mechanical and visual guides can be used to aid in the loading of the therapeutic gas source into the receptacle.

In various embodiments, gas supply subsystem 110(a), 110(b) may comprise gas source identifier reader 131(a), 131(b) and/or temperature sensor 130(a), 130(b) that may be positioned within a bay and/or receptacle for receiving therapeutic gas source 116(a), 116(b). Gas source identifier reader 131(a), 131(b) and/or temperature sensor 130(a), 130(b) may be used to, amongst other things, obtain data from the gas source identifier 128(a), 128(b), and/or temperature values of the therapeutic gas source 116(a), 116(b). Further, in at least some instance, a gas source detector 132(a), 132(b) can be used to determine whether or not a therapeutic gas source 116(a), 116(b) has been received and/or mated properly.

In one or more embodiments, therapeutic gas source detector 132(a), 132(b) is operatively associated with the gas source coupling 115(a), 115(b), where the therapeutic gas source detector 132(a), 132(b) is configured to detect when the therapeutic gas source 116(a), 116(b) is properly received by the respective gas source coupling 115(a), 115(b). In various embodiments, the therapeutic gas source detector 132(a), 132(b) is configured to communicate a signal indicating the presence of the therapeutic gas source 116(a), 116(b) to the therapeutic gas delivery system controller and/or respective subsystem controllers 129(a), 129(b). In various embodiments, the therapeutic gas source detector 132(a), 132(b) may be for example a micro-switch, a limit switch, or a proximity detector (e.g., Hall Effect Sensor).

In exemplary embodiments, connection valve 118(a), 118(b) may also prevent loud noise or bang from rapid venting of high pressure gas from conduit/manifold 119 when removing therapeutic gas source 116(a), 116(b). Connection valve 118(a), 118(b), in at least some instances, can also function to keep air out of the high pressure manifold upstream of pressure regulator 122(a), 122(b).

In exemplary embodiments, pressure regulator 122(a), 122(b) may be configured to reduce the high pressure therapeutic gas from the therapeutic gas source (e.g., 2000 psi, 3000 psi, etc.) to an operating pressure (e.g., 20 psi, 30 psi, etc.).

In exemplary embodiments, primary gas delivery subsystem 140 can be in fluid communication with first gas supply subsystem 110(a) and/or second gas supply subsystem 110(b) such that NO can be received from either and/or both gas supply subsystems (e.g., via conduit 101(a), via conduit 101(b), etc.). Primary gas delivery subsystem 140 can be in fluid communication with a delivery gas pressure sensor(s)

109 (e.g., which can be shared between the primary and secondary delivery sub systems as shown) enabling pressure measurement of NO being supplied from either and/or both gas supply subsystems and/or the therapeutic gas pressure in conduit 101(*a*) and conduit 101(*b*). Further, NO received from either and/or both gas supply subsystems can be in fluid communication with a first primary flow control channel 141(*a*) (e.g., a high flow control channel) and/or a second primary flow control channel 141(*b*) (e.g., a low flow control channel) such that flow of NO can be controlled. First flow control channel 141(*a*) can be in fluid communication with a first primary shut off valve 142(*a*), a first primary high flow control valve 143(*a*), a first primary delivery flow sensor 146(*a*), and/or a first primary confirmatory flow sensor 148(*a*). Similarly, second flow control channel 141(*b*) can be in fluid communication with a second primary shut off valve 142(*b*), a second primary high flow control valve 143(*b*), a second primary delivery flow sensor 146(*b*), and/or a second primary confirmatory flow sensor 148(*b*).

In exemplary embodiments, gas delivery subsystem 140 can deliver therapeutic gas, at a desired set dose (e.g., a desired concentration) to a patient (e.g., via an injector module coupled to a patient breathing circuit affiliated with a ventilator). For example, gas delivery subsystem 140 can wild stream blend therapeutic gas (e.g., NO, etc.), via injector module 107, into patient breathing gas in breathing circuit 209, affiliated with ventilator 205, as a proportion of the patient breathing gas. To at least wild stream blend therapeutic gas (e.g. NO, etc.) into patient breathing gas, gas delivery subsystem 140 can receive NO from NO gas source 116(*a*) and/or NO gas source 116(*b*), via flow control channel 141(*a*) and/or flow control channel 141(*b*), and provide the therapeutic gas, via a delivery conduit 111 that can also be in fluid communication with an injector module 107, which in turn can also be in fluid communication with the inspiratory limb of breathing circuit 209 affiliated with ventilator 205. In various embodiments, therapeutic gas flowing through delivery conduit 111 can be the sum of therapeutic gas flowing through flow control channel 141(*a*) (e.g., a high flow control channel) and flow control channel 141(*b*) (e.g., a low flow control channel). Further, to at least wild stream blend therapeutic gas into patient breathing gas, breathing circuit gas flow information can be provided by sensors, such as flow sensor 108(*a*) and/or flow sensor 108(*b*) affiliated with injector module 107, in fluid communication with the breathing circuit and/or flow information can be received from the ventilator.

To regulate flow of NO through delivery conduit 111 to injector module 107, and in turn to a patient 203 receiving breathing gas from inspiratory limb 213 of patient breathing circuit 209, one or more flow control valves 143(*a*) and/or 143(*b*) (e.g., proportional valves, binary valves, etc.) can open enabling NO delivery to patient 203 by flowing NO received from at least one of the gas supply subsystems by the corresponding flow control channel to injector module 107, via delivery conduit 111, and in turn into inspiratory limb 213 of patient breathing circuit 209 and to patient 203. In at least some instances, NO delivery system 100 can include one or more therapeutic gas flow sensors 146(*a*), 146(*b*), 148(*a*), and/or 148(*b*) that can measure the flow of therapeutic gas through flow control valves 143(*a*) and/or 143(*b*) and/or delivery conduit 111, in turn enabling measurement of the flow of therapeutic gas to injector module 107, and in turn to patient 203

In exemplary embodiments, therapeutic gas flow (e.g., NO gas flow) can be wild stream blended proportional to the breathing gas (e.g., air) flow to provide a desired set dose concentration of the therapeutic gas (e.g., NO) in the combined breathing gas and therapeutic gas. For example, a user can input a desired set dose and the delivery system can deliver this set dose to patient 203. Further, NO delivery system 100 can execute, for example, using machine-executable instructions, a delivered concentration calculation that confirms that the desired concentration of the therapeutic gas (e.g., NO) is in the combined breathing gas and therapeutic gas using the known concentration of therapeutic gas source 116(*a*), 116(*b*); the amount of breathing gas flow in the patient circuit using information from BCG flow sensors 108(*a*) and/or 108(*b*) and/or from ventilator 205; and the amount of therapeutic gas flow in delivery conduit 111 going to injector module 107 (and in turn to patient 203) using information from therapeutic gas flow sensors 146(*a*), 146(*b*), 148(*a*), and/or 148(*b*).

With respect to at least the backup, or secondary, delivery subsystem, at times referred to as an "eblender" or the like, of the present invention, some found previous backup systems to be difficult and intimidating, and required extensive training with regard to switch over from ventilator delivered therapeutic gas to manually delivered therapeutic gas. In exemplary embodiments, secondary delivery subsystem 160 provides a simple and/or automatic backup system for primary delivery subsystem 140, as well as a manual ventilation system as a simple and/or automatic backup system for ventilator 205 supplied breathing gas and patient breathing circuit 209. Further, in exemplary embodiments, the present invention provides an automatic backup, or secondary, delivery system (e.g., eblender), links dose settings of the secondary delivery subsystem to the dose set at a primary delivery subsystem so the patient dose remains at the desired set dose, provides monitoring or confirmation of a set dose, provides backup systems which can, if needed, function independently from the rest of the system.

In exemplary embodiments, similar to primary gas delivery subsystem 140, secondary gas delivery subsystem 160 can be in fluid communication with first gas supply subsystem 110(*a*) and/or second gas supply subsystem 110(*b*) such that NO can be received from either and/or both gas supply subsystems (e.g., via conduit 101(*a*), via conduit 101(*b*), via conduit 101(*a*) and conduit 101(*b*), etc.). Again similar to primary gas delivery subsystem 140, secondary gas delivery subsystem 160 can be in fluid communication a delivery gas pressure sensor(s) 109 (e.g., which can be shared between the primary and secondary delivery subsystems as shown) enabling pressure measurement of NO being supplied from either and/or both gas supply subsystems. Further, NO received from either and/or both gas supply subsystems can be in fluid communication with a secondary flow control channel 161(*a*) (e.g., a medium flow control channel) such that flow of NO can be controlled. Secondary flow control channel 161(*a*) can be in fluid communication with a secondary shut off valve 162, a secondary medium flow control valve 163, a secondary delivery flow sensor 166, and/or a secondary confirmatory flow sensor 168. Further, secondary flow control channel 161(*a*) can be in fluid communication with a flow regulating valve 170 that can control whether flow from secondary gas delivery system goes to injector module 107 or to another assisted breathing apparatus (e.g., a bag valve mask, etc.).

In one or more embodiments, secondary delivery subsystem 160 also comprises flow regulating valve 170 that can control whether flow from secondary gas delivery system 160 goes to injector module 107 or to another assisted breathing apparatus (e.g., bag valve mask, etc.). In various embodiments, flow regulating valve 170 may be a three-way valve that is configured to direct a gas flow stream to an injector module outlet or low pressure outlet 167 for a bag valve mask. In various embodiments, the flow regulating valve 170 may include one or more proportional control valves, binary valves, or a 3-way valve, where the valve(s) may be configured to direct the gas flow.

In exemplary embodiments, similar to primary gas delivery subsystem 140, secondary gas delivery subsystem 160 can deliver therapeutic gas, at a desired set dose (e.g., a desired concentration), to a patient (e.g., via an injector module coupled to a patient breathing circuit affiliated with a ventilator). For example, secondary gas delivery subsystem 160 can wild stream blend therapeutic gas (e.g., NO, etc.), via injector module 107, into patient breathing gas in breathing circuit 209, affiliated with ventilator 205, as a proportion of the patient breathing gas. To at least wild stream blend therapeutic gas (e.g. NO, etc.) into patient breathing gas, secondary gas delivery subsystem 160 can receive NO from a NO gas source 116(*a*) and/or NO gas source 116(*b*), via flow control channel 161(*a*) and flow regulating valve 170, and provide the therapeutic gas, via a delivery conduit 111 that can also be in fluid communication with an injector module 107, which in turn can also be in fluid communication with the inspiratory limb of breathing circuit 209 affiliated with ventilator 205. Further, to at least wild stream blend therapeutic gas into patient breathing gas, breathing circuit gas flow information can be provided by sensors, such as flow sensor 108(*a*) and/or flow sensor 108(*b*) affiliated with injector module 107, in fluid communication with the breathing circuit and/or flow information can be received from the ventilator.

To regulate flow of NO through delivery conduit 111 to injector module 107, and in turn to a patient 203 receiving breathing gas from inspiratory limb 213 of patient breathing circuit 209, at least one flow control valve 163 (e.g., proportional valves, binary valves, etc.) can open enabling NO delivery to patient 203 by flowing NO received from at least one of the gas supply subsystems by the corresponding flow control channel to injector module 107, via delivery conduit 111, to injector module 107, and in turn into inspiratory limb 213 of patient breathing circuit 209 and to patient 203. In at least some instances, NO delivery system 100 can include one or more therapeutic gas flow sensors 166 and/or 168 that can measure the flow of therapeutic gas through the at least one flow control valve 163 and/or delivery conduit 111, in turn enabling measurement of the flow of therapeutic gas to injector module 107, and in turn to patient 203.

In exemplary embodiments, therapeutic gas flow (e.g., NO gas flow) can be wild stream blended proportional to the breathing gas (e.g., air) flow to provide a desired set dose concentration of the therapeutic gas (e.g., NO) in the combined breathing gas and therapeutic gas. For example, a user can input a desired set dose and the delivery system can deliver this set dose to patient 203. Further, NO delivery system 100 can execute, for example, using machine-executable instructions, a delivered concentration calculation that confirms that the desired concentration of the therapeutic gas (e.g., NO) is in the combined breathing gas and therapeutic gas using the known concentration of therapeutic gas source 116(*a*), 116(*b*); the amount of breathing gas flow in the patient circuit using information from BCG flow sensors 108(*a*) and/or 108(*b*) and/or from ventilator 205; and the amount of therapeutic gas flow in delivery conduit 111 going to injector module 107 (and in turn to patient 203) using information from therapeutic gas flow sensors 166 and/or 168.

In exemplary embodiments, secondary delivery subsystem 160 can receive oxygen and/or air (e.g., from the low pressure outlet of an external gas supply such as a wall gas regulator, from a wall outlet, cylinder, etc.) that can be wild stream blended with NO, for example, from gas supply subsystem A and/or gas supply subsystem B as described above, which in turn can be delivered to an assisted breathing apparatus (e.g., a bag valve mask). By way of example, to at least wild stream blend NO with oxygen and/or air (e.g., from the low pressure outlet of a wall gas regulator, from a wall outlet, etc.) NO received from either and/or both gas supply subsystems can be in fluid communication with secondary flow control channel 161(*a*) (e.g., a medium flow control channel) such that flow of NO can be controlled. Further, a low pressure conduit 172 can receive low pressure oxygen and/or air (e.g., from the low pressure outlet of a wall gas regulator) via low pressure conduit pass through inlet (e.g., coupled to a low pressure delivery conduit from the low pressure outlet of a wall gas regulator), that may be in fluid communication with a filter, and this received low pressure air can be wild stream blended with NO from either and/or both gas supply subsystems, for example at blending junction 169. Low pressure conduit 172 can be in fluid communication with a low pressure oxygen/air received flow sensor 174, a low pressure oxygen/air received confirmatory flow sensor 176, and/or a low pressure oxygen/air received pressure sensor 178. Following the above example, flow regulating valve 170 (e.g., a three way valve, directional valve, etc.) can be actuated such that NO from secondary flow control channel 161(*a*) flows to blending junction 169 wherein the NO and oxygen and/or air can be wild stream blended, and in turn, this NO and air and/or oxygen can flow to the assisted breathing apparatus (e.g., a bag valve mask, etc.).

For ease, in at least this configuration, the assisted breathing apparatus is, at times, described as a bag valve mask. Of course other assisted breathing apparatus are envisioned such as, but not limited to, a bag valve mask, nasal cannula, face mask, etc. Accordingly, reference to a bag valve mask is merely for ease and is in no way meant to be a limitation.

In exemplary embodiments, secondary gas delivery subsystem 160 can deliver therapeutic gas, at a desired set dose (e.g., a desired concentration), to a patient, via a bag valve mask, by wild stream blending therapeutic gas (e.g., NO, NO from either and/or both gas supply subsystems, etc.) into low pressure oxygen and/or air (e.g., from the low pressure outlet of a wall gas regulator) as a proportion of low pressure oxygen and/or air. Further, to at least wild stream blend therapeutic gas into low pressure oxygen and/or air, flow information can be provided by sensors, such as flow sensor 174, flow sensor 176, and/or pressure sensor 178, in fluid communication low pressure conduit 172. For ease, only a low pressure oxygen and/or air/O2 is described. This is merely for ease and is in no way meant to be a limitation, for example, as usage of high pressure oxygen and/or air is envisioned. For example, conduits, valves, flow sensors, etc. can be modified for high pressure and/or therapeutic gas delivery system 100 can include and/or function with a pressure regulator (e.g., to decrease the source pressure, etc.). Accordingly, one skilled in the art will appreciate how therapeutic gas system 100 may function with high pressure oxygen and/or air.

As described above with respect to NO delivery to injector module 107, to regulate flow of NO through flow control channel 161(*a*) to a bag valve mask, and in turn to a patient 203, at least one flow control valve 163 (e.g., proportional valves, binary valves, etc.) can open enabling NO flow to blending junction 169. At blending junction 169 NO and low pressure oxygen and/or air can be wild stream blended and this NO and oxygen and/or air can in turn flow to a bag valve mask. In at least some instances, NO delivery system 100 can include one or more therapeutic gas flow sensors 166 and/or 168 that can measure the flow of therapeutic gas through the at least one flow control valve 163 and/or flow control channel 161(*a*), in turn enabling measurement of the flow of therapeutic gas to blending junction 169.

In exemplary embodiments, therapeutic gas flow (e.g., NO gas flow) can be wild stream blended proportional to the low pressure oxygen and/or air flow to provide a desired set dose concentration of the therapeutic gas (e.g., NO) in the combined low pressure oxygen and/or air and therapeutic gas. For example, a user can input a desired set dose and the delivery system 160 can deliver this set dose to patient 203. Further, NO gas delivery system 100 can execute, for example, using machine-executable instructions, a delivered concentration calculation that confirms that the desired concentration of the therapeutic gas (e.g., NO) is in the combined low pressure oxygen and/or air and therapeutic gas using the known concentration of therapeutic gas source 203; the amount of low pressure oxygen and/or air using information from flow sensors 174 and/or 176; and the amount of therapeutic gas flow from flow control channel 161 going to blending junction 169 using information from therapeutic gas flow sensors 166 and/or 168.

In exemplary embodiments, overpressure valve 179 can be in fluid communication with low pressure conduit 172 to, for example, ensure that the pressure in low pressure conduit 172 is not above a predetermined threshold. Overpressure valve 179 can be used to ensure that sensors in fluid communication with low pressure conduit 172 and/or low pressure conduit 172 itself is not damaged by being exposed to high pressure gas (e.g., that may be provided from the high pressure outlet of an oxygen and/or air source).

In at least some instances, system 100 can have fewer or additional delivery subsystems (e.g., primary delivery subsystem 140, secondary delivery subsystem 160, etc.) and/or system 100 and/or delivery subsystems can have fewer or additional flow control channels and associated elements. For ease, only a primary delivery subsystem having two flow control channels and associated elements (e.g., shut off valves, control valves, flow sensors, confirmatory flow sensors, etc.) and a secondary delivery subsystem having a single flow control channels and associated elements (e.g., shut off valves, control valves, flow sensors, confirmatory flow sensors, etc.) are shown. This is merely for ease and is in no way meant to be a limitation. For example, primary delivery subsystem can include any number of flow control channels, such as, a third flow control channel (not shown) that may be in fluid communication with associated elements (e.g., a third primary shut off valve, a third primary flow control valve, a third primary delivery flow sensor, and/or a third primary confirmatory flow sensor, etc.). For another example, secondary delivery subsystem can include any number of flow control channels, such as, a second flow control channel (not shown) that may be in fluid communication with associated elements (e.g., a second secondary shut off valve, a second secondary flow control valve, a second secondary delivery flow sensor, and/or a second secondary confirmatory flow sensor, etc.). For yet another example, system 100 can include a tertiary delivery subsystem (not shown) that can have any number of flow control channels, such as, a first flow control channel that may be in fluid communication with associated elements (e.g., a first tertiary shut off valve, a first tertiary flow control valve, a first tertiary delivery flow sensor, and/or a first tertiary confirmatory flow sensor, etc.), a second flow control channel that may be in fluid communication with associated elements (e.g., a second tertiary shut off valve, a second tertiary flow control valve, a second tertiary delivery flow sensor, and/or a second tertiary confirmatory flow sensor, etc.), and/or a third flow control channel that may be in fluid communication with associated elements (e.g., a third tertiary shut off valve, a third tertiary flow control valve, a third tertiary delivery flow sensor, and/or a third tertiary confirmatory flow sensor, etc.).

In at least some instances, flow control valves can control various ranges of flow (e.g., high flow, low flow, medium flow, etc.) and/or the same range of flows (e.g., one or more high flow valves, one or more low flow valves, one or more medium flow valves, etc.). For ease, flow control valves (e.g., flow control valve 143(*a*), flow control valve 143(*b*), flow control valve 163, etc.) are, at times, described as high flow control valves, low flow control valves, medium flow control valves, and the like. This is merely for ease and is in no way meant to be a limitation. Of course other ranges of flow and/or additional flow control valves and/or ranges are envisioned.

In at least some instances, flow control valves (e.g., flow control valve 143(*a*), flow control valve 143(*b*), flow control valve 163, etc.) can be any type of valve capable of controlling gas flow such as, but not limited to, proportional valves, binary valves, any combination or further separation thereof, and/or any other type of valve.

In at least some instances, therapeutic gas flow sensors 146(*a*), 146(*b*), 148(*a*), 148(*b*), 166, and/or 168 and flow control valves (e.g., flow control valve 143(*a*), flow control valve 143(*b*), flow control valve 163, etc.) in corresponding flow control channels can be configured such that the flow sensors may be upstream, downstream, and/or combinations thereof of the corresponding flow control valve(s). Therapeutic gas delivery system 100 is described, at times, as having flow sensors one corresponding confirmatory flow sensor. This is merely for ease and is in no way meant to be a limitation because, for example, more than one corresponding confirmatory flow sensor is envisioned.

In one or more embodiments, the therapeutic gas delivery system 100 can have one or more inlet ports and outlet ports, where the ports may be general ports to allow connecting and/or fluid communication of the system to external components (e.g., injector module outlet port), or dedicated ports that provide connection and/or fluid communication of external components to particular subsystem(s) and/or components to provide specific system functions (e.g., low pressure air inlet port, gas analyzing inlet port). In various embodiments, the inlet ports and outlet ports may comprise connectors, for example quick disconnect gas connectors, hose barb connectors, and hose couplings, to name a few. In exemplary embodiments, therapeutic gas delivery system 100 can comprise a primary outlet port (also referred to as an injector module outlet port) for connection to an injector module, a low pressure outlet 167 for connection to a manual ventilation device, and a low pressure inlet port 165 for connection to a low pressure air/O$_2$ supply.

In exemplary embodiments, therapeutic gas delivery system 100 can allow a user to input a desired set dose of the therapeutic gas (e.g., NO in PPM) and the therapeutic gas delivery system can confirm that the desired set dose of the therapeutic gas is being delivered to the patient by calculating the delivery concentration (e.g., as described above) as well as using gas analyzing system 180 to confirm the desired set dose of the therapeutic gas (e.g., NO) is being delivered to the patient. Gas analyzing subsystem 180 can include, but is not limited to numerous sensors such as, but not limited to, an electrochemical NO gas sensor 182, which may have a catalytic type electrode material with high catalytic activity for the electrochemical reactions of the sensor, a catalytic type electrochemical nitrogen dioxide gas sensor 186, and a galvanic type electrochemical oxygen gas sensor 188, to name a few; a sample gas flow sensor(s) 190; a sample pump(s) 192; sample system valve(s) 194; and/or controller 184. Sensors 182, 186, and 188 can be in series and/or parallel and/or can be in any order. For ease, sensors 182, 186, and 188 are illustratively depicted as being in series. This is merely for ease and is in no way meant to be a limitation. In various embodiments, the NO sensor may be an electrochemical sensor, which may comprise two electrodes, including a sensing and a counter electrode, separated by a thin layer of electrolyte.

In exemplary embodiments, gas analyzing subsystem 180 can sample and/or measure the concentration of various gases being delivered to a patient. The concentration of NO being delivered to patient 203 can be sampled and exposed to NO sensor 182, which in turn can output information indicative of the concentration of NO in the breathing gas (e.g., NO PPM). For example, a sample of the gas being delivered to the patient can be sampled via a sample line 119 that is in fluid communication with inspiratory line 213 of breathing circuit 209 affiliated with breathing apparatus 205. Sample line 119 can be in fluid communication with inspiratory limb 213 via a sampling "T" 121 which can be coupled to inspiratory line 213. This gas sample from the inspiratory limb, via sample line 119, can flow and/or be pulled to the gas sensors 182, 186, 188 (e.g., NO sensor 182, nitrogen dioxide gas sensor 186, oxygen gas sensor 188, etc.). Flow in sample line 119 can be regulated via valve 194 and/or sample pump 192. Sample line mass or volume flow can be measured using flow sensor 190. Sample line 119 can also be in fluid communication with a gas sample conditioner 196 that may condition the sample gas, for example, by extracting fluids, placing the sample at the appropriate humidity, removing contaminants from the sample, and/or can condition the sample gas in any other way as desired.

In exemplary embodiments, gas analyzing subsystem 180 can perform calibrations (e.g., baseline calibrations, span calibrations, etc.) of the gas sensor (e.g., catalytic type electrochemical gas sensor, etc.) by sampling and/or measuring the concentration of target gases in a controlled sample (e.g., baseline sample, span sample, etc.), where a span sample is a target gas (i.e., nitric oxide) with a specific known and controlled concentration within a range of interest (e.g., 10 PPM, 25 PPM, 50 PPM, 80 PPM, etc.) and/or where a baseline sample is a gas containing zero concentration of a target gas (i.e., conditioned ambient air containing zero nitric oxide). For example, a sample of ambient gas and/or span gas can be sampled via a sample line 119 and/or 198 that can be in fluid communication with valve 194. This gas sample can flow and/or be pulled to the gas sensors (e.g., NO sensor 182, etc.) wherein the flow can regulated via valve 194 (e.g., a three way valve, etc.) and/or sample pump 192. Sample line flow can be measured using flow sensor 190.

In exemplary embodiments, sample line 119 can also be in fluid communication with a gas sample conditioner (not shown) that may condition the sample gas, for example, by extracting fluids, placing the sample at the appropriate humidity, removing contaminants from the sample, and/or can condition the sample gas in any other way as desired.

For example, the ambient air used for the baseline calibration may be scrubbed of any undesirable gases using a scrubber material. By way of example, this scrubbing material can be an inline Potassium permanganate scrubber material capable of scrubbing the ambient air removing NO and NO2. With the NO and NO2 removed from the ambient air, the scrubbed air can be used for a zero calibration as these undesirable gases have been removed hence they are at 0 PPM. If needed, a similar technique (e.g., using an inline scrubber material) can be done for span gas.

Therapeutic Gas Source Management

In exemplary embodiments, at least some aspect of the present invention relate to systems, methods, and/or process for, amongst other things, managing use of one or more therapeutic gas sources, receipt of therapeutic gas source, receiving information from therapeutic gas sources, performing run-time-to-empty calculations, providing information pertaining run-time-to-empty to users, and/or providing alarms, to name a few.

In one or more embodiments, therapeutic gas source 116(*a*), 116(*b*) can be received by receptacle/gas supply subsystem 110(*a*), 110(*b*). To be received by receptacle/gas supply subsystem 110(*a*), 110(*b*), coupling member 114(*a*), 114(*b*) of therapeutic gas source 116(*a*), 116(*b*) may be required to mate with gas source coupling 115(*a*), 115(*b*) of receptacle/gas supply subsystem 110(*a*), 110(*b*). After being received, therapeutic gas source 116(*a*), 116(*b*) can be actuated (opened) thereby placing therapeutic gas source 116(*a*), 116(*b*) in fluid communication with gas pressure sensor 120(*a*), 120(*b*), which measures the pressure of the gas in therapeutic gas source 116(*a*), 116(*b*).

In exemplary embodiments, when received by therapeutic gas delivery system 100, gas source identifier reader 131(*a*), 131(*b*) can read gas source identifier 128(*a*), 128(*b*), which has recorded thereon the actual measured concentration of the therapeutic gas in gas source 116(*a*), 116(*b*) and/or the manufacturer's target gas concentration for therapeutic gas source 116(*a*), 116(*b*). Gas source identifier 128(*a*), 128(*b*) may also have recorded thereon additional data such as, but not limited to, the wetted volume of the gas source, the identity of the therapeutic gas, and/or its expiration date, to name a few. Data recorded on gas source identifier 128(*a*), 128(*b*) and gas pressure measured by gas pressure sensor 120(*a*), 120(*b*) can be communicated to therapeutic gas delivery system controller and stored in memory. In exemplary embodiments, at least some of the information recorded on gas source identifier 128(*a*), 128(*b*) can be used for run-time-to-empty calculations.

In one or more embodiments, gas source identifier 128(*a*), 128(*b*) may be radio-frequency identification (RFID) tags with read/write (R/W) memory in the communicating component, used to transmit data to the system controller(s) via an RFID reader 131(*a*), 131(*b*), bar codes and/or QR codes.

In various embodiments, gas source identifier reader 131(*a*), 131(*b*) may be an imaging device (e.g., camera) for reading and communicating actual gas concentration data on a QR code, or a barcode scanner for reading and communicating actual gas concentration data on a barcode. In one or more embodiments, gas source identifier reader 131(*a*), 131(*b*) may be a component of the bay or receptacle for the engagement of the therapeutic gas source in the therapeutic gas supply subsystem 110(*a*), 110(*b*). The bay or receptacle may further include means for correctly aligning the gas source within the bay or receptacle for reading the actual therapy gas concentration data. Corresponding means for aligning may be incorporated in the therapy gas source via imaging camera, or an RFID reader for reading and communicating actual gas concentration data on an RFID tag, where the tag may be unreadable if facing in the wrong direction. In certain embodiments, the means for aligning may include a keying arrangement between the gas source (e.g., via the gas source valve body) and the bay or receptacle receiver, or markings on the bay or receptacle and the gas source to be aligned upon placement of the gas source into the therapeutic gas delivery system. Such means for gas source alignment may also be used to prevent attachment of an incorrect gas source to the therapy gas delivery system.

In one or more embodiments, shut off valve 126(*a*), 126(*b*), which may be located downstream from and in fluid communication with the purge valve 124(*a*), 124(*b*), can provide a gas barrier between the gas supply subsystem 110(*a*), 110(*b*) and the primary delivery subsystem 140 and/or secondary delivery subsystem 160, and may block gas flow to therapeutic gas conduit(s) 101(*a*), 101(*b*). Shut off valve(s) 126(*a*), 126(*b*) may be binary valve(s). In one or more embodiments, a therapeutic gas conduit 101(*a*), 101(*b*) may provide a gas flow path (e.g., an enclosed gas flow path, tubing, channel, etc.) at least from the at least one gas supply subsystem to at least one primary gas delivery subsystem (e.g., primary delivery subsystem 140, etc.) and/or the at least one secondary gas delivery subsystem (e.g., secondary delivery subsystem 160).

In various embodiments, gas conduit pressure sensor 109 is connected to and in fluid communication with therapeutic gas conduit(s) 101(*a*), 101(*b*), is configured to measure a gas pressure in therapeutic gas conduit(s) 101(*a*), 101(*b*) being delivered to primary delivery subsystem 140 and/or secondary delivery subsystem 160, and/or is configured to be in communication, via a communication path, with a therapeutic gas delivery system controller. In various embodiments, gas pressure sensor 120(*a*), 120(*b*) is on the high pressure side (e.g., 3000 psi) of therapeutic gas pressure regulator 122(*a*), 122(*b*), while gas conduit pressure sensor 109 is on the regulated/downstream pressure side (e.g., 30 psi) of therapeutic gas pressure regulator 122(*a*), 122(*b*).

In one or more embodiments, with therapeutic gas source 116(*a*), 116(*b*) received by system 100, NO can be provided from either and/or both gas supply subsystem 110(*a*), 110(*b*) and, in turn, be fluidly communicated with first flow control channel 141(*a*) (e.g., a high flow control channel) and/or second flow control channel 141(*b*) (e.g., a low flow control channel) such that flow of the therapeutic gas (e.g., NO) can be controlled. In various embodiments, a high flow control channel may be configured to supply higher flow rates and thereby higher doses more accurately, whereas a low flow control channel may be configured to supply lower flow rates and thereby lower doses more accurately.

In exemplary embodiments, system 100 can automatically activate when dose set and injector module flow (e.g., inspiratory flow, forward flow, etc.) are above a pre-determined threshold, which would be flow rates indicative of an operational ventilator. By way of example, primary delivery subsystem 140 and/or secondary delivery subsystem 160 can automatically activate when dose set and injector module flow are determined to be above a pre-determined threshold. This can be accomplished, because, as noted above, the therapeutic gas delivery system controller (e.g., primary gas delivery subsystem controller 144 and/or secondary gas delivery subsystem controller 164, etc.) can be configured to communicate with first, second primary shut off valve 142(*a*), 142(*b*); first, second primary flow control valve 143(*a*), 143(*b*); first, second primary delivery flow sensor 146(*a*), 146(*b*); first, second primary confirmatory flow sensor 148(*a*), 148(*b*); secondary shut off valve 162, secondary medium flow control valve 163, secondary delivery flow sensor 166, and/or secondary confirmatory flow sensor 168, flow regulating valve 170, injector module delivery flow sensor 108(*a*), and/or injector module confirmatory flow sensor 108(*b*). In at least some instances, the first, second primary shut off valve 142(*a*), 142(*b*); first, second primary flow control valve 143(*a*), 143(*b*); first secondary shut-off valve 162, and first secondary flow control valve 163 are normally closed.

In various embodiments, primary delivery subsystem controller 144 may compare flow rate values received from first primary delivery flow sensor 146(*a*) and first primary confirmatory flow sensor 148(*a*) for the therapeutic gas, and may provide an alarm, recommend replacing at least one of the sensors, perform verification processes (described below in greater detail) to confirm which sensor is not functioning properly, and/or provide flow information from the functioning flow sensor, etc. if therapeutic gas flow rates measured at first primary delivery flow sensor 146(*a*) and first primary confirmatory flow sensor 148(*a*) differ from each other by greater than a threshold amount of about 10%, or about 7%, or about 5%, or about 2.5%, or about 2%, or about 1%, or about 0.5%.

In various embodiments, primary delivery subsystem controller 144 may compare flow rate values received from second primary delivery flow sensor 146(*b*) and second primary confirmatory flow sensor 148(*b*) for the therapeutic gas, and may provide an alarm, recommend replacing at least one of the sensors, perform verification processes (described below in greater detail) to confirm which sensor is not functioning properly, and/or provide flow information from the functioning flow sensor, etc. if therapeutic gas flow rates measured at second primary delivery flow sensor 146(*b*) and second primary confirmatory flow sensor 148(*b*) differ from each other by greater than a threshold amount of about 10%, or about 7%, or about 5%, or about 2.5%, or about 2%, or about 1%, or about 0.5%.

In exemplary embodiments, the arrangement of first, second primary delivery flow sensor 146(*a*), 146(*b*) and/or first, second primary confirmatory flow sensor 148(*a*), 148(*b*) provides monitoring of the primary delivery subsystem that may consist of at least 3 sets of sensors for triangulation of failure, including injector module delivery flow sensor 108(*a*) and/or injector module confirmatory flow sensor 108(*b*), first, second primary delivery flow sensor 146(*a*), 146(*b*) and/or first, second primary confirmatory flow sensor 148(*a*), 148(*b*), and therapeutic gas sensor 182, where flow rate values from the flow sensors can be compared, ratiometric calculations be performed and compared to the therapeutic gas sensor value to determine if any of these components have failed, or need service and/or calibration. Further, in at least some instances, therapeutic gas delivery system 100 can automatically perform verification processes (e.g., triangulation of failure, etc.) during delivery of therapeutic gas to a patient and/or if therapeutic gas sensor identifies a failed sensor, valve, or other component is identified then therapeutic gas delivery system 100 can use information from another sensor, valve, or other component that is functioning. By way of example, during delivery of therapeutic gas to a patient, therapeutic gas delivery system 100 can perform verification processes (e.g., triangulation of failure) and identify that a flow sensor is not functioning and therefor use flow information from a confirmatory flow sensors. Similar calculation and comparisons are described for a pre-use performance verification described herein.

Secondary Delivery Subsystem

In exemplary embodiments, at least some aspect of the present invention relate to systems, methods, and/or process for, amongst other things, providing therapeutic gas from one or more sources, providing therapeutic gas from a primary delivery subsystem, providing therapeutic gas from a secondary delivery subsystem, providing therapeutic gas from a primary and secondary delivery subsystem, providing therapeutic gas to a ventilated patient, and/or providing therapeutic gas to an assisted breathing apparatus, to name a few.

In exemplary embodiments, as described above, therapeutic gas delivery system 100 can include a plurality of delivery subsystems capable of receiving therapeutic gas from a plurality of sources and deliver the received therapeutic gas to a patient in need thereof using various techniques (e.g., delivery to injector module from primary delivery subsystem, delivery to injector module from secondary delivery subsystem, delivery to injector module from primary delivery subsystem and secondary delivery subsystem, delivery to an external manual ventilation device from secondary delivery subsystem, delivery to an external manual ventilation device from primary delivery subsystem, etc.). To accomplish at least the above, therapeutic gas delivery system 100 can include primary delivery subsystem 140, which may comprise two flow control channels and secondary delivery subsystem 160, which may comprise a secondary flow control channel, such that a therapeutic gas delivery system 100 comprises three redundant flow control channels in fluid communication with therapeutic gas conduit(s) 101(a), 101(b).

In exemplary embodiments, NO received from either and/or both gas supply subsystems can be in fluid communication with a secondary flow control channel 161(a) (e.g., a medium flow control channel) such that flow of NO can be controlled. Secondary flow control channel 161(a) can be in fluid communication with a secondary shut off valve 162, a secondary medium flow control valve 163, a secondary delivery flow sensor 166, and/or a secondary confirmatory flow sensor 168. Further, secondary flow control channel 161(a) can be in fluid communication with a flow regulating valve 170, which may be a 3-way valve that can control whether flow from the secondary gas delivery system 160 goes to injector module 107 or to outlet port 167 to another external manual ventilation device (e.g., bag valve mask). In various embodiments, secondary delivery subsystem 160 may have its own purge valve in fluid communication with flow control channel 161(a).

In exemplary embodiments, flow regulating valve 170 may be oriented (e.g., in reverse), so that at least one of the flow controllers in the primary gas delivery subsystem can back up the flow controller in secondary system. In various embodiments, flow regulating valve 170 can switch from being closed or delivering a therapeutic gas to the low pressure outlet 167 to delivering the therapeutic gas to the primary outlet and therapeutic gas delivery line 111 at the same dose as was being delivered by primary delivery subsystem 140.

In exemplary embodiments, the secondary delivery subsystem controller, primary delivery subsystem controller, and/or the system controller may detect problems (e.g. loss of communication with primary system) and, in at least some instances, respond to the detected problem. For example, delivery subsystem controller(s) 144 and/or 164 may detect a failure in one or more of the flow control channels of primary gas delivery system 140, automatically switch therapeutic gas flow control to a flow control channel of secondary delivery subsystem 160, and switch flow regulating valve 170 to deliver the therapeutic gas to primary outlet 172 and, in turn, to therapeutic gas delivery line 111. For another example, delivery subsystem controller(s) 144 and/or 164 may detect a failure in one of the two flow control channels of primary gas delivery system 140 and automatically switch from the failed therapeutic gas flow control to the other functioning flow control channel of primary gas delivery system 140 and/or change the flow of the functioning flow control channel to provide the desired set dose. Using at least the above technique the patient can be able stay on the ventilator with delivery at the same dose setting. For example, since the therapeutic gas is still delivered to therapeutic gas delivery line 111 and injector module 107, the gas analyzing subsystem still detects the amount of therapeutic gas being delivered by secondary delivery subsystem 160, and can display the amount to a user to allow continued monitoring of the delivered dose.

In various embodiments, secondary delivery subsystem 160 may have its own internal battery backup (not shown) separate from the main system battery (not shown). In various embodiments, two or more batteries may be able to power primary delivery subsystem 140 and secondary delivery subsystem 160, so in the event of a battery failure the other can be available.

In one or more embodiments, secondary delivery subsystem controller 164 and/or system controller may be configured to perform ratio-metric flow calculations for the concentration of therapeutic gas being delivered to the patient 203 based on the values from secondary delivery flow sensor 166 and/or secondary confirmatory flow sensor 168, and from injector module delivery flow sensor 108(a) and/or injector module confirmatory flow sensor 108(b), which measure ventilation flow rate in the breathing circuit or nasal cannula passing through the injector module. In exemplary embodiments, secondary delivery flow sensor 166 and/or secondary confirmatory flow sensor 168 provides monitoring of the secondary delivery subsystem that may consist of 3 sets of sensors for triangulation of failure, including injector module delivery flow sensor 108(a) and/or injector module confirmatory flow sensor 108(b), secondary delivery flow sensor 166 and/or secondary confirmatory flow sensor 168, and therapeutic gas sensor 182, where flow rate values from the flow sensors can be compared, the ratio-metric calculations done and compared to the therapeutic gas sensor value to determine if any of these components have failed.

In various embodiments, secondary delivery subsystem controller 164 may compare flow rate values received from secondary delivery flow sensor 166 and secondary confirmatory flow sensor 168 for therapeutic gas, and may provide an alarm, recommend replacing at least one of the sensors, perform verification processes (described below in greater detail) to confirm which sensor is not functioning properly, and/or provide flow information from the functioning flow sensor, etc. if the therapeutic gas flow rates measured at the secondary delivery flow sensor 166 and the secondary confirmatory flow sensor 168 differ from each other by greater than a threshold amount of about 10%, or about 7%, or about 5%, or about 2.5%, or about 2%, or about 1%, or about 0.5%.

In one or more embodiments, as described above, secondary gas delivery subsystem 160 also comprises two or more flow sensors 176, 174 along the gas flow path between the flow regulating valve 170 and a low pressure inlet port 165, where the two or more flow sensors 174, 176 are in fluid communication with each other and are located relative to each other in series, parallel, skewed, and/or any other configuration; pressure sensor 178 in fluid communication with the two or more flow sensors 174, 176, and/or low pressure outlet port 167. Further, the gas flow path from the inlet may intersect the gas flow path from the flow regulating valve 170 at blending junction 169. In various embodiments, secondary delivery flow sensor 166, and secondary confirmatory flow sensor 168 are in fluid communication with each other and are located relative to each other in series, parallel, skewed, and/or any other configuration.

In exemplary embodiments, secondary delivery subsystem 160 can automatically activate and/or deactivate when air/O2 flow (e.g., low pressure air/O2 from a wall outlet, from a compressor, etc.) is above a predetermined threshold and/or below a predetermined threshold. For example, if flow sensor(s) 176, 174 detect air/O2 flow rates greater than pre-set threshold (e.g. 0.5 SLPM for 2 seconds, flow rates indicative of wall flow, etc.) then secondary flow control valve 163 can automatically activate to deliver the set dose. Further, if flow sensor(s) 176, 174 detect air/O2 flow rates lower than pre-set threshold (e.g. 0 flow for 2 seconds) then secondary flow control valve 163 can automatically deactivate. Using at least the above, secondary delivery subsystem 160 can automatically activate and/or deactivate when a user (e.g., nurse, doctor, etc.) turns on and/or off air/O2 flow. In at least some instances, therapeutic gas delivery system 100, may alert the user of deactivation of NO delivery, for example, in case Air/O2 was mistakenly turned off and/or in case the low pressure tubing became disconnected from the secondary delivery system. Further, in exemplary embodiments, when flow is detected a prompt may be provided for the user to squeeze the bag valve mask a multiple times to perform a purge of the bag valve mask.

In exemplary embodiments, secondary delivery subsystem 160 can detect when and/or activate in response to squeezing of a valve mask bag. For example, manual activation may prompt the user to start air/O2 flow at wall flowmeter and may trigger a prompt to squeeze the bag valve mask multiple times to purge $NO_2$ (e.g., that may be generated as NO delivery can begin automatically in response to air/O2 flow detection, etc.) During each squeeze of the bag valve mask flow rates may be detected above a pre-set threshold (e.g., change in flow indicative of squeezing the bag valve mask) and secondary flow control valve 163 can automatically activate to deliver the set dose. Similarly, when no squeeze of the bag valve mask is detected (e.g., flow rates below a pre-set threshold indicative of no squeezing of the bag valve mask), then secondary flow control valve 163 can automatically deactivate to halt deliver of the set dose.

In exemplary embodiments, secondary delivery subsystem 140 can detect when a user (e.g., nurse, doctor, etc.) attached air/O2 flow (e.g., low pressure air/O2 from a wall outlet, from a compressor, etc.) incorrectly, for example, such that the bag valve mask is coupled to the inlet port rather than the outlet port and/or the air/O2 flow is coupled to the outlet port 167 rather than the inlet port 165 and, in at least some instances, provide an alert. For example, secondary delivery flow sensor 166, secondary confirmatory flow sensor 168, low pressure flow sensor 174, and/or low pressure confirmatory flow sensor 176 (e.g., bi-directional flow sensors) can detect air/O2 flow in reverse (e.g. hooked up backwards) and may provide an alarm if reverse flow is detected.

In exemplary embodiments, when the dose is set to 0, secondary gas delivery subsystem 160 can still automatically activate upon detection of activation conditions (e.g., such as those described above) and deliver default dose of 20 ppm NO when a system dose may be set to 0. In various embodiments, secondary gas delivery subsystem 160 dose may be set to a different dose than for the primary gas delivery subsystem 140, where a user may input separate doses for the primary gas delivery subsystem 140 and the secondary gas delivery subsystem 160. In various embodiments, secondary gas delivery subsystem 160 can detect elevated humidity or changes in gas density and compensate and/or provide an alarm.

In one or more embodiments, flow sensor 174 may be a low pressure delivery flow sensor and flow sensor 176 may be a low pressure confirmatory flow sensor. In various embodiments, secondary delivery subsystem controller 164 may compare the flow rate values received from low pressure delivery flow sensor 174 and low pressure confirmatory flow sensor 176 for the low pressure breathing gas, and may provide an alarm, recommend replacing at least one of the sensors, perform verification processes (described below in greater detail) to confirm which sensor is not functioning properly, and/or provide flow information from the functioning flow sensor, etc. if the breathing gas flow rates measured at the low pressure confirmatory flow sensor 176, and the low pressure delivery flow sensor 174 differ from each other by greater than a threshold amount of about 10%, or about 7%, or about 5%, or about 2.5%, or about 2%, or about 1%, or about 0.5%.

In exemplary embodiments, secondary delivery subsystem 160 can receive oxygen and/or air from a low pressure gas supply (e.g., from the low pressure outlet of a wall gas regulator, from a wall outlet, etc.) that can be wild stream blended with NO, for example, from gas supply subsystem A 110(*a*) and/or gas supply subsystem B 110(*b*) as described above, which in turn can be delivered to an assisted breathing apparatus (e.g., bag valve mask). In various embodiments, the low pressure gas supply may be a wall supply and/or a pressurized cylinder configured to provide air, oxygen, or a combination thereof. By way of example, to at least wild stream blend NO with oxygen and/or air (e.g., from the low pressure outlet of a wall gas regulator, from a wall outlet, etc.) NO received from either and/or both gas supply subsystems can be in fluid communication with secondary flow control channel 161(*a*) (e.g., a medium flow control channel) such that flow of NO can be controlled. Further, low pressure conduit 172 can receive low pressure oxygen and/or air (e.g., from the low pressure outlet of a wall gas regulator) via low pressure conduit pass through inlet port (e.g., coupled to a low pressure delivery conduit from the low pressure outlet of a wall gas regulator) and this received low pressure air can be wild stream blended with NO from either and/or both gas supply subsystems, for example at blending junction 169. Blending junction 169 may be configured to mix a therapeutic gas delivered by flow control channel 161(*a*) with a gas received at least one of the one or more inlet ports. Low pressure conduit 172 can be in fluid communication with low pressure oxygen/air received flow sensor 174, low pressure oxygen/air received confirmatory flow sensor 176, and/or low pressure oxygen/air received pressure sensor 178. Following the above example, flow regulating valve 170 can be actuated such that NO from secondary flow control channel 161 flows to blending junction 169 wherein the NO and oxygen and/or air can be wild stream blended, and in turn, this NO and air and/or oxygen can flow to the assisted breathing apparatus (e.g., bag valve mask, nasal cannula, etc.). In exemplary embodiments, a pressure relief valve 179 can be in fluid communication with low pressure conduit 172 to, for example, ensure that the pressure in low pressure conduit 172 is not above a predetermined threshold. In various embodiments, secondary delivery subsystem controller 164 may detect when pressure sensor 178 measures a pressure above or below a predetermined range, which may indicate a high pressure gas source has been attached to low pressure inlet port 165, or an assisted breathing apparatus (e.g., bag valve mask) has become disconnected from low pressure outlet port 167. Alarms may be provided when secondary delivery subsystem controller 164 detects that pressure sensor 178 measures a pressure above or below a predetermined range. Measured air/O$_2$ pass-thru flow rate may be displayed on display 102, 112(a), 112(b). Dosing and delivery info may be displayed on display 102, 112(a), 112(b) along with confirmation of delivery.

In exemplary embodiments, gas analyzer subsystem 180 can detect a failure of NO sensor 182, a nitrogen dioxide gas sensor 186, and/or an oxygen gas sensor 188, where the gas analyzer subsystem controller 184 may detect a failure of NO sensor 182 to ratio-metrically calculated value of NO concentration for one or more flow control channels. If a failure or error is detected at the gas analyzer, then rather than lose monitoring the therapeutic gas delivery system can display the ratio-metric delivered NO concentration from delivery or confirmatory sensors in place of the gas analyzer measured NO concentration and alert the user of the issue.

In at least some instances, gas analyzer subsystem 180 may require calibration before being operatively associated with an inspiratory line 213 and/or injector module 107 to sample therapeutic gas(es) and/or during delivery of therapeutic gas to a patient to ensure the gas analyzer subsystem 180 is functioning properly. For example, gas analyzer subsystem 180 can perform calibrations (e.g., baseline calibrations, span calibrations, etc.) of the gas sensor (e.g., catalytic type electrochemical gas sensor, etc.) by sampling and/or measuring the concentration of target gases in a controlled sample (e.g., baseline sample, span sample, etc.), where a span sample is a target gas (i.e., nitric oxide) with a specific known and controlled concentration within a range of interest (e.g., 10 PPM, 25 PPM, 50 PPM, 80 PPM, etc.) and/or where a baseline sample is a gas containing zero concentration of a target gas (i.e., conditioned ambient air containing zero nitric oxide). For example, a sample of ambient gas and/or span gas can be sampled via a sample line 119 that can be in fluid communication with valve 194. This gas sample can flow and/or be pulled to the gas sensors (e.g., NO sensor 182, etc.) wherein the flow can regulated via valve 194 (e.g., a three way valve, etc.) and/or sample pump 192. Sample line flow can be measured using flow sensor 190. A gas sample from ambient gas and/or span gas, via sample line 119, can flow and/or be pulled to the gas sensors (e.g., NO sensor 182). Flow in sample line 119 can be regulated via valve 194 (e.g., a three way valve, etc.) and/or sample pump 192. Sample line flow can be measured using flow sensor 190.

Therapeutic gas delivery system controller may be configured to execute a program or algorithm which calculates run-time-to-empty using the values received by the therapeutic gas delivery system controller and/or stored in memory from a temperature sensor 130(a), 130(b), a gas pressure sensor 120(a), 120(b), therapeutic gas pressure regulator 122(a), 122(b), flow sensor 146(a), 146,(b), 166, and gas source identifier reader 131 (therapy gas concentration, either actual or target). To obtain the run-time-to-empty value, the volume of therapeutic gas in the therapeutic gas source at a selected time-point during therapy may be calculated using the Boyle's Law or the Ideal Gas Law and the wetted volume of the therapeutic gas source. That is, using the temperature of the therapeutic gas, the therapeutic gas pressure, and the known wetted volume of the therapeutic gas source 116(a), 116(b), the pressure of water vapor at the measured temperature is subtracted from total gas source pressure to obtain the pressure of the dry therapeutic gas. Boyle's Law ($V_a = p_c V_c / p_a$) or the Ideal Gas Law (PV=nRT) is applied to calculate the volume in liters of the dry therapy gas at the measured temperature. In various embodiments, the run-time-to-empty may be calculate continuously to display changes in gas source pressure, intermittently, or when a delivery dose is set or changed to reflect changes in the run-time-to-empty for the new set dose.

In various embodiments, oscillating run-time-to-empty values may not be displayed. To avoid oscillating run-time-to-empty values being displayed intermittent recalculation may be implemented to avoid rapid changes in pressure and/or temperature, and allow a specific run-time-to-empty value to be displayed for a period of time sufficient for a user to read the run-time-to-empty value.

An average therapeutic gas consumption rate may be derived using data obtained from periodic and/or continuous measurements of a) average L/min. measured by the flow controller or commanded to the flow controllers over a period of time, b) average ventilation flow rate measured by BCG flow sensors 108(a) and/or 108(b) over a period of time, or c) set dose in ppm and an average ventilation flow rate measured by BCG flow sensors 108(a) and/or 108(b) over a period of time, which gives an average therapy gas flow rate in L/min. to be delivered.

By way of example, calculation of average therapeutic gas delivery/consumption rate using set dose and an average ventilation flow rate over a period of time is calculated as follows:

$$QNOset_{(n)} = \{YNOset/(YNOcyl - YNOset)\} \cdot Q_{i(n)} \text{ (SLPM)}$$

Where
QNOset=NO flow rate desired (SLPM)
$Q_i$=Injector Module flow rate (SLPM)
YNOset is the delivery set-point, the user set NO concentration value (ppm)
YNOcyl is NO cylinder concentration (ppm)
Run-time-to empty (RTE) for the selected time-point is then calculated from the volume of therapy gas in the therapy gas source and the consumption rate calculated by one of the above methods:

RTE=(Remaining cylinder volume−reserve volume−known purge sequences)/(average therapy gas consumption rate(primary+secondary)+known leak rate).

In exemplary embodiments, algorithms can be executed (e.g., using the above calculation) by system 100 which may be configured to leave some amount of gas pressure (i.e., gas volume) in the therapeutic gas source 116(a), 116(b), etc. (the "reserve volume") rather than running the gas source to empty. For example, the gas source can be a cylinder that may be deemed "empty" to the user when the cylinder pressure reaches 300 psi, 200 psi or 30 psi. This minimum pressure can be the minimum residual pressure needed for the regulator to function, plus pressure loss through valves, conduits, etc upstream of the pressure regulator, and/or plus pressure required for purging. Further, this can be used to compensate for delivery system 100 being configured to be for a therapeutic gas source that always has a pressure of at least, or more than, 30 psi. In various embodiments, runtime-to-empty calculations may also take into account use of therapeutic gas for anticipated purges due to for example a low set dose/flow rate.

In exemplary embodiments, the therapeutic gas delivery system controller may be configured to automatically reduce the delivery dose to conserve gas when run-time-to-empty calculations indicate the operating therapeutic gas source(s) 116(*a*), 116(*b*) is getting low and there is no back-up therapeutic gas source(s) 116(*a*), 116(*b*) available to supply the therapeutic gas at a sufficient pressure. Further, to provide the lower dose, the therapeutic gas delivery system 100 could ignore or bypass the minimum pressure threshold for the gas source, and continue delivering the therapeutic gas until the therapeutic gas source(s) 116(*a*), 116(*b*) is empty. In such instances, alarms may be provided. The above can be beneficial as a lower dose may be safer than discontinuation of therapy, therefore a reduced dose may be provided to the patient. In various embodiments, therapeutic gas delivery system controller may be configured to automatically reduce the delivery dose to conserve gas when high NO2 is detected to reduce the amount of NO available to react with $O_2$. In various embodiments, the therapeutic gas may be provided concurrently from two or more therapeutic gas source(s) 116(*a*), 116(*b*) to provide a larger total volume of therapeutic gas at the lower pressure(s) until empty.

In one or more embodiments, as described above, the therapeutic gas delivery system controller may communicate the calculated run-time-to-empty for the current set dose to a central display 102 and/or to a status display 112(*a*), 112(*b*) associated with a particular gas supply subsystem 110(*a*), 110(*b*) to notify the user of the run time remaining for the particular therapeutic gas source 116(*a*), 116(*b*) in a particular receptacle. When run-time-to-empty reaches predetermined levels, the therapeutic gas delivery system controller may also communicate modified alarms to the central display 102 and/or to a status display 112(*a*), 112(*b*) to indicate varying levels of criticality. For example a high level alarm may indicate that a half hour of run time remains, a moderate level alarm may indicate that an hour of run time remains, and a low level alarm may indicate that an hour and a half of run time remains. For another example, therapeutic gas delivery system controller may activate an audible alarm on the therapy gas delivery system or transmit an alarm to a wireless device (e.g., smart phone) to notify the user of remaining run-time. In one or more embodiments, a therapeutic gas delivery system comprising two or more therapeutic gas sources may supply therapeutic gas from the therapeutic gas source having the shorter run-time-to-empty value. In various embodiments, the therapeutic gas delivery system may seamlessly transition from a first therapeutic gas source to a second therapeutic gas source when the first therapeutic gas source has reached the intended run-time-to-empty value. In various embodiments, the calculated run-time-to-empty for the current set dose and/or the various alarm levels may be communicated to a hospital information system. Alarms may sound when the therapeutic gas delivery system 100 is operating on only one therapeutic gas source 116(*a*), 116(*b*). Alarms may be triggered based on the run-time-to empty value and/or therapeutic gas source 116(*a*), 116(*b*) pressure measured at gas pressure sensor 120(*a*), 120(*b*). Such alarms may be audible and/or visual. In at least some instances the run-time-to-empty can be the combined run-time-to-empty for both therapeutic gas sources, for example, depicted as one value and/or in any other visual format (e.g., graph, chart, image, etc.)

In various embodiments, display(s) 102, 112(*a*), 112(*b*), etc., may provide visual representation (e.g., graphical representation, bar graph, etc.) to a user visually indicating the remaining amount of therapeutic gas available from the therapeutic gas source 116(*a*), 116(*b*). This can be beneficial as the user can see when a therapeutic gas source 116(*a*), 116(*b*) will need to be replaced. A user may anticipate change-over from an active therapeutic gas source to a second (e.g., unused, full) therapeutic gas source by observing the actual RTE value, or visual representation, shown on display(s) 102, 112(*a*), 112(*b*). The visual representation may be displayed alongside the RTE value for each gas source, or instead of a RTE value when a dose is not set or flow through a flow control channel or an injector module 107 is not detected. In addition, an alarm may be provided when a therapeutic gas source is getting low, or the therapeutic gas delivery system 100 is down to only one operating therapeutic gas source. The therapeutic gas delivery system 100 may provide an alarm and/or instructions for the user to replace the depleted therapeutic gas source with a full therapeutic gas source. Displaying the actual RTE value(s) and/or visual indicators (e.g., bar graph, alarms, etc.) can allow the user to be aware of the remaining run time for the gas sources without having to look for the reading on a pneumatic pressure gauge attached to the gas source regulator and/or such visual displays can make monitoring the therapeutic gas delivery system 100 easier and help to avoid errors due to misreading various gauges and mechanical settings. Having one or more displays showing a run-time-to-empty value on the front of the system can mitigate problems associated with users having very little, or no, warning before the pressure supplied by a therapeutic gas source is unable to satisfy input pressure requirements for therapeutic gas pressure regulator 122(*a*), 122(*b*) and/or flow control valve(s) 143(*a*), 143(*b*), 163 and/or sensors. In various embodiments, the display(s) 102, 112(*a*), 112(*b*) may provide redundancy by being configured to allow a user to operate the therapeutic gas delivery system 100 from any of the displays 102, 112(*a*), 112(*b*), for example where each display is a touch screen that accepts user input.

In exemplary embodiments, implementation of two therapeutic gas sources 116(*a*), 116(*b*) provides redundancy, where second therapeutic gas sources 116(*b*) may supply therapeutic gas to a patient 203 when the first therapeutic gas sources 116(*a*) becomes depleted. For example, therapy gas delivery to the patient is initiated from therapy gas source 116(*a*) and delivered to the patient as described above. Further, as the run-time-to empty reaches a minimum value predetermined by the user and/or the system 100, therapeutic gas delivery system controller may close shut off valve 126(*a*) and open shut off valve 126(*b*) to source therapy gas delivery from second therapy gas source 116(*b*).

In one or more embodiments, therapeutic gas delivery system controller may automatically adjust for varying gas source concentrations when changing over from a first therapeutic gas source 116(*a*) to a second therapeutic gas source 116(*b*) containing the same therapeutic gas at a different concentration. By way of example, to accomplish the above gas source concentration information can be provided by gas source identifier 128(*b*), which can have recorded thereon the target and/or actual measured concentration of the therapeutic gas in therapeutic gas source 116(*b*). Further, as discussed above, gas source identifier 128(*b*) can also have recorded thereon additional data such as the identity of the therapy gas and/or its expiration date. In exemplary embodiments, use of the higher concentration therapeutic gas source may require system 100 increase in the average injector module 107 flow rate before delivery of the therapeutic gas would begin, or a reduction in therapeutic gas flow rate through flow control valve(s) 143(*a*), 143(*b*), 163, to maintain the same set dose to the patient 203. Similarly, injector module 107 flow rate may be reduced, and/or therapeutic gas flow rate through flow control valve(s) 143(*a*), 143(*b*), 163, may be increased to maintain the same set dose to the patient 203 for a lower therapeutic gas source 116(*b*) concentration.

If the therapeutic gases in therapeutic gas source 116(*a*) and therapeutic gas source 116(*b*) have different concentrations, therapeutic gas delivery system controller may automatically instruct a purge of the therapeutic gas delivery system, in which gas from the succeeding therapeutic gas source 116(*b*) is flushed through the high pressure side of the system, by opening purge valve 124(*b*) to evacuate all of the higher or lower concentration therapeutic gas from the manifold before opening second shut off valve 126(*b*) to the rest of the system, in addition to oxygen trapped that may form into NO2. In exemplary embodiments, purging to the atmosphere can be through a dedicated purge port in fluid communication with purge valve(s) 124(a), 124(*b*) to prevent exposure of the patient to purged gases (e.g., wrong concentration, contaminated, $NO_2$, etc.).

In exemplary embodiments, therapeutic gas delivery system controller may adjust parameters accordingly in the therapeutic gas delivery algorithm calculations to maintain the desired set dose taking into account the therapeutic gas concentration in therapy gas source 116(*b*). In at least some instances, if the therapeutic gas in the succeeding therapy gas source 116(*b*) is different from the therapeutic gas in therapeutic gas source 116(*a*), therapeutic gas delivery system controller may automatically orchestrate, instruct orchestration of, a purge of the therapeutic gas supply subsystem 110(*a*), 110(*b*) before opening shut off valve 126(*b*) to evacuate all of the preceding therapy gas from the remainder of the system. Therapeutic gas delivery system controller may then adjust parameters accordingly in the therapy gas delivery algorithm for therapy gas source 116(*b*) to deliver the correct set dose to the patient.

Pre-Use Verification Processes and/or Verification Processes

In exemplary embodiments, at least some aspect of the present invention relate to systems, methods, and/or process for, amongst other things, performing pre-use verifications by confirming the proper operation of a therapeutic gas delivery system 100, leaks, the proper functioning of the gas supply subsystem(s), gas delivery subsystem(s), and/or gas analyzer subsystem(s), and by extension the proper functioning of the valve(s), flow sensor(s), pressure sensor(s), detector(s), regulator(s), and/or subsystem controller(s), to name a few.

With respect to at least pre-use verifications of the present invention, some found previous pre-use procedures to be difficult and intimidating, and required extensive training. Exemplary embodiments of the present invention reduce and/or simplify the number and sequence of pre-use procedures and/or increases patient safety by eliminating and/or mitigating risks associated with previous pre-use procedures. For example, abnormalities and/or failures of elements of system 100 may result in sudden discontinuation of therapeutic gas and thereby a sudden removal of therapy to a patient, which can result in potential life threatening hazard (e.g., rebound hypertension); however, using systems, methods, and processes for, amongst other things, performing pre-use verifications can result in detection of an abnormality and/or failure during the pre-use performance verification test and mitigation of a potentially life threatening hazard. For example, detection of an abnormality and/or failure during the pre-use performance verification can effectively convert a potential hazard from the sudden removal of therapy to a delay of therapy (e.g., time to get another device), which can be much less severe.

Purging of system 100 may be important as air/$O_2$/contaminants may enter into components of system 100 configured to fluidly communicate NO. This can be problematic as NO may react with this air/$O_2$/contaminants, for example, generating NO2. These air/$O_2$/contaminants may enter system 100 via physical connection of therapeutic gas source 116(*a*), 116(*b*) to gas supply subsystem 110(*a*), 110(*b*), for example, trapping air/$O_2$/contaminants between the therapeutic gas source valve 117(*a*), 117(*b*) and the connection valve 118(*a*), 118(*b*).

In at least some instances, after properly receiving and/or verifying therapeutic gas source 116(*a*), 116(*b*), the therapeutic gas delivery system controller may initiate a purge sequence of the conduit/manifold between the therapeutic gas source valve 117(*a*), 117(*b*) and the closed shut off valve 126(*a*), 126(*b*), wherein the purged gas may exit the conduit/manifold via opened purge valve 124(*a*), 124(*b*). In various embodiments, a purge sequence may be initiated within a fraction of a second and/or within 2 seconds of detecting a properly received therapeutic gas source 116(*a*), 116(*b*). This purge may avoid the therapeutic gas from coming into prolonged contact with trapped air/$O_2$/contaminants introduced, for example, by the fluid connection between gas source valve 117(*a*), 117(*b*) and connection valve 118(*a*), 118(*b*).

In one or more embodiments, a conduit/manifold between connection valve 118(*a*), 118(*b*) and closed shut off valve 126(*a*), 126(*b*) may be purged by opening purge valve 124(*a*), 124(*b*) when therapeutic gas source 116(*a*), 116(*b*) is removed, for example, as indicated by gas source detector 132(*a*), 132(*b*). This purge may be used to reduce pressure between connection valve 118(*a*), 118(*b*) and closed shut off valve 126(*a*), 126(*b*), and/or evacuate stale gas from the manifold. As used herein, "stale" means that the therapeutic gas source may have reacted with air/$O_2$, unacceptable levels of $NO_2$ may have built up in the manifold, and/or other contaminants (e.g., $H_2O$, rust, etc.) may have entered the manifold or accumulated over time. The purge may lower the high pressure in the manifold back to just below a minimum cutoff of 200 PSI pressure (residual pressure), such that insertion of a new therapeutic gas source will trigger a higher pressure reading at gas pressure sensor 120(*a*), 120(*b*). Therapeutic gas delivery system 100 may not rely on gas pressure sensor 120(*a*), 120(*b*) to detect the presence of therapeutic gas source 116(*a*), 116(*b*) in fluid communication with the conduit/manifold 119(*a*), 119(*b*) because the response time of pressure sensor 120(*a*), 120(*b*) may be too slow to initiate a purge quickly enough to avoid gas reactions, and/or connection valve 118(*a*), 118(*b*) may have retained a gas pressure within conduit/manifold 119(*a*), 119(*b*) commensurate with the pressure in the mated therapeutic gas source 116(*a*), 116(*b*) that prevents a pressure change from being measured.

In one or more embodiments, purging sequences may be initiated, for example, by the therapeutic gas system controller, when therapeutic gas source 116(*a*), 116(*b*) is received (e.g., coupling member 114(*a*), 114(*b*) of therapeutic gas source 116(*a*), 116(*b*) mated with gas source coupling 115(*a*), 115(*b*); load handle (not shown) operatively manipulated; etc.) and/or during delivery of therapeutic gas to a patient.

Further to air/O$_2$/contaminants that may enter when therapeutic gas source 116(a), 116(b) is received (e.g., via physical connection of therapeutic gas source 116(a), 116(b) to gas supply subsystem 110(a), 110(b), etc.), low rates of NO consumption may trigger the need for purging sequences from the therapeutic gas source 116(a), 116(b) and all gas conduits/components in use. This build-up of NO$_2$ may also occur if oxygen permeation rate through the soft elastomer materials of conduits and/or seals is sufficient for NO gas volume moving through the system at a low rate to react causing the NO$_2$ conversion rate to increase. Conduit lengths, seals, and dead spaces may be reduced or eliminated to keep molecule of NO leaving the gas source and heading towards the patient circuit moving at the fastest rate practically possible to reduce dwell time. In at least some instances purging sequences may be more frequent when therapeutic gas consumption rates are low.

In at least some instances, purging sequences may be initiated during delivery of therapeutic gas to a patient because, for example, the delivery dose may be sufficiently low that the flow rate of therapeutic gas through one or more of the flow control channels is sufficiently low to allow a build-up of NO$_2$ on the high pressure side of shut off valve 126(a), 126(b), and/or the upstream side of primary flow control valve 143(a), 143(b), and/or secondary flow control valve 163. As described above, these purging sequences of the gas flow path to a vent (e.g., opened purge valve) removes the built-up NO$_2$ and other contaminants.

Similarly, purging sequences may be initiated when therapeutic gas delivery system 100, first gas supply subsystem 110(a) and/or second gas supply subsystem 110(b), have not been in use for a prolonged and/or predetermined amount of time (e.g., 10 min, 30 min, 1 hr, 6 hours, 12 hours, 24 hours, etc.). Purging sequences may utilize gas from a gas source (e.g., therapeutic gas source, etc.) and/or the purge may utilize pressurized gas contained between connection valve 118(a), 118(b) and a closed shut off valve 126(a), 126(b). Purging sequences described herein may be triggered upon detection of no therapeutic gas source, for example, as indicated by gas source detector 132(a), 132(b), load handle and/or gas source identification sensor 128(a), 128(b).

In various embodiments, purging sequences described herein may enable system 100 to maintain receptacle/gas supply subsystem 110(a), 110(b) primed for receiving therapeutic gas source 116(a), 116(b) and/or primed for seamlessly transition from one therapeutic gas source to another therapeutic gas source. As described above, seamless transition may be anticipated based on pressure and/or RTE calculation for the active (i.e., in use) therapeutic gas source 116(a), 116(b). Further, in exemplary embodiments, the duration and/or volume of gas used for purging sequences can be reduced (e.g., mitigate therapeutic gas waste, mitigate the amount of therapeutic gas purged/wasted into the surrounding environment, etc.). By way of example, orifices of the purge valves can be calibrated such that purge flow rates may be known, and therefore the volume of gas used for purging sequences can be dependent on purge valve open time.

In one or more embodiments, purging sequences may comprise a series of intermittent openings of purge valve 124(a), 124(b), and/or all of the flow control channel valves for a period of about 1 second to about 10 seconds followed by a period of about 1 second to about 10 seconds during which purge valve 124(a), 124(b), and/or all of the flow control channel valves, are closed. This intermittent opening and closing may be repeated 5, 10, 15, 20 times. In various embodiments, purging sequences may be increased to prime the therapeutic gas source for use more quickly, for example, by using the therapeutic gas in a continuous purge that may last from about 1 minute to about 10 minutes, or any time in between.

In one or more embodiments, therapeutic gas delivery system 100 may not power down until therapeutic gas sources 116(a), 116(b) are removed (e.g., released from receptacle/gas supply subsystem 110(a), 110(b), etc.). To at least prevent build-up of NO$_2$ and/or reduce waste of therapeutic gas, therapeutic gas delivery system 100 can require removal of therapeutic gas sources 116(a), 116(b) before shutting therapeutic gas delivery system 100 off. In at least some instances, an alarm may be provided until all therapeutic gas sources 116(a), 116(b) are removed. After removal of the therapeutic gas sources 116(a), 116(b), purging of the now empty bay(s) may be conducted, as described above. In various embodiments, a purge may not be initiated if the run-time-to-empty value indicates the therapeutic gas source is low (e.g., in a medium or high alarm state) in order to conserve therapeutic gas for delivery to the patient. In exemplary embodiments, when powered on, if therapeutic gas delivery system 100 detects a cylinder has been received the system can initiate a purge and/or alert.

In exemplary embodiments, purging sequences can be initiated to purge fluid pathways downstream of shut off valve 126(a), 126(b) such as conduits (e.g., conduit 101(a), 101(b), 172, etc.), flow control channels (e.g., flow control channels 141(a), 141(b), 161, etc.), and/or any other fluid pathways and/or components downstream of shut off valve 126(a), 126(b). By way of example, to purge downstream, shut off valve 126(a), 126(b) may be opened while purge valve 124(a), 124(b) is closed, enabling flow of therapeutic gas from the gas supply subsystem to at least one of the one or more flow control channels 141(a), 141(b), 161 and in turn to an egress from therapeutic gas delivery system 100 (e.g., purge valve, outlet from therapeutic gas delivery system 100, etc.). In various embodiments, primary delivery subsystem 140 and/or secondary delivery subsystem may include at least one purge valve in fluid communication with flow control channel 141(a), flow control channel 141(b), flow control channel 161(a), and/or at least one purge valve in fluid communication with injector module 107. In various embodiments, the corresponding shut off valves for each of the flow control channels may be selectively and/or sequentially opened and closed to purge the flow control channels. By way of example, when one flow control channel has been purged, the associated shut off valve 142(a), 142(b), 162, may be closed and the shut off valve for the next flow control channel may be opened.

In one or more embodiments, system 100 may perform pre-use verification procedures and/or during delivery of therapeutic gas to a patient for leaks by pressurizing, and/or prompting a user to install a therapeutic gas source, the gas supply subsystem at least between connection valve 118(a), 118(b) and closed shut off valve 126(a), 126(b) to a pressure above atmospheric pressure, monitoring the pressure between connection valve 118(a), 118(b) and closed shut off valve 126(a), 126(b) with gas pressure sensor 120(a), 120(b) for a predetermined time period, and presenting an alarm if the pressure between connection valve 118(a), 118(b) and closed shut off valve 126(a), 126(b) decreases greater than an expected amount over a predetermined time period (e.g., decrease in pressure due to a leak, etc.). In various embodiments, the predetermined time period may be a fixed time period, for example 30 seconds, 5 min, 10 min, 15 min, 20 min, 30 seconds or the time period may be between the initiation of a pre-use verification procedure and completion of the pre-use verification procedure, embodiments of which are described herein. In various embodiments, a greater than expected amount may be any drop in pressure over a short period (e.g., 5 min, 10 min, 15 min) or a drop in pressure larger than previously seen for a known leak-tight system and/or tested system for longer periods of time (e.g., 30 seconds, 20 min, 30 min, time for check-out, etc.).

In at least some embodiments, system 100 may perform checks for leaks within system 100, for example, during pre-use verification and/or when delivering therapeutic gas (e.g., when delivering therapeutic gas to a patient, etc.). Similar to checking for leaks between connection valve 118(*a*), 118(*b*) and closed shut off valve 126(*a*), 126(*b*), system leaks can be identified by pressurizing, and/or prompting a user to install a therapeutic gas source, the system to a known pressure (e.g., pressure above atmospheric pressure, etc.), opening and/or closing valves within system 100 and monitoring the pressure between the various open and/or closed valves with pressure sensors. Further, in at least some instances, system 100 may perform checks for leaks within system 100 when delivering therapeutic gas (e.g., background leak checks) by monitoring pressure sensors affiliated with system 100 for decreases in pressure that are greater than an expected amount over a predetermined time period.

In at least some embodiments, checks for leaks performed by system 100 may factor in the therapeutic gas used for pre-use verification from both gas sources, purging, etc.

In one or more embodiments, gas flow rate measured at each of delivery flow sensors 146(*a*), 146(*b*), 166 may be compared against the gas flow rate through confirmatory flow sensors 148(*a*), 148(*b*), 168 in series with delivery flow sensors 146(*a*), 146(*b*), 166 for the associated flow control channel. In various embodiments, an alarm, recommend replacing at least one of the sensors, perform verification processes (described below in greater detail) to confirm which sensor is not functioning properly, and/or provide flow information from the functioning flow sensor, etc. may be provided if there is a discrepancy between the gas flow rate through the delivery flow sensor and the gas flow rate through the confirmatory flow sensor, where a discrepancy greater than a threshold amount of about 10%, or about 7%, or about 5%, or about 2.5%, or about 2%, or about 1%, or about 0.5% triggers an alarm.

Aspect of the present invention relates to a method of confirming the proper functioning of gas delivery and injector module operation. In certain embodiments, therapeutic gas delivery system controller may further comprise an automated performance verifications during delivery of therapeutic gas and/or pre-use performance verification algorithm that purge at least a portion of therapeutic gas delivery system 100 upon installation of therapeutic gas source 116(*a*), 116(*b*) and/or during delivery of therapeutic gas, and verifies operability of selected components of therapeutic gas delivery system 100 before use (e.g., pre-use) and/or during use (e.g., during delivery of therapeutic gas).

In one or more embodiments, pre-use performance verification and/or performance verification during delivery of therapeutic gas can comprise the therapeutic gas delivery system controller comparing the concentration of the therapeutic gas reported by the gas analyzer 180 to the ratio-metric calculation(s) based on the flow rate values reported by flow sensors 146(*a*), 146(*b*), 166, 148(*a*), 148(*b*), 168 for each of flow control channels 141(*a*), 141(*b*), 161. A result of the comparison showing a different gas analyzer value for one flow control channel may indicate that the flow control valve, sensor, and/or component associated with that flow control channel is not functioning properly, whereas a different gas analyzer value compared to the ratio-metric value for all flow control channels may indicate that the therapeutic gas sensor is out of calibration. The use of redundant flow sensors 146(*a*), 146(*b*), 166, 148(*a*), 148(*b*), 168 in each of the flow control channels allows the system and/or user to pinpoint which component may not be functioning through cross checking. In this manner, it can be determined if a flow valve 143(*a*), 143(*b*), 163 needs calibration or the gas analyzer 180 needs high calibration. In various embodiments, gas analyzer values and/or ratio-metric values within pre-set tolerance (e.g. +−20% of set dose) can be considered an acceptable variation. The redundant ratio-metric calculations for flow control channels 141(*a*), 141(*b*), 161 can provide a basis to correct the output of the gas analyzer without the need for calibration gas if the ratio-metric calculations are all in agreement with one another. The difference between the calculated ratio-metric values and the measured gas analyzer value indicates the amount by which the gas analyzer is out of calibration. The output of the gas analyzer can then be compensated for. The gas analyzer 180 can references room air to prevent over-saturation during measurements. If a failure or error is detected at the gas analyzer, then rather than lose monitoring the device can display the ratio-metric delivered NO concentration from delivery or spy sensors in place of the gas analyzer measured NO concentration and alert the user of the issue.

Figure 5:
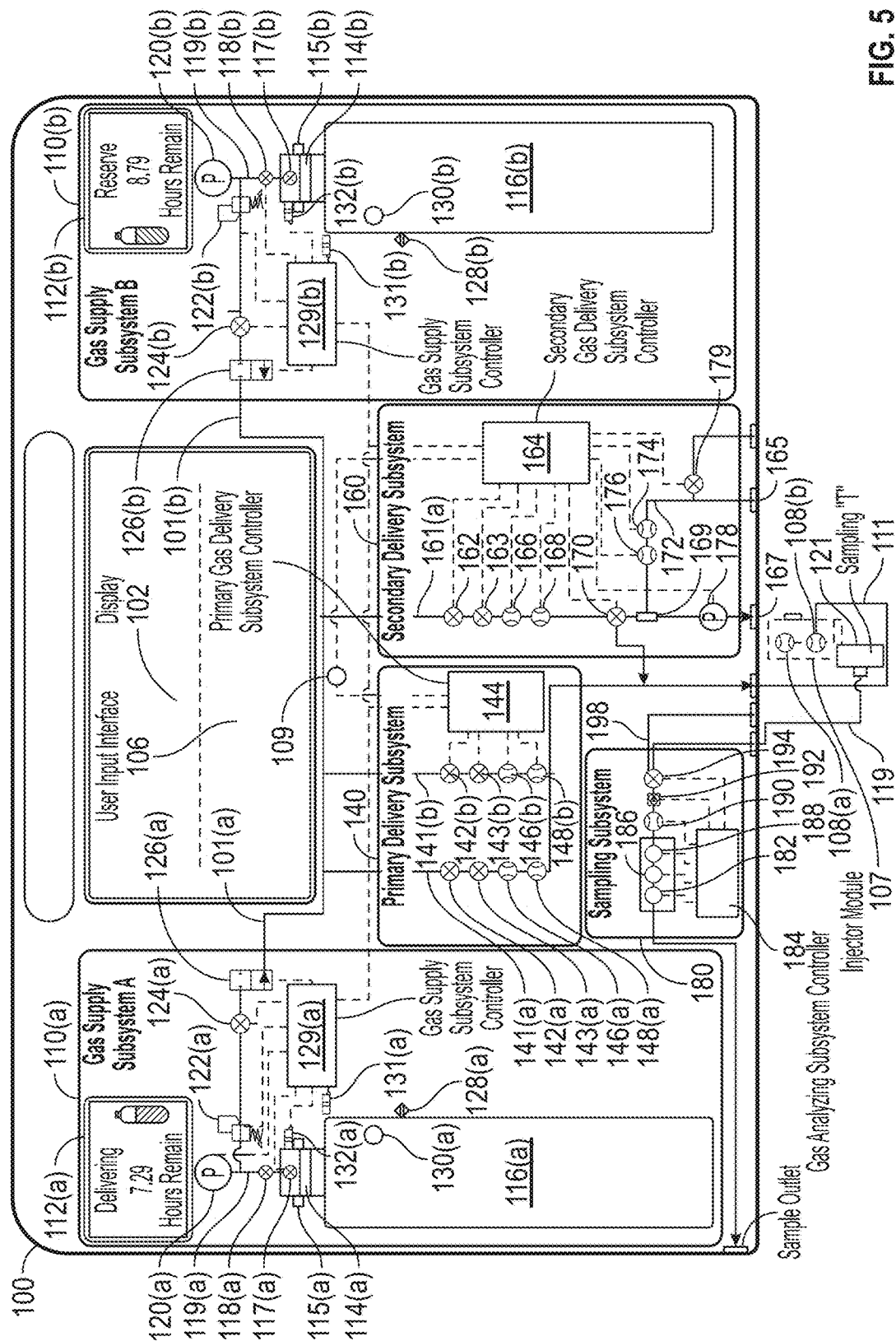
FIG. 5 is a diagram of an exemplary arrangement of a therapeutic gas delivery system for use during exemplary embodiments of a pre-use performance validation process.

In various embodiments, a user may be instructed to connect the injector module 107 with a particular orientation to the low pressure outlet port 167 to test the injector module and secondary delivery subsystem 160, as shown for example in FIG. 5. In various embodiments, an alarm, recommendation of replacing at least one of the sensors, perform verification processes (described below in greater detail) to confirm which sensor is not functioning properly, and/or flow information from the functioning flow sensor, etc. may be provided if the breathing gas flow rates measured at low pressure confirmatory flow sensor 176, low pressure delivery flow sensor 174, injector module confirmatory flow sensor 108(*b*), or injector module delivery flow sensor 108(*a*) differs from the other measured breathing gas flow rates by greater than a threshold amount, where the threshold amount may be a difference of about 10%, or about 7%, or about 5%, or about 2.5%, or about 2%, or about 1%, or about 0.5% between two measured flow rates, or between any one of the sensor measured values and the average flow rate. The threshold amount may depend on the accuracy and tolerances of the flow sensors used in the system.

In various embodiments, pre-use performance verification and/or performance verifications during delivery of therapeutic gas may further comprise adjusting flow control valve 163 to provide a stream of therapeutic gas at an intended therapeutic gas flow rate; and determining if flow control valve 163 is properly functioning, where the subsystem flow control valve is in fluid communication with the low pressure outlet port. In various embodiments, a subsystem flow control valve may be adjusted to be completely open to provide the stream of therapeutic gas at a maximum therapeutic gas flow rate.

In one or more embodiments, the combined therapeutic gas flow rate and breathing gas flow rate may be measured at injector module delivery flow sensor 108(*a*) and injector module confirmatory flow sensor 108(*b*) in fluid communication with low pressure outlet port 167; and three-way valve 170 may be switched to divert the stream of therapeutic gas to an alternative flow path, where the three-way valve is upstream from and in fluid communication with the low pressure outlet port, and the subsystem flow control valve is upstream from and in fluid communication with the three-way valve, to determine if three-way valve 170 functioned properly by determining if the combined therapeutic gas flow rate and breathing gas flow rate decreased by the therapeutic gas flow rate when the three-way valve was switched to the alternative flow path. In various embodiments, the breathing gas flow rate may be measured at injector module delivery flow sensor 108(*a*) and injector module confirmatory flow sensor 108(*b*). In an exemplary embodiment, flow control valve 163 may be set to the highest flow rate, and a step change (e.g., increase) can be observe on injector module delivery flow sensor 108(*a*) and injector module confirmatory flow sensor 108(*b*). When three-way valve 170 is switched to divert the gas flow from injector module 107, a decrease in gas flow rate can be detected downstream by injector module delivery flow sensor 108(*a*) and injector module confirmatory flow sensor 108(*b*). Similarly, when subsystem flow control valve 163 is set to a minimum or zero flow rate, a decrease in gas flow rate can be detected downstream by injector module delivery flow sensor 108(*a*) and injector module confirmatory flow sensor 108(*b*). This can be repeated several times.

In various embodiments, a flow rate may be measured at two or more secondary delivery subsystem flow sensors, wherein flow sensors 166, 168 are upstream from and in fluid communication with three-way valve 170; and the flow rates measured at each of the two or more subsystem flow sensors may be compared to determine if the two or more subsystem flow sensors are in agreement. In various embodiments, therapeutic gas blending ratio may be calculated from the measured flow rate measured by at least one of the two or more subsystem flow sensors and from the breathing gas flow rate measured by the low pressure delivery flow sensor; and comparing the calculated therapeutic gas blending ratio to the measured concentration of therapeutic gas exiting the injector module.

In various embodiments, each of the one or more shut off valves and/or flow control valves for each of the one of the one or more flow control channels may be selectively and/or sequentially opened and closed to confirm functionality and/or deliver a controlled flow of therapeutic gas to the injector module. In various embodiments, the gas analyzer confirms flow control channel(s) 141(*a*), 141(*b*) are functioning properly and providing the intended dose. Measurement of flow rates by redundant flow sensors can detect discrepancies between the flow controllers, flow sensors, and/or flow control channels. A purge of each flow control channel and delivery line 111 can also occur while the confirmation of flow control is being conducted. In various embodiments, the gas analyzer subsystem may reference room air while the purge is occurring.

In an alternative scenario the gas analyzer may be able to select to sample from within a pre-use verification port, so that the sample line does not need to be connected during performance verification.

In one or more embodiments, therapeutic gas may be delivered to the injection port of the injector module 107 through delivery line 111, a gas sample may be collected by sample-T 121 and directed to the gas analyzer to confirm the gas flow rate of therapeutic gas through flow control channel(s) 141(*a*), 141(*b*) provides an intended dose.

In various embodiments, system 100 can automatically compensate for different therapeutic gas source concentrations, for example, in response to pre-use verification. By way of example, system 100 can adjust flow valve 163 output during the performance verification to reduce the flow rate to half if the therapeutic gas source concentration is doubled.

In various embodiments, the system may instruct a user to disconnect the injector module from the low pressure outlet port and connect the injector module to ventilator breathing circuit 213. In various embodiments, the direction of gas flow from a ventilator through the injector module may be confirmed by bi-directional flow sensors 108(*a*), 108(*b*) of injector module 107.

In various embodiments, the system may instruct a user to disconnect the main electrical feed to therapeutic gas delivery system 100 to check that the backup battery is charged and functioning.

In various embodiments, the system may go through a post-use/shut-down verification procedure which may comprise relaying patient information data to the medical facility's information system.

In various embodiments, the system may prompt a user to remove therapeutic gas source(s) 116(*a*), 116(*b*), and verify that therapeutic gas source(s) 116(*a*), 116(*b*) have been removed through gas source detector 132(*a*), 132(*b*). At such time, the system may go through a shut-down purge as discussed above.

In various embodiments, the system may prompt a user to clean injector module 107 and/or provide instructions for cleaning injector module 107. In various embodiments, the system may prompt a user if the system is due for service.

One or more embodiments of the present invention provide an exemplary pre-use performance verification procedures, in which the following steps and/or procedures may be performed to ensure the proper functioning of a therapeutic gas delivery system 100; determine if there are leaks; ensure the proper functioning of the gas supply subsystem(s), gas delivery subsystem(s), and/or gas analyzer subsystem(s), and by extension the proper functioning of the valve(s), flow sensor(s), pressure sensor(s), detector(s), regulator(s), and/or subsystem controller(s). However, it is to be understood that any of these steps may be omitted or performed in a different order, or additional steps may be performed in addition those specifically indicated below. Furthermore, some of these steps may be performed concurrently, particularly if the steps are performed by components in separate subsystems and/or at least some of these steps may be performed during delivery of therapeutic gas to a patient.

Figure 4A:
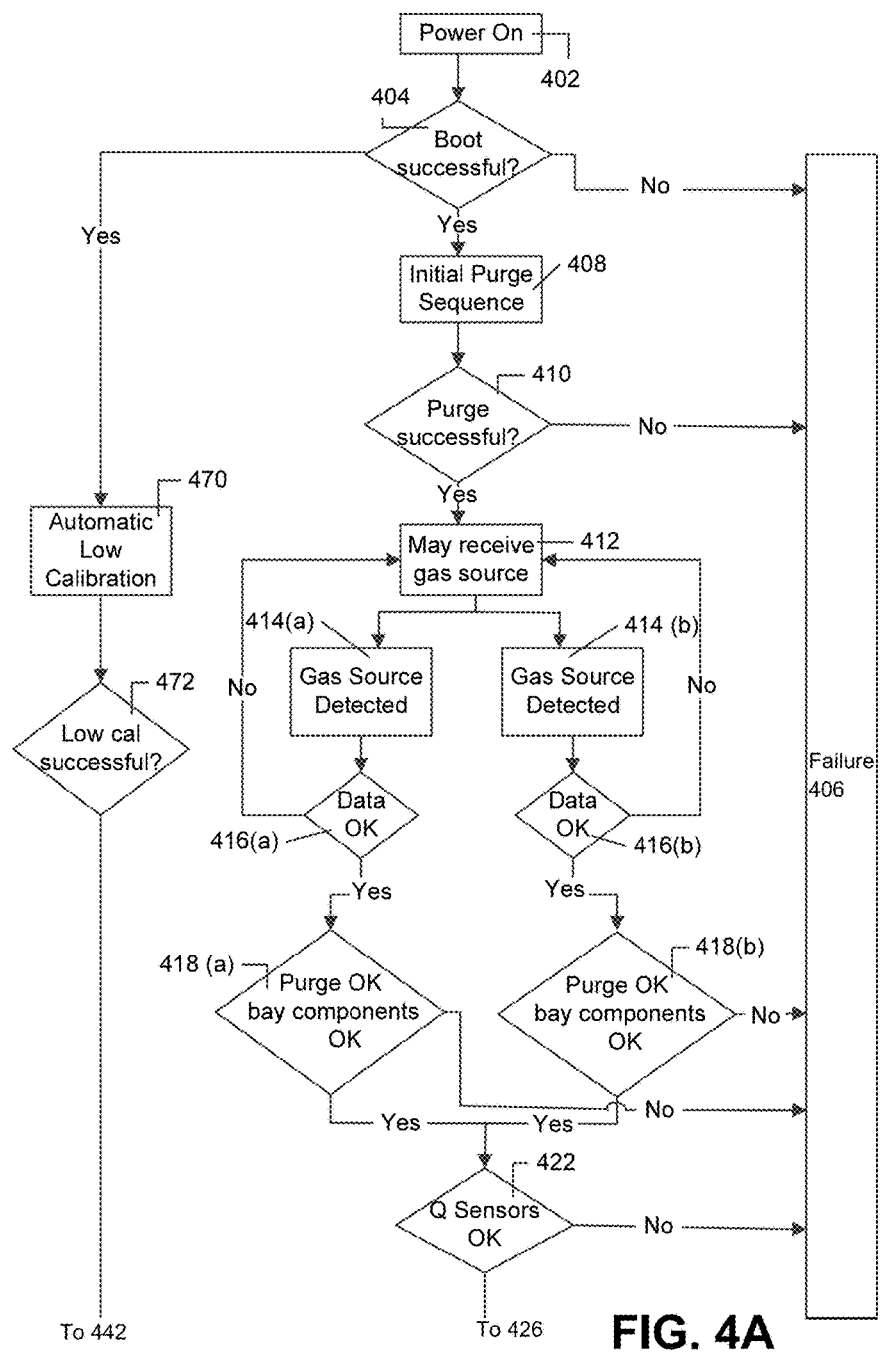
FIGS. 4A-4C is a flow chart of an exemplary pre-use performance validation process, in accordance with exemplary embodiments of the present invention.
Figure 4B:
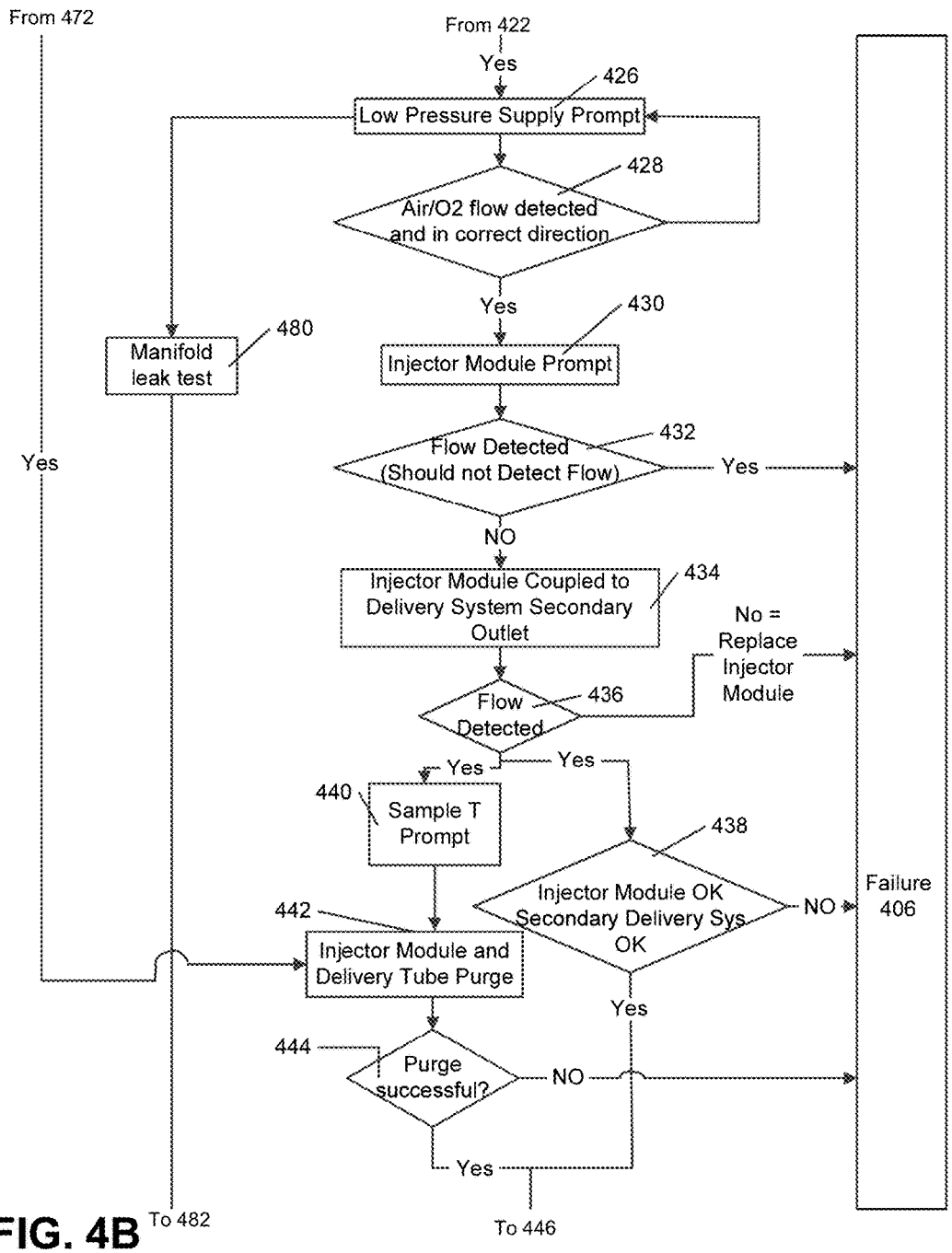
Figure 4C:
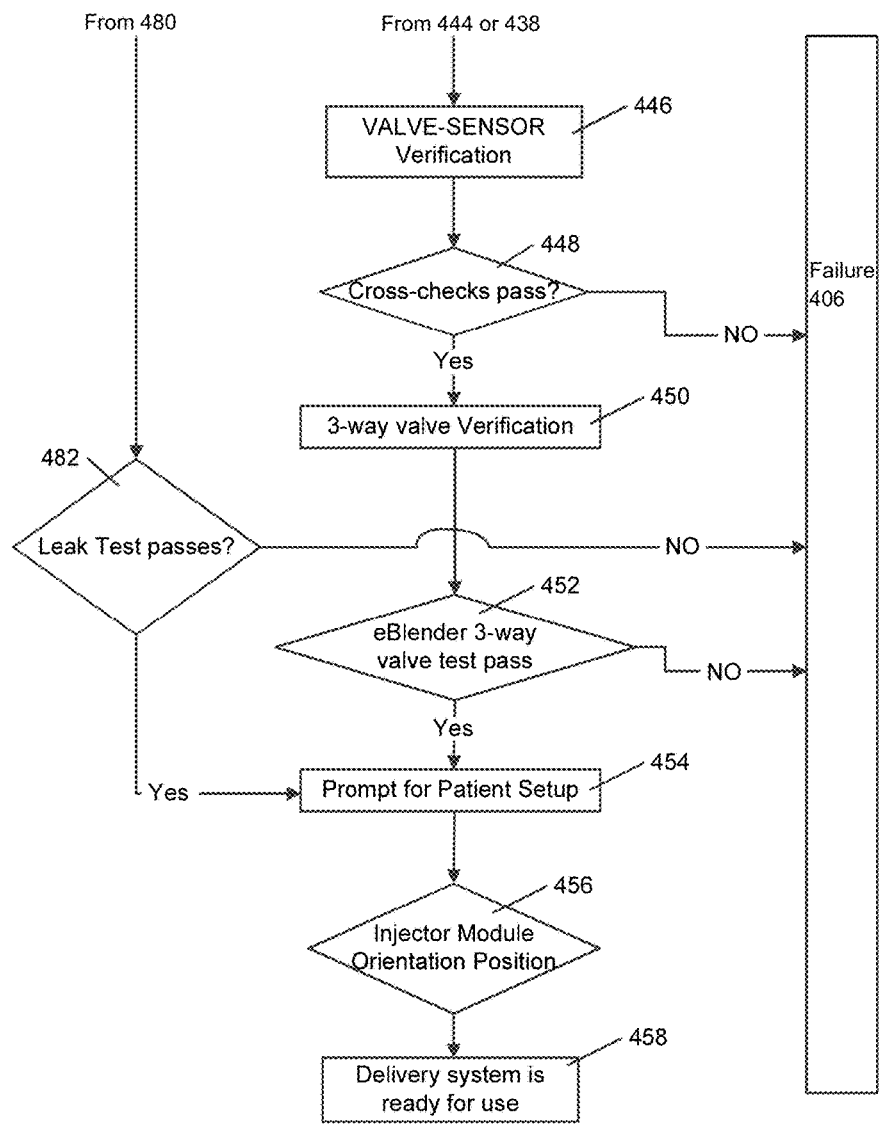

Referring to FIGS. 4A-4C, an exemplary pre-use performance verification procedure is depicted. At step 402, therapeutic gas delivery system 100 is started up (e.g., powered on by user, etc.). When started up, any and/or all subsystems (e.g., first gas supply subsystem 110(*a*), second gas supply subsystem 110(*b*), primary gas delivery subsystem 140, secondary gas delivery subsystem 160, and/or gas analyzing subsystem 180, etc.) can be booted up. At step 404, therapeutic gas delivery system 100 can confirm whether proper boot up of each subsystem occurred. If all subsystems properly boot then an initial purge sequence can begin, at step 408, and the purge can be verified as being successful, at step 410.

If any and/or all performance verifications process fail therapeutic gas delivery system 100 can undergo failure processes, at step 406, wherein therapeutic gas delivery system 100 can alarm the user (e.g., alarm provided on input interface 102, 106, alarm provided on displays 112(*a*), 112(*b*), etc.), log the failure (e.g., store information in memory affiliated with system 100, for example, in an error log), indicate the source of failure and/or recommend a course of action (e.g., change setup, change component, etc.), shut down system if failure is critical, continue the performance verification process, and/or allow delivery of therapeutic gas to the patient, to name a few.

In exemplary embodiments, an initial purge sequence can be initiated by system 100, wherein residual pressure gas and/or gas in system 100 can be purged (e.g., via purge valves, via outlets, etc.). Residual pressure and/or gas can be from therapeutic gas sources that were previously received by system 100. For example, previously received therapeutic gas sources may be from a previous use of system 100 and/or from a user inserting a therapeutic gas source prior to turning on therapeutic gas system 100. If the initial purge sequence was not successful, then therapeutic gas delivery system 100 can proceed to failure processes, at step 406. If the initial purge sequence is successful, therapeutic gas delivery system 100 may then receive the therapeutic gas source, at step 412, for example, as described above.

For ease, the exemplary pre-use performance verification procedures are depicted as being for two cylinders. This is merely for ease and is in no way meant to be a limitation. Similar techniques are envisioned for therapeutic gas delivery systems capable of receiving therapeutic gas from any number of sources.

At step 414(*a*), 414(*b*), received therapeutic gas sources can be detected by therapeutic gas delivery system 100 (e.g., using the techniques described above). In one or more embodiments, therapeutic gas source 116(*a*), 116(*b*) can be received by receptacle/gas supply subsystem 110(*a*), 110(*b*). To be received by receptacle/gas supply subsystem 110(*a*), 110(*b*), coupling member 114(*a*), 114(*b*) of therapeutic gas source 116(*a*), 116(*b*) may be required to mate with gas source coupling 115(*a*), 115(*b*) of receptacle/gas supply subsystem 110(*a*), 110(*b*). After being received, therapeutic gas source 116(*a*), 116(*b*) can be actuated (opened) thereby placing therapeutic gas source 116(*a*), 116(*b*) in fluid communication with gas pressure sensor 120(*a*), 120(*b*), which measures the pressure of the gas in therapeutic gas source 116(*a*), 116(*b*).

In one or more embodiments, therapeutic gas source 116(*a*), 116(*b*) may be automatically detected when a load handle (not shown) is operatively manipulated to release and/or lock therapeutic gas source 116(*a*), 116(*b*) with gas supply subsystem 110(*a*), 110(*b*) and/or gas source detector 132(*a*), 132(*b*) detects a therapeutic gas source. In various embodiments, gas source detector 132(*a*), 132(*b*) may be operatively associated with the load handle, where gas source detector 132(*a*), 132(*b*) detects when a load handle has been operatively manipulated. In various embodiments, gas source detector 132(*a*), 132(*b*) may be operatively associated with the gas source coupling 115(*a*), 115(*b*), where the gas source detector 132(*a*), 132(*b*) detects when matching coupling member 114(*a*), 114(*b*) of therapeutic gas source 116(*a*), 116(*b*) has been mated with the gas source coupling 115(*a*), 115(*b*).

At step 416(*a*), 416(*b*), data can be read in to confirm the correct cylinder has been received, for example, using the techniques described above. In exemplary embodiments, when received by therapeutic gas delivery system 100, gas source identifier reader 131(*a*), 131(*b*) can read gas source identifier 128(*a*), 128(*b*), which has recorded thereon the actual measured concentration of the therapeutic gas in gas source 116(*a*), 116(*b*) and/or the manufacturer's target gas concentration for therapeutic gas source 116(*a*), 116(*b*). Gas source identifier 128(*a*), 128(*b*) may also have recorded thereon additional data such as, but not limited to, the wetted volume of the gas source, the identity of the therapeutic gas, and/or its expiration date, to name a few. Data recorded on gas source identifier 128(*a*), 128(*b*) and gas pressure measured by gas pressure sensor 120(*a*), 120(*b*) can be communicated to therapeutic gas delivery system controller and stored in memory.

In various embodiments, the therapeutic gas delivery system controller may maintain shut off valve 126(*a*), 126(*b*) in a closed state until completion of verification analysis of the therapeutic gas source data, and keep therapeutic gas source closed off from the gas delivery subsystems downstream from shut off valve 126(*a*), 126(*b*) if incorrect information is detected (e.g. expired gas source, concentration out of range, wetted volume out of range, wrong therapeutic gas, etc.)

In one or more embodiments, the therapeutic gas delivery system controller may prompt a user to install a therapeutic gas source if an incorrect therapeutic gas source is received. By way of example, the presence of a correct or incorrect therapeutic gas source 116(*a*), 116(*b*) received by gas supply subsystem 110(*a*), 110(*b*) may be determined by analyzing therapeutic gas source data on and/or affiliated with gas source identifier 128(*a*), 128(*b*), which may be received by gas source identifier reader 131(*a*), 131(*b*). In exemplary embodiments, at any time during use (e.g., during pre-use verification procedures, during delivery of therapeutic gas to a patient, etc.), data (e.g., therapeutic gas source data) on and/or affiliated with gas source identifier 128(*a*), 128(*b*) can be analyzed, for example, by the therapeutic gas delivery system controller, to determine if the wrong therapeutic gas is coupled to the system, the therapeutic gas is expired, the therapeutic gas is the wrong concentration, the therapeutic gas source contains the correct therapeutic gas, the therapeutic gas is at sufficient pressure, etc.

In at least some embodiments, the therapeutic gas delivery system controller may prompt a user to install a therapeutic gas source if the received therapeutic gas source is determined to be empty and/or does not meet the minimum threshold (e.g., minimum threshold pressure). By way of example, the therapeutic gas delivery system controller may detect that gas supply subsystem 110(*a*), 110(*b*) is empty and/or does not meet the minimum threshold pressure using information communicated from gas pressure sensor 120(*a*), 120(*b*) indicative of the pressure of a received therapeutic gas source 116(*a*), 116(*b*).

In one or more embodiments, therapeutic gas delivery system 100 detects when a therapeutic gas source is installed and reads the affiliated information from the therapeutic gas source identifier attached to the gas source. In various embodiments, the therapeutic gas delivery system will confirm that the information from the therapeutic gas source identifier matches the expected identifier characteristics of the therapeutic gas. In exemplary embodiments, if the affiliated information from the therapeutic gas source identifier is found acceptable, the therapeutic gas delivery system may initiate a performance verification process during delivery of therapeutic gas.

At step 418(*a*), 418(*b*), after properly receiving and/or verifying therapeutic gas source 116(*a*), 116(*b*), the therapeutic gas delivery system controller may purge the system; verify the purge was successful by, for example, analyzing the concentration of the therapeutic gas and/or measuring the current detected through valves; and/or check all other related therapeutic gas delivery system components. If not successful and/or checks of other related components fail then therapeutic gas delivery system 100 can proceed to failure processes, at step 406.

At step 422, any and/or all flow sensors (e.g., flow sensors and corresponding confirmatory flow sensors, etc.) can be verified as no flow measurements should be seen because no gas flow has been initiated. If flow is measured (e.g., when no flow should be measured), therapeutic gas delivery system 100 can proceed to failure processes, at step 406, for example, as this can be indicative of a leak and/or sensor failure.

At step 426, therapeutic gas delivery system 100 can prompt users to attach a low pressure gas supply to the low pressure inlet port and, in at least some instances, set the low pressure gas supply flow to a known flow rate (e.g., 10 SLPM, etc.).

At step 428, flow can be detected and if flow is measured in the wrong direction (e.g., user attached low pressure supply to the low pressure outlet port, etc.) the user can be prompted re-attach the low pressure gas supply (e.g., returning to step 426). In exemplary embodiment, a flow of air/O$_2$ should be detected by the low pressure delivery flow sensor 174 and the low pressure confirmatory flow sensor 176. In various embodiments, the air/O$_2$ flow source to check the flow sensors 174, 176, 108(a), 108(b) may be air/O$_2$ from a regulated wall supply, a compressed gas cylinder supply, or a pump, which may be internal or external to the gas delivery system 100. A pump, regulated wall supply, or compressed gas cylinder supply may be connected and/or activated by user. A pump may provide waveforms to test the dynamic measurement range of the flow sensors. Bi-directional pass-thru sensors may verify correct setup of air/O$_2$ inlet connection for the performance verification.

In various embodiments, low pressure outlet port 167 is used for both connection to an assisted breathing apparatus for delivery of therapeutic gas and/or for connection of an injector module 107 for the pre-use verification procedure. Use of the same low pressure outlet port 167 for both functions provides a means to simplify (e.g, reducing and/or eliminating operator error, etc.) the pre-use verification procedures with fewer user steps for check-out of primary delivery, backup delivery and monitoring systems. Low pressure outlet port 167 may also serve as storage location for injector module 107 by providing a known and obvious location for the injector module to be located when not in use. In various embodiments, low pressure inlet port 165 and low pressure outlet port 167 may comprise connectors, for example quick disconnect gas connectors, hose barb connectors, and hose couplings, or the low pressure outlet port 167 comprise an adaptor configured and dimensioned to connect directly to the injector module. In various embodiments, a disposable and/or sterilizable adapter that connects to the injector module may be used to connect to low pressure outlet port 167 for the performance verification. This allows for separation of the device, which is not sterilized, and injector module 107 which may be sterilized.

At step 430, therapeutic gas delivery system 100 can prompt users to attach the injector module 107 such that, at step 432, no flow should be seen by injector module delivery flow sensor 108(a) and/or injector module confirmatory flow sensor 108(b). For example, the user may be prompted to place the injector module in electrical communication with therapeutic gas delivery system 100 while the injector module is not exposed to gas flow. If flow is detected by injector module delivery flow sensor 108(a) and/or injector module confirmatory flow sensor 108(b) the user may be instructed to replace the injector module as one of the flow sensors may be working improperly, for example, at step 406.

At step 434, therapeutic gas delivery system 100 can prompt users to attach the injector module 107 to low pressure outlet port 167, as depicted in FIG. 5, such that low pressure flow can be detected by at least injector module delivery flow sensor 108(a) and/or injector module confirmatory flow sensor 108(b), at step 436. For example, a user may be instructed to attach the injector module 107 to the low pressure outlet port for testing. If flow is not detected by injector module delivery flow sensor 108(a) and/or injector module confirmatory flow sensor 108(b) the user may be instructed to replace the injector module as one of the flow sensors may be working improperly, for example, at step 406. In various embodiments, the direction of gas flow through the injector module may be determined by bi-direction flow sensors 108(a), 108(b).

In one or more embodiments, performance verification can comprise attaching an injector module at low pressure outlet port 167; attaching a low pressure gas supply to low pressure inlet port 165, where the low pressure gas supply (e.g., regulated hospital wall outlet/external supply/cylinder) provides a flow of breathing gas at a breathing gas flow rate, and where the low pressure inlet port is in fluid communication with the low pressure outlet port; measuring the breathing gas flow rate from the low pressure gas supply at low pressure delivery flow sensor 174 and/or at low pressure confirmatory flow sensor 176, where low pressure delivery flow sensor 174 and low pressure confirmatory flow sensor 176 are in fluid communication with the low pressure inlet port and the low pressure outlet port; measuring the breathing gas flow rate from the low pressure gas supply at injector module delivery flow sensor 108(a) and/or injector module confirmatory flow sensor 108(b), wherein the injector module delivery flow sensor and the injector module confirmatory flow sensor are in fluid communication with low pressure outlet port 167; and determining if one of the breathing gas flow rates measured at low pressure confirmatory flow sensor 176, low pressure delivery flow sensor 174, injector module confirmatory flow sensor 108(b), or injector module delivery flow sensor 108(a) differs from the other measured breathing gas flow rates by greater than a threshold amount. Air/O2 flow rate may be in the range of about 0-60 SLPM, and may be detected as flowing in a forward direction. Placing the delivery flow sensors (e.g. injector module sensors and flow sensors) and confirmatory flow sensors in series facilitates detection of a single flow sensor in the fluid flow path that is not working and/or providing readings that do not match the others.

In exemplary embodiments, therapeutic gas delivery system 100 can determine when injector module 107 has been coupled to low pressure outlet port backwards. This can be accomplished because, amongst other things, the injector module delivery flow sensor and/or the injector module confirmatory flow sensor can be bi-directional flow sensors configured to determine the direction of gas flow through the injector module 107. In various embodiments, the injector module delivery flow sensor and the injector module confirmatory flow sensor are arranged in located relative to each other in series, parallel, skewed, and/or any other configuration.

At step 438, in exemplary embodiments, therapeutic gas delivery system 100 can deliver air/O2 through secondary delivery sub system 160 (e.g., received from a therapeutic gas source) to injector module 107 to at least verify injector module delivery flow sensor 108(a), injector module confirmatory flow sensor 108(b), flow sensor 174, and/or confirmatory flow sensor 176. In this configuration, the same flow of gas should be detected by each of injector module delivery flow sensor 108(a), injector module confirmatory flow sensor 108(b), flow sensor 174, and/or confirmatory flow sensor 176. If any flow sensors are found to not be functioning properly (e.g., measuring a different flow rate than two other flow sensors) then therapeutic gas delivery system 100 can undergo failure processes, at step 406.

By way of example, in exemplary embodiments, after performance verification has confirmed that injector module confirmatory flow sensor 108(b) and injector module delivery flow sensor 108(a) are both functioning properly, and low pressure delivery flow sensor 174 and low pressure confirmatory flow sensor 176 are both functioning properly, secondary delivery flow sensor 166 and secondary confirmatory flow sensor 168 may be tested. In various embodiments, the gas flow rate may be measured by secondary delivery flow sensor 166 and secondary confirmatory flow sensor 168 and compared to the incremental gas flow rate measured by injector module delivery flow sensor 108(a) and injector module confirmatory flow sensor 108(b).

At step 440, therapeutic gas delivery system 100 can prompt users to attach the gas sampling downstream from the injector module, as illustrated in FIG. 5. For example, a user may be instructed to attach a sample-T to the outlet of injector module 107, where the sample-T may divert at least a portion of the gas exiting injector module 107 to the gas sampling subsystem 180. The sample-T may be downstream from injector module 107 flow sensor(s) 108(a), 108(b).

At step 442, in various embodiments, flow of the therapeutic gas through one or more of flow control channels 141(a), 141(b), 161 may purge air out of delivery tube 111, injector module 107, and/or any conduits upstream from and/or in fluid communication with delivery tube 111 and/or injector module 107. For example, therapeutic gas delivery system 100 may purge delivery tube 111, injector module 107, and/or any conduits upstream from and/or in fluid communication with delivery tube 111 and/or injector module 107 by providing therapeutic gas from flow control channel 141(a) and/or any other flow control channel. In exemplary embodiments, during purges the gas analyzer may reference room air (e.g., mitigate exposure to high concentration NO, perform calibration, etc.).

At step 444, therapeutic gas delivery system 100 can confirm if the purge, at step 442, was successful by detecting the purge with any of the flow sensors in fluid communication with the conduit where the purge flowed therapeutic gas through and/or by taking a sample of the purge flow, via the sample T connected to the injector module, using the gas analyzing subsystem 180. If not successful then therapeutic gas delivery system 100 can proceed to failure processes, at step 406.

Figure 6:
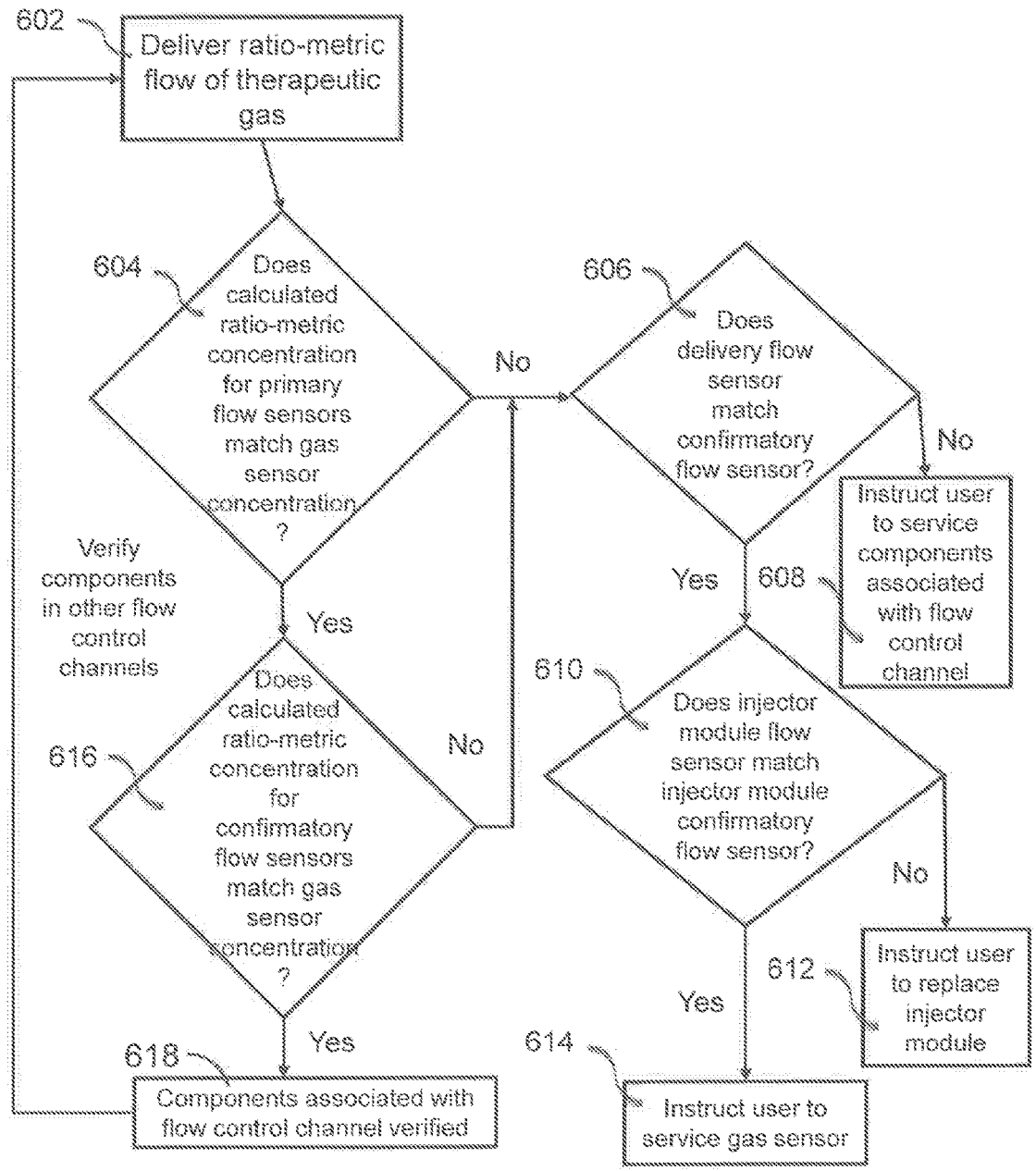
FIG. 6 is a flow chart of an exemplary process for determining whether various sensors are properly calibrated, in accordance with exemplary embodiments of the present invention.

At step 446, in exemplary embodiments, therapeutic gas delivery system 100 can perform verification processes of any and/or all flow sensors affiliated with first gas supply subsystem 110(a), a second gas supply subsystem 110(b), a primary gas delivery subsystem 140, a secondary gas delivery subsystem 160, and/or a gas analyzing subsystem 180. By way of example, referring to FIG. 6, one or more embodiments of the present invention provide an exemplary processes (e.g., triangulation of failure that can be used for pre-use performance verification, triangulation of failure that can be used for performance verification during delivery of therapeutic gas, etc.) for determining whether various sensors are properly calibrated by cross-checking with other sensors.

At step 602, the therapeutic gas delivery system 100 delivers a ratio-metric flow of therapeutic gas according to a dose set by the user or according to a predetermined dose that is part of the pre-use performance verification procedure. Of course, similar techniques can be used for performance verification during delivery of therapeutic gas. The ratio-metric flow can be provided by the components in fluid communication with first primary flow control channel 141(a) (e.g. first primary control valve 143(a), first primary delivery flow sensor 146(a) and first primary confirmatory flow sensor 148(a)), the components in fluid communication with second primary flow control channel 141(b) (e.g. second primary control valve 143(b), second primary delivery flow sensor 146(b) and second primary confirmatory flow sensor 148(b)), the components in fluid communication with secondary flow control channel 161(a) (e.g. secondary flow control valve 163, secondary delivery flow sensor 166, and secondary confirmatory flow sensor 168)), etc. In one or more embodiments, components associated with one flow control channel is operated and verified, followed by operation and verification of a second set of components, followed by operation and verification of a third set of components, etc., until all relevant components have been verified.

At step 604, the primary delivery subsystem controller 144 and/or secondary gas delivery subsystem controller 164 compares the NO concentration measured by gas sensor 182 to the ratio-metric concentration calculated using the therapeutic gas flow reported by the delivery flow sensor 146(a), 146(b), 166, the NO concentration in the gas cylinder, the breathing gas flow reported by injector module delivery flow sensor 108(a), and/or flow sensor 174, 176. By way of example, the ratio-metric concentration for a given set of sensors is calculated as follows:

$$YNOcalc=(QNOmeas \cdot YNOcyl)/(QNOmeas+Q_i)$$

Where
YNOcalc=calculated ratio-metric NO concentration (ppm)
QNOmeas=measured NO flow rate (SLPM)
YNOcyl=NO cylinder concentration (ppm)
$Q_i$=injector module flow rate (SLPM)

In the above equation, QNOmeas can be provided by first primary delivery flow sensor 146(a), second primary delivery flow sensor 146(b), first primary confirmatory flow sensor 148(a), second primary confirmatory flow sensor 148(b), secondary delivery flow sensor 166 or secondary confirmatory flow sensor 168, and $Q_i$ can be provided by injector module delivery flow sensor 108(a), injector module confirmatory flow sensor 108(b), flow sensor 174 or flow sensor 176, depending on which flow sensors are being verified.

If the calculated ratio-metric concentration does not match the NO concentration measured by gas sensor 182, then the flow information from delivery flow sensor 146(a), 146(b), 166 is compared to the flow information from its respective confirmatory sensor 148(a), 148(b), 168 at step 606. If the flow information from delivery flow sensor 146(a), 146(b), 166 does not match the flow information from confirmatory sensor 148(a), 148(b), 168, then step 608 provides that the user can be instructed to service the components in fluid communication with the flow control channel being verified, which includes the delivery flow sensor 146(a), 146(b), 166, the respective confirmatory sensor 148(a), 148(b), 168 and/or respective the control valve 143(a), 143(b), 163. Furthermore, if during therapy, the device can fail over to an alternate flow control channel or secondary delivery subsystem. If the flow information from delivery flow sensor 146(*a*), 146(*b*), 166 matches the flow information from confirmatory sensor 148(*a*), 148(*b*), 168, then the flow information from injector module delivery flow sensor 108(*a*) or flow sensor 174 is compared to the flow information from injector module confirmatory flow sensor 108(*b*) or flow sensor 176 at step 610. If the flow information injector module delivery flow sensor 108(*a*) or flow sensor 174 does not match the flow information from injector module confirmatory flow sensor 108(*b*) or flow sensor 176, then step 612 provides that the user can be instructed to replace the injector module 107. Furthermore, if during therapy, in one or more embodiments the device can use confirmatory flow sensor 108(*b*) for flow control and/or delivery. If the flow information from injector module delivery flow sensor 108(*a*) or flow sensor 174 matches the flow information from injector module confirmatory flow sensor 108(*b*) or flow sensor 176, then step 614 provides that the user can be instructed to service (e.g. calibrate, replace) gas sensor 182 and/or the device can display the ratio-metric calculated concentrations to the user.

If the calculated ratio-metric concentration matches the NO concentration measured by gas sensor 182, then the primary delivery subsystem controller 144 and/or secondary gas delivery subsystem controller 164 compares the NO concentration measured by gas sensor 182 to the ratio-metric concentration calculated using the therapeutic gas flow reported by the confirmatory sensor 148(*a*), 148(*b*), 168, the NO concentration in the gas cylinder, and the breathing gas flow reported by injector module confirmatory flow sensor 108(*b*) or flow sensor 176 at step 616.

If the calculated ratio-metric concentration for the confirmatory sensors does not match the NO concentration measured by gas sensor 182, then the flow information from delivery flow sensor 146(*a*), 146(*b*), 166 is compared to the flow information from its respective confirmatory sensor 148(*a*), 148(*b*), 168 at step 606. If the flow information from delivery flow sensor 146(*a*), 146(*b*), 166 does not match the flow information from confirmatory sensor 148(*a*), 148(*b*), 168, then step 608 provides that the user can be instructed to service the components in fluid communication with the flow control channel being verified, which includes the delivery flow sensor 146(*a*), 146(*b*), 166, the respective confirmatory sensor 148(*a*), 148(*b*), 168 and/or respective the control valve 143(*a*), 143(*b*), 163. Furthermore, if during therapy, the device can fail over to an alternate flow control channel or secondary delivery subsystem. If the flow information from delivery flow sensor 146(*a*), 146(*b*), 166 matches the flow information from confirmatory sensor 148(*a*), 148(*b*), 168, then the flow information from injector module delivery flow sensor 108(*a*) or flow sensor 174 is compared to the flow information from injector module confirmatory flow sensor 108(*b*) or flow sensor 176 at step 610. If the flow information from injector module delivery flow sensor 108(*a*) or flow sensor 174 does not match the flow information from injector module confirmatory flow sensor 108(*b*) or flow sensor 176, then step 612 provides that the user can be instructed to replace the injector module 107. Furthermore, if during therapy, in one or more embodiments the device can use confirmatory flow sensor 108(*b*) for flow control and/or delivery. If the flow information from injector module delivery flow sensor 108(*a*) or flow sensor 174 matches the flow information from injector module confirmatory flow sensor 108(*b*) or flow sensor 176, then step 614 provides that the user can be instructed to service (e.g. calibrate, replace) gas sensor 182 and/or the device can display the ratio-metric calculated concentrations to the user.

If the calculated ratio-metric concentration for the confirmatory sensors matches the NO concentration measured by gas sensor 182, then the components in fluid communication with the flow control channel are successfully verified as provided at step 618. The components in fluid communication with the other flow control channels can then be verified by starting at step 602. Once all relevant components have been verified, then the performance verification can proceed further as provided by FIGS. 4A-4C.

Referring back to FIGS. 4A-4C, at step 448, if any and/or all performance verification processes, at step 446, were not successful then therapeutic gas delivery system 100 can proceed to failure processes, at step 406. If successful then performance verification processes can verify three-way 171, at step 450.

Therapeutic gas delivery system 100 can verify flow regulating valve 170, which may be a three-way valve 170 by actuating it such that an initial flow rate (e.g., zero flow) is delivered to the injector module; actuating valve 170 so another set flow rate (e.g. 1 SLPM) is delivered to the injector module; detecting the change seen at the injector module using injector module delivery flow sensor 108(*a*) and/or injector module confirmatory flow sensor 108(*b*); and/or then actuating three way valve 170 such that the initial flow rate (e.g., zero flow) returns.

By way of example, therapeutic gas delivery system 100 can verify three-way valve 170 by actuating the three way valve to deliver low pressure air/O2 at an initial flow rate (e.g., wall flow 10 SLPM); then actuating three way valve 170 to deliver therapeutic gas through secondary delivery subsystem 160, via flow control channel 161, at secondary delivery flow rate (e.g. 1 SLPM); detecting the incremental change seen at the injector module using injector module delivery flow sensor 108(*a*) and/or injector module confirmatory flow sensor 108(*b*) (e.g., flow increase of about 10%); and/or then actuating three way valve 170 such that the therapeutic gas flow, NO, flows to 111, and is delivered downstream to the injector module flow sensors and the initial flow rate (wall flow 10 SLPM) returns (e.g., as the incremental NO flow is no longer measured by the injector module flow sensors). In at least some instances, during verification of three-way valve 170, the gas analyzer may be exposed to room air, for example, to prevent over-saturation of NO sensor (e.g., from 4880 ppm high concentration).

At step 452, if any and/or all performance verification processes, at step 450, were not successful then therapeutic gas delivery system 100 can proceed to failure processes, at step 406. If successful then performance verification processes prompt the user to connect the injector module and/or sample T to the patient breathing circuit (e.g., as depicted in FIGS. 1-3) and/or connect the external manual ventilation device (e.g., bag valve mask) to outlet 170, at step 454.

At step 456, therapeutic gas delivery system 100 can verify injector module 107 is facing the correct direction and/or in the correct position in the breathing circuit.

In exemplary embodiments, therapeutic gas delivery system 100 can determine when injector module 107 has been inserted into a breathing circuit 209 backwards. This can be accomplished because, amongst other things, the injector module delivery flow sensor and/or the injector module confirmatory flow sensor can be bi-directional flow sensors configured to determine the direction of gas flow through the injector module 107. In various embodiments, the injector module delivery flow sensor and the injector module confirmatory flow sensor are arranged in located relative to each other in series, parallel, skewed, and/or any other configuration.

In various embodiments, the system may guide a user through system setup at the bedside (e.g., at the bedside of a patient and/or intended patient, etc.), which may comprise providing instructions on secondary delivery subsystem connections (e.g. attachment of a valve-mask assembly), injector module 107 connections into the breathing circuit and verify the correct orientation, humidity/temp levels, etc., and on sample T placement in the breathing circuit. In various embodiments, the bi-directional flow sensors in the injector module may indicate gas flow direction and verify the correct orientation to the user.

If injector module 197 is oriented such that it is not facing the correct direction, system 100 may prompt the user to re-position injector module 107 such that it is facing the correct direction.

At step 458, if the injector module is positioned properly in the breathing circuit, therapeutic gas system 100 can then be ready for use (e.g., ready to delivery therapeutic gas to a patient).

In exemplary embodiments, at any time during use of therapeutic gas delivery system 100, the gas analyzer and/or system 100 can initiate a low calibration, at step 470, as described above. For ease, step 470 is shown as occurring after step 404. This is merely for ease and is in no way meant to be a limitation. At step 472, if the low calibration is not successful then therapeutic gas delivery system 100 can retry the low calibration and/or proceed to failure processes, at step 406. If the low calibration is successful it then the sensor is calibrated and may be used during delivery of therapeutic gas to a patient and/or during any relevant steps in the pre-use verification processes (e.g., step 442, etc.).

In exemplary embodiments, at any time during use of therapeutic gas delivery system 100, system 100 can initiate a manifold leak test, at step 480, as described above. At step 482, if the manifold leak test is not successful then therapeutic gas delivery system 100 can proceed to failure processes, at step 406. If the manifold leak test is successful it then the manifold may be used during delivery of therapeutic gas to a patient and/or during any relevant steps in the pre-use verification processes (e.g., step 454, etc.).

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

It is to be understood that the invention is not limited to the details of construction or process steps set forth in the above description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "an embodiment" in various places throughout this specification are not necessarily referring to the same embodiment of the invention. Furthermore, the particular features, structures, materials, or characteristics may be combined in any suitable manner in one or more embodiments.

What is claimed is:

1. A method of confirming the proper functioning of a therapeutic gas delivery system, comprising:
    mating a therapeutic gas source to a gas source coupling;
    opening a shut off to deliver a flow of therapeutic gas from a gas supply subsystem to a gas delivery subsystem comprising one or more flow control channels comprising at least one shut off valve, at least one delivery flow sensor, and at least one confirmatory flow sensor to purge the gas supply subsystem and the at least one of the one or more flow control channels;
    pressurizing the gas supply subsystem at least between a connection valve and a closed shut off to a pressure above atmospheric pressure;
    monitoring the pressure between the connection valve and the closed shut off valve with a gas pressure sensor for a predetermined time period; and
    presenting an alarm if the pressure between the connection valve and the closed shut off valve decreases or increases more than an expected amount over the predetermined time period.

2. The method of claim 1, which further comprises mating a therapeutic gas source to a gas source coupling; and
    opening a purge valve in fluid communication with the connection valve, and between the closed shut off and the connection valve to flush gas within the gas supply subsystem with gas from the mated therapeutic gas source.

3. The method of claim 1, which further comprises reading a gas source identifier attached to the therapeutic gas source with a gas source identifier reader, wherein the gas source identifier contains information at least of the identity, expiration date, and the concentration of the therapeutic gas supplied by the therapeutic gas source.

4. The method of claim 1, which further comprises selectively opening the shut off valve for a first flow control channel of the one or more flow control channels, while the shut off valve for each of any other of the one or more flow control channels is closed; and measuring the gas flow rate through the at least one delivery flow sensor, and the at least one confirmatory flow sensor of the first flow control channel.

5. The method of claim 4, which further comprises sequentially opening the shut off valve for each of the other of the one or more flow control channels by selectively opening the shut off valve for a second flow control channel, and closing the shut off valve of the first flow control channel.

6. The method of claim 4, which further comprises comparing the gas flow rate through the at least one delivery flow sensor with the gas flow rate through the at least one confirmatory flow sensor of the first flow control channel; and presenting an alarm if there is a discrepancy between the gas flow rate through the at least one delivery flow sensor and the gas flow rate through the at least one confirmatory flow sensor.

7. A method to ensure the proper functioning of a therapeutic gas delivery system, comprising:
    detecting a therapeutic gas source mated with a therapeutic gas supply subsystem;
    providing an initial purge of the therapeutic gas supply subsystem and one or more flow control channels within a gas delivery subsystem with gas from the therapeutic gas source by delivering a flow of therapeutic gas from the gas supply subsystem to at least one of the one or more flow control channels comprising at least one shut off valve, at least one delivery flow sensor, and at least one confirmatory flow sensor;

maintaining a shutoff valve down stream from the therapeutic gas source in a closed state;

verifying that no flow is detected by one or more flow sensors down stream from the shutoff valve; and determining if flow is detected by one or more flow sensors down stream from the shutoff valve; and providing an alert if flow is detected by one or more flow sensors down stream from the shutoff valve.

8. The method of claim 7, which further comprises reading information associated with the therapeutic gas source to determine the identity, concentration, and/or expiration date of the therapeutic gas source; and verifying the therapeutic gas source mated with a therapeutic gas supply subsystem has the correct identity, concentration, and/or expiration date.

9. The method of claim 8, wherein the shutoff valve down stream from the therapeutic gas source in a closed state until the correct identity, concentration, and/or expiration date is verified.

\* \* \* \* \*